(12) United States Patent
Wozniak-Knopp et al.

(10) Patent No.: US 10,982,008 B2
(45) Date of Patent: Apr. 20, 2021

(54) DOMAIN-EXCHANGED ANTIBODY

(71) Applicant: Merck Patent GmbH, Darmstadt (DE)

(72) Inventors: Gordana Wozniak-Knopp, Vienna (AT); Sylvia Dietrich, Vienna (AT); Florian Rüker, Vienna (AT); Alec Gross, Newton, MA (US); Stefan Becker, Darmstadt (DE)

(73) Assignee: MERCK PATENT GMBH, Darmstadt (DE)

(*) Notice: Subject to any disclaimer, the term of this patent is extended or adjusted under 35 U.S.C. 154(b) by 0 days.

(21) Appl. No.: 15/521,891

(22) PCT Filed: Dec. 4, 2015

(86) PCT No.: PCT/EP2015/078670
§ 371 (c)(1),
(2) Date: Apr. 25, 2017

(87) PCT Pub. No.: WO2016/087650
PCT Pub. Date: Jun. 9, 2016

(65) Prior Publication Data
US 2018/0016354 A1 Jan. 18, 2018

(30) Foreign Application Priority Data
Dec. 5, 2014 (EP) .................................. 14196518

(51) Int. Cl.
*C07K 16/46* (2006.01)
*C07K 16/28* (2006.01)

(52) U.S. Cl.
CPC .......... *C07K 16/468* (2013.01); *C07K 16/283* (2013.01); *C07K 16/2809* (2013.01); *C07K 16/2863* (2013.01); *C07K 2317/24* (2013.01); *C07K 2317/31* (2013.01); *C07K 2317/35* (2013.01); *C07K 2317/526* (2013.01); *C07K 2317/55* (2013.01); *C07K 2317/64* (2013.01); *C07K 2317/66* (2013.01); *C07K 2317/71* (2013.01); *C07K 2317/73* (2013.01); *C07K 2317/92* (2013.01); *C07K 2317/94* (2013.01)

(58) Field of Classification Search
CPC .............. C07K 16/468; C07K 2317/60; C07K 2317/31; C07K 2317/66
USPC ........................................................ 530/387.3
See application file for complete search history.

(56) References Cited

U.S. PATENT DOCUMENTS

| | | | |
|---|---|---|---|
| 6,331,415 B1 | 12/2001 | Cabilly et al. | |
| 2007/0287170 A1 | 12/2007 | Davis et al. | |
| 2018/0057567 A1* | 3/2018 | Rao | A61P 37/02 |
| 2018/0346605 A1* | 12/2018 | Chiu | C07K 16/241 |

FOREIGN PATENT DOCUMENTS

| | | |
|---|---|---|
| EP | 2006305 A2 | 12/2008 |
| EP | 1999154 B1 | 10/2012 |
| JP | 2012-136519 | 7/2012 |
| WO | 2006/072620 A1 | 7/2006 |
| WO | 2007/110205 A2 | 10/2007 |
| WO | 201/136172 A1 | 12/2010 |

OTHER PUBLICATIONS

Davis et al. (Protein Engineering, Design & Selection vol. 23 No. 4 pp. 195-202, 2010).*
Muda et al. (Protein Engineering, Design & Selection vol. 24 No. 5 pp. 447-454, 2011).*
Wozniak-Knopp et al. (PLOS One 13(4): e0195442; pp. 1-19; Apr. 8, 2018).*
Immunology: The Immune System in Health and Disease. 5th edition (2010) (www. ncbi.nlm.nih. gov/books/ NBK27144/ ; p. 1).*
Worn and Pluckthun ( J. Mol. Biol. 305:989-1010 (2001)).*
Lutterbuese, R. et al., Proc. Natl. Acad. Sci. USA 107, 12605-12610 (2010)).*
Atwell et al, "Stable Heterodimers from Remodeling the Domain Interface of a HOmodimer using a Phage Display Library", Journal of Molecular Biology, vol. 270, No. 1, 1997, pp. 26-35.
Beck et al, "Strategies and challenges for the next generation of therapeutic antibodies", Nature Reviews Immunology, 2010, vol. 10, No. 5, pp. 345-352.
Brodeur et al, "Mouse-Human Myeloma Partners for the Production of Meterohybridomas," 1987, Monoclonal Antibody Production Techniques and Applications, (Marcel Dekker, Inc., New York), pp. 51-63.
Davis et al, "SEEDbodies: fusion proteins based on strand-exchange engineered domain (SEED) CH3 heterodimers in an Fc analogue platform for asymmetric binders or immunofusions and bispecific antibodies", Protein Engineering, Design & Selection 2010, 23(4) 195-202.
Fleit et al, "Human neutrophil Fc gamma receptor distribution and structure", Proc.Natl.Acad.Sci.U.S.A., 1982, 79:3275-3279.
Gunasekaran et al, "Enhancing Antibody Fc Heterdimer Formation through Electrostatic Steering Effects", Journal of Biological Chemistry, vol. 285, No. 25, 2010, pp. 19637-19646.
Kim, Tracy, "Technology evaluation: Matuzumab, Merck KGaA", Curr Opin Mol Ther., 2004, 6(1):96-103. PubMed PMID: 15011787.
Kohler et al, "Continuous cultures of fused cells secreting antibody of predefined specificity", 1975, Nature vol. 256, 256:495-497.
Kollmannsberger et al, "A phase I study of the humanized monoclonal anti-epidermal growth factor receptor (EGFR) antibody EMD 72000 (matuzumab) in combination with paclitaxel in patients with EGFR-positive advanced non-small-cell lung cancer (NSCLC)", Annals of Oncology, 2006,17(6):1007-13 (Epub Mar. 13, 2006). PubMed PMID:16533873.

(Continued)

*Primary Examiner* — Lynn A Bristol
(74) *Attorney, Agent, or Firm* — Loza & Loza, LLP; Michael F. Fedrick

(57) ABSTRACT

The invention provides for a domain-exchanged antibody comprising a light chain (LC) composed of VL-CH3, and a heavy chain (HC) comprising VH-CH3-CH2-CH3, wherein the VL-CH3 of the LC is dimerising with the VH-CH3 of the HC thereby forming a domain-exchanged LC/HC dimer comprising a CH3LC/CH3HC domain pair, and means and method for producing the same.

12 Claims, 38 Drawing Sheets

Figure 1A:
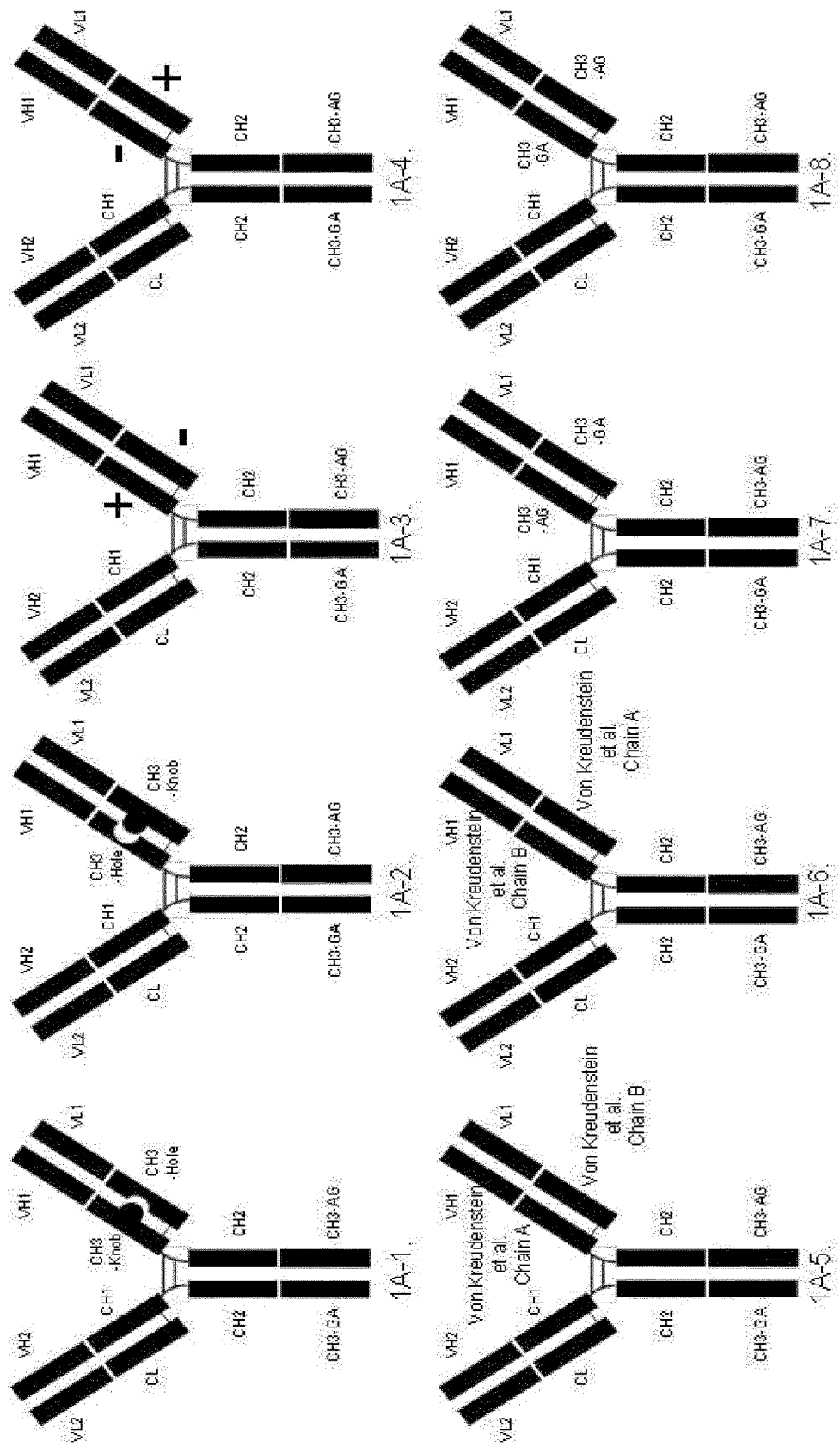

Specification includes a Sequence Listing.

(56) References Cited

OTHER PUBLICATIONS

Kozbor et al, "A human hybrid myeloma for production of human monoclonal antibodies", 1984, J. Immunol. 133:3001.
Lee et al, "Expression and functional reconstitution of a recombinant antibody (Fab') specific for human apolipoprotein B-100", 2003, J. Biotechnology 101:189-198.
Martin et al, "Crystal structure at 2.8 A of an FcRn/heterodimeric Fc complex: mechanism of pH-dependent binding", Mol Cell, 2001, 7(4):867-77. PubMed PMID: 11336709.
Peipp et al, "Molecular Engineering III: Fc Engineering", 2007, Handbook of Therapeutic Antibodies, pp. 171-196.
Ridgway et al, "'Knobs-into-holes' engineering of antibody CH3 domains for heavy chain heterodimerization", Protein Eng, 1996, 9(7):617-621.
Shi et al, "Purification and characterization of a recombinant G-protein-coupled receptor, *Saccharomyces cerevisiae* Ste2p, transiently expressed in HEK293 EBNA1 cells", Biochemistry, 2005, 44(48):15705-15714.
Van Wauwe et al, "OKT3: a monoclonal anti-human T lymphocyte antibody with potent mitogenic properties", J Immunol., 1980, 124(6):2708-13.
Von Kreudenstein et al, "Improving biophysical properties of a bispecific antibody scaffold to aid developability: quality by molecular design", MAbs., 2013, 5(5):646-54 (Epub Jul. 8, 2013). . doi: 10.4161/mabs.25632 PubMed PMID: 23924797.
Wibbenmeyer et al, "Cloning, expression, and characterization of the Fab fragment of the anti-lysozyme antibody HyHEL-5", 1999, Biochim Biophys Acta 1430(2):191-202.
International Search Report for PCT/EP15/78670 dated Mar. 7, 2016; 9 pages.
Written Opinion for PCT/EP15/78670 dated Mar. 7, 2016; 8 pages.
Extended European Search Report for EP Application No. 14196518.6 dated Jun. 22, 2015; 10 pages.
Klein et al. "Progress in overcoming the chain association issue in bispecific heterodimeric IgG antibodies." J. mAbs, 4(6):653-663 (2012).
Carter P., J of Immunological Methods, 2001, vol. 248, Issues 1-2, pp. 7-15.

\* cited by examiner

| Signal: | MWD1 A, Sig=214,8 Ref=360,100 | | | | |
|---|---|---|---|---|---|
| RT [min] | Type | Width [min] | Area | Height | Area% Name |
| 5.659 | BV | 0.2707 | 1390.5740 | 72.8631 | 2.7669 |
| 6.225 | VV F | 0.2300 | 536.5521 | 32.9434 | 1.0676 |
| 6.463 | VV | 0.2921 | 889.3045 | 45.4764 | 1.7695 |
| 7.455 | VV | 0.2725 | 42521.0977 | 2473.8083 | 84.6059 |
| 7.958 | VV B | 0.3798 | 4568.1870 | 173.1485 | 9.0895 |
| 9.478 | VBAB | 0.6457 | 352.1103 | 8.0597 | 0.7006 |
| | | Sum | 50257.8255 | | |

Signal: MWD1 A, Sig=214,8 Ref=360,100

| RT [min] | Type | Width [min] | Area | Height | Area% Name |
|---|---|---|---|---|---|
| 5.295 | BV F | 0.3082 | 79.2988 | 3.9163 | 0.3374 |
| 5.667 | VV | 0.3046 | 618.2583 | 29.0151 | 2.6304 |
| 6.454 | VV | 0.4444 | 795.3643 | 25.4623 | 3.3839 |
| 7.449 | VV | 0.2582 | 21325.1309 | 1281.1235 | 90.7280 |
| 8.368 | VB | 0.3542 | 686.4114 | 27.5965 | 2.9203 |
| | | Sum | 23504.4637 | | |

| Signal: | MWD1 A, Sig=214,8 Ref=360,100 | | | | |
|---|---|---|---|---|---|
| RT [min] | Type | Width [min] | Area | Height | Area% Name |
| 5.575 | BV | 0.3127 | 488.1194 | 22.1830 | 4.2530 |
| 6.773 | VV | 0.3583 | 5295.9565 | 222.0493 | 46.1434 |
| 7.466 | VV | 0.2798 | 4242.4229 | 229.3648 | 36.9640 |
| 8.387 | VV | 0.3582 | 1418.9808 | 57.8471 | 12.3635 |
| 9.717 | VB | 0.3151 | 31.6980 | 1.4274 | 0.2762 |
| | | Sum | 11477.1776 | | |

```
Signal:     MWD1 A, Sig=214,8 Ref=360,100
RT [min] Type  Width [min]      Area        Height      Area% Name
  5.707 BV       0.2464       735.9850     43.2807      4.3228
  6.507 VV       0.3989       291.5471     10.1566      1.7124
  7.494 VV       0.2519     15810.1738    981.8382     92.8611
  8.837 VV B     0.3956        97.2891      3.2649      0.5714
  9.637 VBAB     0.5239        90.6182      2.3392      0.5322
                   Sum      17025.6132
```

A

B 21-1.

21-2.

21-3.

21-4.

21-5.

Fig. 22

SEQ ID 1: VL(1)-CH3_HOLE (Y407T)
*DIQMTQSPSSLSASVGDRVTITCSASSSVTYMYWYQQKPGKAPKLLIYDTSNLASGVPSRFSGS
GSGTDYTFTISSLQPEDIATYYCQQWSSHIFTFGQGTKVEIK*RTVAEPQVYTLPPSRDELTKNQ
VSLTCLVKGFYPSDIAVEWESNGQPENNYKTTPPVLDSDGSFFLTSKLTVDKSRWQQGNVFSCS
VMHEALHNHYTQKSLSLSGEC

SEQ ID 2: VH(1)-CH3_KNOB (T366Y)-CH2-CH3<sub>AG</sub>
*QVQLVQSGAEVKKPGASVKVSCKASGYTFTSHWMHWVRQAPGQGLEWIGEFNPSNGRTNYNEKF
KSKATMTVDTSTNTAYMELSSLRSEDTAVYYCASRDYDYDGRYFDYWGQGTLVTVSS*ASTKGEP
QVYTLPPSRDELTKNQVSLYCLVKGFYPSDIAVEWESNGQPENNYKTTPPVLDSDGSFFLYSKL
TVDKSRWQQGNVFSCSVMHEALHNHYTQKSLSLSKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLHQ
DWLNGKEYKCKVSNKALPAPIEKTISKAK**GQPFRPEVHLLPPSREEMTKNQVSLTCLARGFYPK
DIAVEWESNGQPENNYKTTPSRQEPSQGTTTFAVTSKLTVDKSRWQQGNVFSCSVMHEALHNHY
TQKTISLSPGK**

SEQ ID 3: VL(2)-CL
*DIQMTQSPSSLSASVGDRVTITCSASSSVSYMNWYQQTPGKAPKRWIYDTSKLASGVPSRFSGS
GSGTDYTFTISSLQPEDIATYYCQQWSSNPFTFGQGTKLQIT*RTVAAPSVFIFPPSDEQLKSGT
ASVVCLLNNFYPREAKVQWKVDNALQSGNSQESVTEQDSKDSTYSLSSTLTLSKADYEKHKVYA
CEVTHQGLSSPVTKSFNRGEC

SEQ ID 4: VH(2)-CH1-CH2-CH3<sub>GA</sub>
*QVQLVQSGGGVVQPGRSLRLSCKASGYTFTRYTMHWVRQAPGKGLEWIGYINPSRGYTNYNQKV
KDRFTISRDNSKNTAFLQMDSLRPEDTGVYFCARYYDDHYCLDYWGQGTPVTVSS*ASTKGPSVF
PLAPSSKSTSGGTAALGCLVKDYFPEPVTVSWNSGALTSGVHTFPAVLQSSGLYSLSSVVTVPS
SSLGTQTYICNVNHKPSNTKVDKKVEPKSCDKTHTCPPCPAPELLGGPSVFLFPPKPKDTLMIS
RTPEVTCVVVDVSHEDPEVKFNWYVDGVEVHNAKTKPREEQYNSTYRVVSVLTVLHQDWLNGKE
YKCKVSNKALPAPIEKTISKAK**GQPREPQVYTLPPPSEELALNELVTLTCLVKGFYPSDIAVEW
LQGSQELPREKYLTWAPVLDSDGSFFLYSILRVAAEDWKKGDTFSCSVMHEALHNHYTQKSLDR
SPGK**

SEQ ID 5: VH(2)-CH1-CH2-CH3<sub>AG</sub>
*QVQLVQSGGGVVQPGRSLRLSCKASGYTFTRYTMHWVRQAPGKGLEWIGYINPSRGYTNYNQKV
KDRFTISRDNSKNTAFLQMDSLRPEDTGVYFCARYYDDHYCLDYWGQGTPVTVSS*ASTKGPSVF
PLAPSSKSTSGGTAALGCLVKDYFPEPVTVSWNSGALTSGVHTFPAVLQSSGLYSLSSVVTVPS
SSLGTQTYICNVNHKPSNTKVDKKVEPKSCDKTHTCPPCPAPELLGGPSVFLFPPKPKDTLMIS
RTPEVTCVVVDVSHEDPEVKFNWYVDGVEVHNAKTKPREEQYNSTYRVVSVLTVLHQDWLNGKE
YKCKVSNKALPAPIEKTISKAK**GQPFRPEVHLLPPSREEMTKNQVSLTCLARGFYPKDIAVEWE
SNGQPENNYKTTPSRQEPSQGTTTFAVTSKLTVDKSRWQQGNVFSCSVMHEALHNHYTQKTISL
SPGK**

Fig. 22 (continued)

SEQ ID 6: VH(1)-CH3_KNOB (T366Y)-CH2-CH3<sub>GA</sub>

*QVQLVQSGAEVKKPGASVKVSCKASGYTFTSHWMHWVRQAPGQGLEWIGEFNPSNGRTNYNEKF*
*KSKATMTVDTSTNTAYMELSSLRSEDTAVYYCASRDYDYDGRYFDYWGQGTLVTVSS*ASTKGEP
QVYTLPPSRDELTKNQVSLYCLVKGFYPSDIAVEWESNGQPENNYKTTPPVLDSDGSFFLYSKL
TVDKSRWQQGNVFSCSVMHEALHNHYTQKSLSLSKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPPSEELALNELVTLTCLVKGFYP
SDIAVEWLQGSQELPREKYLTWAPVLDSDGSFFLYSILRVAAEDWKKGDTFSCSVMHEALHNHY
TQKSLDRSPGK

SEQ ID 7: VL(1)-CH3wt

*DIQMTQSPSSLSASVGDRVTITCSASSSVTYMYWYQQKPGKAPKLLIYDTSNLASGVPSRFSGS*
*GSGTDYTFTISSLQPEDIATYYCQQWSSHIFTFGQGTKVEIKRTVAEPQVYTLPPSRDELTKNQ*
*VSLTCLVKGFYPSDIAVEWESNGQPENNYKTTPPVLDSDGSFFLYSKLTVDKSRWQQGNVFSCS*
*VMHEALHNHYTQKSLSLSGEC*

SEQ ID 8: VH(1)-CH3wt-CH2-CH3<sub>GA</sub>

*QVQLVQSGAEVKKPGASVKVSCKASGYTFTSHWMHWVRQAPGQGLEWIGEFNPSNGRTNYNEKF*
*KSKATMTVDTSTNTAYMELSSLRSEDTAVYYCASRDYDYDGRYFDYWGQGTLVTVSS*ASTKGEP
QVYTLPPSRDELTKNQVSLTCLVKGFYPSDIAVEWESNGQPENNYKTTPPVLDSDGSFFLYSKL
TVDKSRWQQGNVFSCSVMHEALHNHYTQKSLSLSKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPPSEELALNELVTLTCLVKGFYP
SDIAVEWLQGSQELPREKYLTWAPVLDSDGSFFLYSILRVAAEDWKKGDTFSCSVMHEALHNHY
TQKSLDRSPGK

SEQ ID 9: huFc_GA SEED

EPKSSDKTHTCPPCPAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALPAPIEKTISKAKGQP
REPQVYTLPPPSEELALNELVTLTCLVKGFYPSDIAVEWLQGSQELPREKYLTWAPVLDSDGSF
FLYSILRVAAEDWKKGDTFSCSVMHEALHNHYTQKSLDRSPGK

SEQ 10: VL(1)-CL

*DIQMTQSPSSLSASVGDRVTITCSASSSVTYMYWYQQKPGKAPKLLIYDTSNLASGVPSRFSGS*
*GSGTDYTFTISSLQPEDIATYYCQQWSSHIFTFGQGTKVEIK*RTVAAPSVFIFPPSDEQLKSGT
ASVVCLLNNFYPREAKVQWKVDNALQSGNSQESVTEQDSKDSTYSLSSTLTLSKADYEKHKVYA
CEVTHQGLSSPVTKSFNRGEC

Fig. 22 (continued)

SEQ 11: VH(1)-CH1-CH2-CH3<sub>AG</sub>

*QVQLVQSGAEVKKPGASVKVSCKASGYTFTSHWMHWVRQAPGQGLEWIGEFNPSNGRTNYNEKF
KSKATMTVDTSTNTAYMELSSLRSEDTAVYYCASRDYDYDGRYFDYWGQGTLVTVSS*ASTKGPS
VFPLAPSSKSTSGGTAALGCLVKDYFPEPVTVSWNSGALTSGVHTFPAVLQSSGLYSLSSVVTV
PSSSLGTQTYICNVNHKPSNTKVDKKVEPKSCDKTHTCPPCPAPELLGGPSVFLFPPKPKDTLM
ISRTPEVTCVVVDVSHEDPEVKFNWYVDGVEVHNAKTKPREEQYNSTYRVVSVLTVLHQDWLNG
KEYKCKVSNKALPAPIEKTISKAK**GQPFRPEVHLLPPSREEMTKNQVSLTCLARGFYPKDIAVE
WESNGQPENNYKTTPSRQEPSQGTTTFAVTSKLTVDKSRWQQGNVFSCSVMHEALHNHYTQKTI
SLSPGK**

SEQ ID 12: VL(3)-CL

*IVLTQSPASLAVSLGQRATISCKASQSVDFDGDSFMNWYQQKPGQPPKLLIYTTSNLESGIPAR
FSASGSGTDFTLNIHPVEEEDTATYYCQQSNEDPYTFGGGTKLELK*RTVAAPSVFIFPPSDEQL
KSGTASVVCLLNNFYPREAKVQWKVDNALQSGNSQESVTEQDSKDSTYSLSSTLTLSKADYEKH
KVYACEVTHQGLSSPVTKSFNRGEC

SEQ ID 13: VH(3)-CH1-CH2-CH3<sub>GA</sub>

*QVTLKESGPGILQPSQTLSLTCSFSGFSLRTSGMGVGWIRQPSGKGLEWLAHIWWDDDKRYNPA
LKSRLTISKDTSSNQVFLKIASVDTADTATYYCAQINPAWFAYWGQGTLVTVSA*ASTKGPSVFP
LAPSSKSTSGGTAALGCLVKDYFPEPVTVSWNSGALTSGVHTFPAVLQSSGLYSLSSVVTVPSS
SLGTQTYICNVNHKPSNTKVDKKVEPKSCDKTHTCPPCPAPELLGGPSVFLFPPKPKDTLMISR
TPEVTCVVVDVSHEDPEVKFNWYVDGVEVHNAKTKPREEQYNSTYRVVSVLTVLHQDWLNGKEY
KCKVSNKALPAPIEKTISKAK**GQPREPQVYTLPPPSEELALNELVTLTCLVKGFYPSDIAVEWL
QGSQELPREKYLTWAPVLDSDGSFFLYSILRVAAEDWKKGDTFSCSVMHEALHNHYTQKSLDRS
PGK**

SEQ ID 14: VH(3)-CH1-CH2-CH3<sub>AG</sub>

*QVTLKESGPGILQPSQTLSLTCSFSGFSLRTSGMGVGWIRQPSGKGLEWLAHIWWDDDKRYNPA
LKSRLTISKDTSSNQVFLKIASVDTADTATYYCAQINPAWFAYWGQGTLVTVSA*ASTKGPSVFP
LAPSSKSTSGGTAALGCLVKDYFPEPVTVSWNSGALTSGVHTFPAVLQSSGLYSLSSVVTVPSS
SLGTQTYICNVNHKPSNTKVDKKVEPKSCDKTHTCPPCPAPELLGGPSVFLFPPKPKDTLMISR
TPEVTCVVVDVSHEDPEVKFNWYVDGVEVHNAKTKPREEQYNSTYRVVSVLTVLHQDWLNGKEY
KCKVSNKALPAPIEKTISKAK**GQPFRPEVHLLPPSREEMTKNQVSLTCLARGFYPKDIAVEWES
NGQPENNYKTTPSRQEPSQGTTTFAVTSKLTVDKSRWQQGNVFSCSVMHEALHNHYTQKTISLS
PGK**

Fig. 22 (continued)

SEQ ID 15: VH(1)-CH3_KNOB (T366Y)-CH2$_{EN}$-CH3$_{AG}$

*QVQLVQSGAEVKKPGASVKVSCKASGYTFTSHWMHWVRQAPGQGLEWIGEFNPSNGRTNYNEKF*
*KSKATMTVDTSTNTAYMELSSLRSEDTAVYYCASRDYDYDGRYFDYWGQGTLVTVSS*ASTKGEP
QVYTLPPSRDELTKNQVSLYCLVKGFYPSDIAVEWESNGQPENNYKTTPPVLDSDGSFFLYSKL
TVDKSRWQQGNVFSCSVMHEALHNHYTQKSLSLSKSCDKTHTCPPCPAPPVAGPSVFLFPPKPK
DTLMISRTPEVTCVVVDVSHEDPEVQFNWYVDGVEVHNAKTKPREEQAQSTFRVVSVLTVVHQD
WLNGKEYKCKVSNKGLPAPIEKTISKTK**GQPFRPEVHLLPPSREEMTKNQVSLTCLARGFYPKD
IAVEWESNGQPENNYKTTPSRQEPSQGTTTFAVTSKLTVDKSRWQQGNVFSCSVMHEALHNHYT
QKTISLSPGK**

SEQ ID 16: huFc_g1hingeEN-CH2$_{EN}$-CH3$_{GA}$

EPKSSDKTHTCPPCPAPPVAGPSVFLFPPKPKDTLMISRTPEVTCVVVDVSHEDPEVQFNWYVD
GVEVHNAKTKPREEQAQSTFRVVSVLTVVHQDWLNGKEYKCKVSNKGLPAPIEKTISKTK**GQPR
EPQVYTLPPPSEELALNELVTLTCLVKGFYPSDIAVEWLQGSQELPREKYLTWAPVLDSDGSFF
LYSILRVAAEDWKKGDTFSCSVMHEALHNHYTQKSLDRSPGK**

SEQ ID 17: VH(3)-CH1-CH2$_{EN}$-CH3$_{GA}$

*QVTLKESGPGILQPSQTLSLTCSFSGFSLRTSGMGVGWIRQPSGKGLEWLAHIWWDDDKRYNPA
LKSRLTISKDTSSNQVFLKIASVDTADTATYYCAQINPAWFAYWGQGTLVTVSA*ASTKGPSVFP
LAPSSKSTSGGTAALGCLVKDYFPEPVTVSWNSGALTSGVHTFPAVLQSSGLYSLSSVVTVPSS
SLGTQTYICNVNHKPSNTKVDKKVEPKSCDKTHTCPPCPAPPVAGPSVFLFPPKPKDTLMISRT
PEVTCVVVDVSHEDPEVQFNWYVDGVEVHNAKTKPREEQAQSTFRVVSVLTVVHQDWLNGKEYK
CKVSNKGLPAPIEKTISKTK**GQPREPQVYTLPPPSEELALNELVTLTCLVKGFYPSDIAVEWLQ
GSQELPREKYLTWAPVLDSDGSFFLYSILRVAAEDWKKGDTFSCSVMHEALHNHYTQKSLDRSP
GK**

SEQ ID 18: VH(1)-CH3_KNOB (T366W)-CH2-CH3$_{AG}$

*QVQLVQSGAEVKKPGASVKVSCKASGYTFTSHWMHWVRQAPGQGLEWIGEFNPSNGRTNYNEKF
KSKATMTVDTSTNTAYMELSSLRSEDTAVYYCASRDYDYDGRYFDYWGQGTLVTVSS*ASTKGEP
QVYTLPPSRDELTKNQVSLWCLVKGFYPSDIAVEWESNGQPENNYKTTPPVLDSDGSFFLYSKL
TVDKSRWQQGNVFSCSVMHEALHNHYTQKSLSLSKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLHQ
DWLNGKEYKCKVSNKALPAPIEKTISKAK**GQPFRPEVHLLPPSREEMTKNQVSLTCLARGFYPK
DIAVEWESNGQPENNYKTTPSRQEPSQGTTTFAVTSKLTVDKSRWQQGNVFSCSVMHEALHNHY
TQKTISLSPGK**

SEQ ID 19: VL(1)-CH3_HOLE (T366S, L368A, Y407V)

*DIQMTQSPSSLSASVGDRVTITCSASSSVTYMYWYQQKPGKAPKLLIYDTSNLASGVPSRFSGS
GSGTDYTFTISSLQPEDIATYYCQQWSSHIFTFGQGTKVEIK*RTVAEPQVYTLPPSRDELTKNQ
VSLSCAVKGFYPSDIAVEWESNGQPENNYKTTPPVLDSDGSFFLVSKLTVDKSRWQQGNVFSCS
VMHEALHNHYTQKSLSLSGEC

Fig. 22 (continued)

SEQ ID 20: VH(1)-CH3_HOLE (T366S, L368A, Y407V)-CH2-CH3<sub>AG</sub>

*QVQLVQSGAEVKKPGASVKVSCKASGYTFTSHWMHWVRQAPGQGLEWIGEFNPSNGRTNYNEKF*
*KSKATMTVDTSTNTAYMELSSLRSEDTAVYYCASRDYDYDGRYFDYWGQGTLVTVSSA*STKGEP
QVYTLPPSRDELTKNQVSLSCAVKGFYPSDIAVEWESNGQPENNYKTTPPVLDSDGSFFLVSKL
TVDKSRWQQGNVFSCSVMHEALHNHYTQKSLSLSKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPFRPEVHLLPPSREEMTKNQVSLTCLARGFYPK
DIAVEWESNGQPENNYKTTPSRQEPSQGTTTFAVTSKLTVDKSRWQQGNVFSCSVMHEALHNHY
TQKTISLSPGK

SEQ ID 21: VL(1)-CH3_KNOB (T366W)

*DIQMTQSPSSLSASVGDRVTITCSASSSVTYMYWYQQKPGKAPKLLIYDTSNLASGVPSRFSGS*
*GSGTDYTFTISSLQPEDIATYYCQQWSSHIFTFGQGTKVEIK*RTVAEPQVYTLPPSRDELTKNQ
VSLWCLVKGFYPSDIAVEWESNGQPENNYKTTPPVLDSDGSFFLYSKLTVDKSRWQQGNVFSCS
VMHEALHNHYTQKSLSLSGEC

SEQ ID 22: VH(1)-CH3 (E356K, D399K)-CH2-CH3<sub>AG</sub>

*QVQLVQSGAEVKKPGASVKVSCKASGYTFTSHWMHWVRQAPGQGLEWIGEFNPSNGRTNYNEKF*
*KSKATMTVDTSTNTAYMELSSLRSEDTAVYYCASRDYDYDGRYFDYWGQGTLVTVSSA*STKGEP
QVYTLPPSRKEMTKNQVSLTCLVKGFYPSDIAVEWESNGQPENNYKTTPPVLKSDGSFFLYSKL
TVDKSRWQQGNVFSCSVMHEALHNHYTQKSLSLSKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPFRPEVHLLPPSREEMTKNQVSLTCLARGFYPK
DIAVEWESNGQPENNYKTTPSRQEPSQGTTTFAVTSKLTVDKSRWQQGNVFSCSVMHEALHNHY
TQKTISLSPGK

SEQ ID 23: VL(1)-CH3 (K392D, K409D)

*DIQMTQSPSSLSASVGDRVTITCSASSSVTYMYWYQQKPGKAPKLLIYDTSNLASGVPSRFSGS*
*GSGTDYTFTISSLQPEDIATYYCQQWSSHIFTFGQGTKVEIK*RTVAEPQVYTLPPSREEMTKNQ
VSLTCLVKGFYPSDIAVEWESNGQPENNYDTTPPVLDSDGSFFLYSDLTVDKSRWQQGNVFSCS
VMHEALHNHYTQKSLSLSGEC

SEQ ID 24: VH(1)-CH3 (K392D, K409D)-CH2-CH3<sub>AG</sub>

*QVQLVQSGAEVKKPGASVKVSCKASGYTFTSHWMHWVRQAPGQGLEWIGEFNPSNGRTNYNEKF*
*KSKATMTVDTSTNTAYMELSSLRSEDTAVYYCASRDYDYDGRYFDYWGQGTLVTVSSA*STKGEP
QVYTLPPSREEMTKNQVSLTCLVKGFYPSDIAVEWESNGQPENNYDTTPPVLDSDGSFFLYSDL
TVDKSRWQQGNVFSCSVMHEALHNHYTQKSLSLSKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPFRPEVHLLPPSREEMTKNQVSLTCLARGFYPK
DIAVEWESNGQPENNYKTTPSRQEPSQGTTTFAVTSKLTVDKSRWQQGNVFSCSVMHEALHNHY
TQKTISLSPGK

Fig. 22 (continued)

SEQ ID 25: VL(1)-CH3 (E356K, D399K)
*DIQMTQSPSSLSASVGDRVTITCSASSSVTYMYWYQQKPGKAPKLLIYDTSNLASGVPSRFSGS
GSGTDYTFTISSLQPEDIATYYCQQWSSHIFTFGQGTKVEIK*RTVAEPQVYTLPPSRKEMTKNQ
VSLTCLVKGFYPSDIAVEWESNGQPENNYKTTPPVLKSDGSFFLYSKLTVDKSRWQQGNVFSCS
VMHEALHNHYTQKSLSLSGEC

SEQ ID 26: VH(1)-CH3 (T350V, L351Y, F405A, Y407V)-CH2-CH3$_{AG}$
*QVQLVQSGAEVKKPGASVKVSCKASGYTFTSHWMHWVRQAPGQGLEWIGEFNPSNGRTNYNEKF
KSKATMTVDTSTNTAYMELSSLRSEDTAVYYCASRDYDYDGRYFDYWGQGTLVTVSS*ASTKGEP
QVYVYPPSREEMTKNQVSLTCLVKGFYPSDIAVEWESNGQPENNYKTTPPVLDSDGSFALVSKL
TVDKSRWQQGNVFSCSVMHEALHNHYTQKSLSLSKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLHQ
DWLNGKEYKCKVSNKALPAPIEKTISKAK**GQPFRPEVHLLPPSREEMTKNQVSLTCLARGFYPK
DIAVEWESNGQPENNYKTTPSRQEPSQGTTTFAVTSKLTVDKSRWQQGNVFSCSVMHEALHNHY
TQKTISLSPGK**

SEQ ID 27: VL(1)-CH3 (T350V, T366L, K392L, T394W)
*DIQMTQSPSSLSASVGDRVTITCSASSSVTYMYWYQQKPGKAPKLLIYDTSNLASGVPSRFSGS
GSGTDYTFTISSLQPEDIATYYCQQWSSHIFTFGQGTKVEIK*RTVAEPQVYVLPPSREEMTKNQ
VSLLCLVKGFYPSDIAVEWESNGQPENNYLTWPPVLDSDGSFFLYSKLTVDKSRWQQGNVFSCS
VMHEALHNHYTQKSLSLSGEC

SEQ ID 28: VH(1)-CH3 (T350V, T366L, K392L, T394W)-CH2-CH3$_{AG}$
*QVQLVQSGAEVKKPGASVKVSCKASGYTFTSHWMHWVRQAPGQGLEWIGEFNPSNGRTNYNEKF
KSKATMTVDTSTNTAYMELSSLRSEDTAVYYCASRDYDYDGRYFDYWGQGTLVTVSS*ASTKGEP
QVYVLPPSREEMTKNQVSLLCLVKGFYPSDIAVEWESNGQPENNYLTWPPVLDSDGSFFLYSKL
TVDKSRWQQGNVFSCSVMHEALHNHYTQKSLSLSKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLHQ
DWLNGKEYKCKVSNKALPAPIEKTISKAK**GQPFRPEVHLLPPSREEMTKNQVSLTCLARGFYPK
DIAVEWESNGQPENNYKTTPSRQEPSQGTTTFAVTSKLTVDKSRWQQGNVFSCSVMHEALHNHY
TQKTISLSPGK**

SEQ ID 29: VL(1)-CH3 (T350V, L351Y, F405A, Y407V)
*DIQMTQSPSSLSASVGDRVTITCSASSSVTYMYWYQQKPGKAPKLLIYDTSNLASGVPSRFSGS
GSGTDYTFTISSLQPEDIATYYCQQWSSHIFTFGQGTKVEIK*RTVAEPQVYVYPPSREEMTKNQ
VSLTCLVKGFYPSDIAVEWESNGQPENNYKTTPPVLDSDGSFALVSKLTVDKSRWQQGNVFSCS
VMHEALHNHYTQKSLSLSGEC

Fig. 22 (continued)

SEQ ID 30: VH(1)-CH3_SEED (AG)-CH2-CH3$_{AG}$
*QVQLVQSGAEVKKPGASVKVSCKASGYTFTSHWMHWVRQAPGQGLEWIGEFNPSNGRTNYNEKF*
*KSKATMTVDTSTNTAYMELSSLRSEDTAVYYCASRDYDYDGRYFDYWGQGTLVTVSSASTKG*PE
VHLLPPSREEMTKNQVSLTCLARGFYPKDIAVEWESNGQPENNYKTTPSRQEPSQGTTTFAVTS
KLTVDKSRWQQGNVFSCSVMHEALHNHYTQKTISLSKSCDKTHTCPPCPAPELLGGPSVFLFPP
KPKDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPFRPEVHLLPPSREEMTKNQVSLTCLARGFY
PKDIAVEWESNGQPENNYKTTPSRQEPSQGTTTFAVTSKLTVDKSRWQQGNVFSCSVMHEALHN
HYTQKTISLSPGK

SEQ ID 31: VL(1)-CH3_SEED (GA)
*DIQMTQSPSSLSASVGDRVTITCSASSSVTYMYWYQQKPGKAPKLLIYDTSNLASGVPSRFSGS*
*GSGTDYTFTISSLQPEDIATYYCQQWSSHIFTFGQGTKVEIKRTVA*EPQVYTLPPPSEELALNE
LVTLTCLVKGFYPSDIAVEWLQGSQELPREKYLTWAPVLDSDGSFFLYSILRVAAEDWKKGDTF
SCSVMHEALHNHYTQKSLDRSGEC

SEQ ID 32: VH(1)-CH3_SEED (GA)-CH2-CH3$_{AG}$
*QVQLVQSGAEVKKPGASVKVSCKASGYTFTSHWMHWVRQAPGQGLEWIGEFNPSNGRTNYNEKF*
*KSKATMTVDTSTNTAYMELSSLRSEDTAVYYCASRDYDYDGRYFDYWGQGTLVTVSSASTKG*__EP__
QVYTLPPPSEELALNELVTLTCLVKGFYPSDIAVEWLQGSQELPREKYLTWAPVLDSDGSFFLY
SILRVAAEDWKKGDTFSCSVMHEALHNHYTQKSLDRSKSCDKTHTCPPCPAPELLGGPSVFLFP
PKPKDTLMISRTPEVTCVVVDVSHEDPEVKFNWYVDGVEVHNAKTKPREEQYNSTYRVVSVLTV
LHQDWLNGKEYKCKVSNKALPAPIEKTISKAKGQPFRPEVHLLPPSREEMTKNQVSLTCLARGF
YPKDIAVEWESNGQPENNYKTTPSRQEPSQGTTTFAVTSKLTVDKSRWQQGNVFSCSVMHEALH
NHYTQKTISLSPGK

SEQ ID 33: VL(1)-CH3_SEED (AG)
*DIQMTQSPSSLSASVGDRVTITCSASSSVTYMYWYQQKPGKAPKLLIYDTSNLASGVPSRFSGS*
*GSGTDYTFTISSLQPEDIATYYCQQWSSHIFTFGQGTKVEIKRTVA*PEVHLLPPSREEMTKNQV
SLTCLARGFYPKDIAVEWESNGQPENNYKTTPSRQEPSQGTTTFAVTSKLTVDKSRWQQGNVFS
CSVMHEALHNHYTQKTISLSGEC

SEQ ID 34: VH(1)-CH3 (E356K, D399K)-CH2-CH3_HOLE (T366S, L368A, Y407V)
*QVQLVQSGAEVKKPGASVKVSCKASGYTFTSHWMHWVRQAPGQGLEWIGEFNPSNGRTNYNEKF*
*KSKATMTVDTSTNTAYMELSSLRSEDTAVYYCASRDYDYDGRYFDYWGQGTLVTVSSASTKG*EP
QVYTLPPSRKEMTKNQVSLTCLVKGFYPSDIAVEWESNGQPENNYKTTPPVLKSDGSFFLYSKL
TVDKSRWQQGNVFSCSVMHEALHNHYTQKSLSLSKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLSCAVKGFYPS
DIAVEWESNGQPENNYKTTPPVLDSDGSFFLVSKLTVDKSRWQQGNVFSCSVMHEALHNHYTQK
SLSLSPGK

Fig. 22 (continued)

SEQ ID 35: VH(1)-CH3 (K392D, K409D)-CH2-CH3_HOLE (T366S, L368A, Y407V)
*QVQLVQSGAEVKKPGASVKVSCKASGYTFTSHWMHWVRQAPGQGLEWIGEFNPSNGRTNYNEKF*
*KSKATMTVDTSTNTAYMELSSLRSEDTAVYYCASRDYDYDGRYFDYWGQGTLVTVSS*ASTKGEP
QVYTLPPSREEMTKNQVSLTCLVKGFYPSDIAVEWESNGQPENNYDTTPPVLDSDGSFFLYSDL
TVDKSRWQQGNVFSCSVMHEALHNHYTQKSLSLSKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLSCAVKGFYPS
DIAVEWESNGQPENNYKTTPPVLDSDGSFFLVSKLTVDKSRWQQGNVFSCSVMHEALHNHYTQK
SLSLSPGK

SEQ ID 36: VH(1)-CH3 (T350V, L351Y, F405A, Y407V)-CH2-CH3_HOLE (T366S, L368A, Y407V)
*QVQLVQSGAEVKKPGASVKVSCKASGYTFTSHWMHWVRQAPGQGLEWIGEFNPSNGRTNYNEKF*
*KSKATMTVDTSTNTAYMELSSLRSEDTAVYYCASRDYDYDGRYFDYWGQGTLVTVSS*ASTKGEP
QVYVYPPSREEMTKNQVSLTCLVKGFYPSDIAVEWESNGQPENNYKTTPPVLDSDGSFALVSKL
TVDKSRWQQGNVFSCSVMHEALHNHYTQKSLSLSKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLSCAVKGFYPS
DIAVEWESNGQPENNYKTTPPVLDSDGSFFLVSKLTVDKSRWQQGNVFSCSVMHEALHNHYTQK
SLSLSPGK

SEQ ID 37: VH(1)-CH3 (T350V, T366L, K392L, T394W)-CH2-CH3_HOLE (T366S, L368A, Y407V)
*QVQLVQSGAEVKKPGASVKVSCKASGYTFTSHWMHWVRQAPGQGLEWIGEFNPSNGRTNYNEKF*
*KSKATMTVDTSTNTAYMELSSLRSEDTAVYYCASRDYDYDGRYFDYWGQGTLVTVSS*ASTKGEP
QVYVLPPSREEMTKNQVSLLCLVKGFYPSDIAVEWESNGQPENNYLTWPPVLDSDGSFFLYSKL
TVDKSRWQQGNVFSCSVMHEALHNHYTQKSLSLSKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLSCAVKGFYPS
DIAVEWESNGQPENNYKTTPPVLDSDGSFFLVSKLTVDKSRWQQGNVFSCSVMHEALHNHYTQK
SLSLSPGK

SEQ ID 38: VH(1)-CH3_SEED (AG)-CH2-CH3_HOLE (T366S, L368A, Y407V)
*QVQLVQSGAEVKKPGASVKVSCKASGYTFTSHWMHWVRQAPGQGLEWIGEFNPSNGRTNYNEKF*
*KSKATMTVDTSTNTAYMELSSLRSEDTAVYYCASRDYDYDGRYFDYWGQGTLVTVSS*ASTKGPE
VHLLPPSREEMTKNQVSLTCLARGFYPKDIAVEWESNGQPENNYKTTPSRQEPSQGTTTFAVTS
KLTVDKSRWQQGNVFSCSVMHEALHNHYTQKTISLSKSCDKTHTCPPCPAPELLGGPSVFLFPP
KPKDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSREEMTKNQVSLSCAVKGFY
PSDIAVEWESNGQPENNYKTTPPVLDSDGSFFLVSKLTVDKSRWQQGNVFSCSVMHEALHNHYT
QKSLSLSPGK

Fig. 22 (continued)

SEQ ID 39: VH(1)-CH3_SEED (GA)-CH2-CH3_HOLE (T366S, L368A, Y407V)
QVQLVQSGAEVKKPGASVKVSCKASGYTFTSHWMHWVRQAPGQGLEWIGEFNPSNGRTNYNEKF
KSKATMTVDTSTNTAYMELSSLRSEDTAVYYCASRDYDYDGRYFDYWGQGTLVTVSSASTKG<ins>EP
QVYTLPPPSEELALNELVTLTCLVKGFYPSDIAVEWLQGSQELPREKYLTWAPVLDSDGSFFLY
SILRVAAEDWKKGDTFSCSVMHEALHNHYTQKSLDRS</ins>KSCDKTHTCPPCPAPELLGGPSVFLFP
PKPKDTLMISRTPEVTCVVVDVSHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLSCAVKGF
YPSDIAVEWESNGQPENNYKTTPPVLDSDGSFFLVSKLTVDKSRWQQGNVFSCSVMHEALHNHY
TQKSLSLSPGK

SEQ ID 40: huFc_ KNOB (T366W)
EPKSSDKTHTCPPCPAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALPAPIEKTISKAKGQP
REPQVYTLPPSREEMTKNQVSLWCLVKGFYPSDIAVEWESNGQPENNYKTTPPVLDSDGSFFLY
SKLTVDKSRWQQGNVFSCSVMHEALHNHYTQKSLSLSPGK

SEQ ID 41:
GQPREPQVYTLPPSRDELTKNQVSLTCLVKGFYPSDIAVEWESNGQPENNYKTTPPVLDSDGSF
FLYSKLTVDKSRWQQGNVFSCSVMHEALHNHYTQKSLSLSP

SEQ ID 42
GQPREPQVYTLPPSREEMTKNQVSLTCLVKGFYPSDIAVEWESNGQPENNYKTTPPMLDSDGSF
FLYSKLTVDKSRWQQGNVFSCSVMHEALHNHYTQKSLSLSP

SEQ ID 43
GQPREPQVYTLPPSREEMTKNQVSLTCLVKGFYPSDIAVEWESSGQPENNYNTTPPMLDSDGSF
FLYSKLTVDKSRWQQGNIFSCSVMHEALHNRFTQKSLSLSP

SEQ ID 44
GQPREPQVYTLPPSQEEMTKNQVSLTCLVKGFYPSDIAVEWESNGQPENNYKTTPPVLDSDGSF
FLYSRLTVDKSRWQEGNVFSCSVMHEALHNHYTQKSLSLSL

SEQ ID 45
GNTFRPEVHLLPPPSEELALNELVTLTCLARGFSPKDVLVRWLQGSQELPREKYLTWASRQEPS
QGTTTFAVTSILRVAAEDWKKGDTFSCMVGHEALPLAFTQKTIDRLA

SEQ ID 46
DQDTAIRVFAIPPSFASIFLTKSTKLTCLVTDLTTYDSVTISWTRQNGEAVKTHTNISESHPNA
TFSAVGEASICEDDWNSGERFTCTVTHTDLPSPLKQTISRPK

Fig. 22 (continued)

SEQ ID 47
DSNPRGVSAYLSRPSPFDLFIRKSPTITCLVVDLAPSKGTVNLTWSRASGKPVNHSTRKEEKQR
NGTLTVTSTLPVGTRDWIEGETYQCRVTHPHLPRALMRSTTKTS

SEQ ID 48
AAQAPVKLSLNLLASSDPPEAASWLLCEVSGFSPPNILLMWLEDQREVNTSGFAPARPPPQPRS
TTFWAWSVLRVPAPPSPQPATYTCVVSHEDSRTLLNASRSLEVS

SEQ ID 49
RTVA

SEQ ID 50
EPQV

SEQ ID 51
QKSLSLS

SEQ ID 52
VTVSS

SEQ ID 53
ASTKG

DOMAIN-EXCHANGED ANTIBODY

CROSS-REFERENCE TO RELATED APPLICATIONS

This application is the U.S. national stage of International Patent Application No. PCT/EP2015/078670, filed on Dec. 4, 2014 and entitled DOMAIN-EXCHANGED ANTIBODY, which claims the benefit of priority under 35 U.S.C. § 119 from European Patent Application No. 14196518.6, filed Dec. 5, 2014. The disclosures of the foregoing applications are incorporated herein by reference in their entirety.

SEQUENCE LISTING

The entire content of a Sequence Listing titled "Sequence_ Listing.txt," created on Apr. 3, 2017 and having a size of 130 kilobytes, which has been submitted in electronic form in connection with the present application, is hereby incorporated by reference herein in its entirety.

FIELD OF THE INVENTION

The invention relates to a domain-exchanged antibody comprising a light chain (LC), and a heavy chain (HC), wherein the LC is dimerising with the HC.

BACKGROUND

Monoclonal antibodies have been widely used as therapeutic binding agents. The basic antibody structure will be explained here using as example an intact IgG1 immunoglobulin.

Two identical heavy (H) and two identical light (L) chains combine to form the Y-shaped antibody molecule. The heavy chains each have four domains. The amino terminal variable domains (VH) are at the tips of the Y. These are followed by three constant domains: CH1, CH2, and the carboxy-terminal CH3, at the base of the Y's stem. A short stretch, the switch, connects the heavy chain variable and constant regions. The hinge connects CH2 and CH3 (the Fc fragment) to the remainder of the antibody (the Fab fragments). One Fc and two identical Fab fragments can be produced by proteolytic cleavage of the hinge in an intact antibody molecule. The light chains are constructed of two domains, variable (VL) and constant (CL), separated by a switch.

Disulfide bonds in the hinge region connect the two heavy chains. The light chains are coupled to the heavy chains by additional disulfide bonds. Asn-linked carbohydrate moieties are attached at different positions in constant domains depending on the class of immunoglobulin. For IgG1 two disulfide bonds in the hinge region, between Cys235 and Cys238 pairs, unite the two heavy chains. The light chains are coupled to the heavy chains by two additional disulfide bonds, between Cys229s in the CH1 domains and Cys214s in the CL domains. Carbohydrate moieties are attached to Asn306 of each CH2, generating a pronounced bulge in the stem of the Y.

These features have profound functional consequences. The variable regions of both the heavy and light chains (VH) and (VL) lay at the N-terminal region, i.e. the "tips" of the Y, where they are positioned to react with antigen. This tip of the molecule is the side on which the N-terminus of the amino acid sequence is located. The stem of the Y projects in a way to efficiently mediate effector functions such as the activation of complement and interaction with Fc receptors, or ADCC and ADCP. Its CH2 and CH3 domains bulge to facilitate interaction with effector proteins. The C-terminus of the amino acid sequence is located on the opposite side of the tip, which can be termed "bottom" of the Y.

Two types of light chain, termed lambda (λ) and kappa (κ), are found in antibodies. A given immunoglobulin either has κ chains or λ chains, never one of each. No functional difference has been found between antibodies having λ or κ light chains.

Each domain in an antibody molecule has a similar structure of two beta sheets packed tightly against each other in a compressed antiparallel beta barrel. This conserved structure is termed the immunoglobulin fold. The immunoglobulin fold of constant domains contains a 3-stranded sheet packed against a 4-stranded sheet. The fold is stabilized by hydrogen bonding between the beta strands of each sheet, by hydrophobic bonding between residues of opposite sheets in the interior, and by a disulfide bond between the sheets. The 3-stranded sheet comprises strands C, F, and G, and the 4-stranded sheet has strands A, B, E, and D. The letters A through G denote the sequential positions of the beta strands along the amino acid sequence of the immunoglobulin fold.

The fold of variable domains has 9 beta strands arranged in two sheets of 4 and 5 strands. The 5-stranded sheet is structurally homologous to the 3-stranded sheet of constant domains, but contains the extra strands C' and C". The remainder of the strands (A, B, C, D, E, F, G) have the same topology and similar structure as their counterparts in constant domain immunoglobulin folds. A disulfide bond links strands B and F in opposite sheets, as in constant domains.

The variable domains of both light and heavy immunoglobulin chains contain three hypervariable loops, or complementarity-determining regions (CDRs). The three CDRs of a V domain (CDR1, CDR2, CDR3) cluster at one end of the beta barrel. The CDRs are loops that connect beta strands B-C, C'-C", and F-G of the immunoglobulin fold. The residues in the CDRs vary from one immunoglobulin molecule to the next, imparting antigen specificity to each antibody.

The VL and VH domains at the tips of antibody molecules are closely packed such that the 6 CDRs (3 on each domain) cooperate in constructing a surface (or cavity) for antigen-specific binding. The natural antigen binding site of an antibody thus is composed of the loops which connect strands B-C, C'-C", and F-G of the light chain variable domain and strands B-C, C'-C", and F-G of the heavy chain variable domain.

The loops which are not CDR-loops in a native immunoglobulin, or not part of the antigen-binding pocket as determined by the CDR loops and optionally adjacent loops within the CDR loop region, do not have antigen binding or epitope binding specificity, but contribute to the correct folding of the entire immunoglobulin molecule and/or its effector or other functions and are therefore called structural loops.

Prior art documents show that the immunoglobulin-like scaffold has been employed so far for the purpose of manipulating the existing antigen binding site, thereby introducing novel binding properties. In most cases the CDR regions have been engineered for antigen binding, in other words, in the case of the immunoglobulin fold, only the natural antigen binding site has been modified in order to change its binding affinity or specificity. A vast body of literature exists which describes different formats of such manipulated immunoglobulins, frequently expressed in the form of single-chain Fv fragments (scFv) or Fab fragments, either displayed on the surface of phage particles or solubly expressed in various prokaryotic or eukaryotic expression systems.

WO2006/072620A1 describes a method of engineering an immunoglobulin which comprises a modification in a structural loop region to obtain new antigen binding sites. This method is broadly applicable to immunoglobulins and may be used to produce a library of immunoglobulins targeting a variety of antigens. A CH3 library has been shown to be useful for selecting specific library members which are capable of binding an antigen through the structural loops. Such structural loop binders are herein also referred to as "immune" CH3. According to an example, a Fab-like structure has been engineered which includes immune CH3 domains to substitute for the CH1 and CL domains.

Specific bispecific antibodies antibody constructs are currently in development for improved therapeutics. Bivalent IgG depends upon dimerization of its heavy chains, mediated by homodimeric association of its CH3 domains.

Davis et al (Protein Engineering, Design & Selection 2010, 23(4) 195-202) describe a heterodimeric Fc platform that supports the design of bispecific and asymmetric fusion proteins by using strand-exchange engineered domain (SEED) CH3 heterodiomers. These derivatives of human IgG and IgA CH3 domains create complementary human SEED CH3 heterodimers that are composed of alternating segments of human IgA and IgG sequences. The SEED engineering is further described in EP1999154B1. WO 2010/136172 A1 discloses tri- or tetra specific antibodies that comprise one or two single-chain Fac connected to the C-terminus of the Fc part of the antibody.

Peipp et al. (1 Jan. 2007, Handbook of Therapeutic Antibodies, pp 171-196) provides an overview on Fc engineering.

Beck et al, (Nature Reviews Immunology, vol. 10, no. 5, 1 May 2010, pp 345-352) describes next generation therapeutic antibodies, and particularly refers to different types of bispecific antibodies.

Ridgway et al. (Protein Engineering, vol. 9, no. 7, 1996, pp 617-621) describes "knobs into-holes" engineering of antibody CH3 domains for heavy chain heterodimerization.

Atwell et al. (Journal Of Molecular Biology, vol. 270, no. 1, 1997, pp 26-35) describes combination of interface residues for antibody CH3 domains that promote the formation of stable CH3 heterodimers, including "knob" and "hole" mutants.

Davis et al. (Protein Engineering Design And Selection, vol. 23, no. 4, 2010, pp 195-202) and WO 2007/110205 A2 describe SEEDbodies which are fusion proteins based on strand-exchange engineered domain (SEED) CH3 heterodimers and bispecific antibodies.

Gunasekaran et al. (Journal Of Biological Chemistry, vol. 285, no. 25, 2010, pp 19637-19646) describe enhancing antibody Fc heterodimer formation through electrostatic steering effects and novel Fc mutations to charge polyrity across the Fc dimer interface.

Von Kreudenstein et al. (Landes Bioscience, vol. 5, no. 5, 2013, pp 646-654) describe a bispecific antibody scaffold based on a heterodimeric Fc engineered for stability.

SUMMARY OF THE INVENTION

It is the objective of the present invention to provide antibodies with an improved structure such as to engineer asymmetric molecules, e.g. to produce bispecific antibodies.

The object is solved by the subject of the present invention.

According to the invention there is provided a domain-exchanged antibody comprising a light chain (LC) composed of VL-CH3, and a heavy chain (HC) comprising VH-CH3-CH2-CH3, wherein the VL-CH3 of the LC is dimerising with the VH-CH3 of the HC thereby forming a domain-exchanged LC/HC dimer comprising a $CH3_{LC}/CH3_{HC}$ domain pair.

Specifically, the antibody comprises at least one C-terminal extension, wherein the extension comprises another $CH3_{LC}/CH3_{HC}$ domain pair. Said another $CH3_{LC}/CH3_{HC}$ domain pair is specifically a terminal one. For example, the antibody is extended by fusing a Fab fragment to the C-terminus of one or both of the CH3 domains of the Fc-part (the $CH3_{HC}/CH3_{HC}$ domain pair), with or without a linker sequence. In particular, the extension may comprise one or two Fab fragments, such that the antibody comprises two, three, or four Fab arms, wherein at least one of the Fab arms comprises the domain exchange. Thus, at least one Fab arm comprises the $CH3_{LC}/CH3_{HC}$ domain pair. Specifically, two, three or four Fab arms may comprise a $CH3_{LC}/CH3_{HC}$ domain pair.

Specifically, any or each of the CH3 domains is a IgG1 CH3 domains, specifically characterized by a human IgG1 CH3 sequence or an engineered variant thereof comprising one or more point mutations, preferably up to 10 point mutations.

Specifically, the CH2 domain is of the IgG2 type, specifically characterized by a human IgG2 CH2 sequence, or an engineered variant thereof, comprising one or more point mutations, preferably up to 10 point mutations.

It is well understood that any antibody may comprise one or more domain-exchanged Fab arms in a C-terminal extension of the antibody, e.g. an IgG antibody. An antibody C-terminally extended by a Fab arm may be provided, wherein the N-terminus of the VL or VH domain of the Fab arm is fused to the C-terminus of the CH3 of the Fc part of the antibody, with or without a linker sequence. In particular, an antibody may comprise one, two, three, or four Fab arms, wherein at least one of the Fab arms is a domain-exchanged Fab arm. Thus, at least one Fab arm comprises the $CH3_{LC}/CH3_{HC}$ domain pair. Specifically, two, three or four Fab arms may comprise the $CH3_{LC}/CH3_{HC}$ domain pair.

Specifically, each of the Fab arms comprises a functional antigen-binding site composed of a VH/VL domain pair, capable of binding a target with a high affinity and a KD of less than any of $10^{-6}M$, $10^{-7}M$, $10^{-8}M$, $10^{-9}M$, or $10^{-10}M$. Specifically, the antibody is a domain-exchanged bispecific or heterodimeric antibody targeting two different antigens, wherein each of the antigens is recognized by the antibody with a KD of less than any of $10^{-6}M$, $10^{-7}M$, $10^{-8}M$, $10^{-9}M$, or $10^{-10}M$.

Specifically, the antibody comprises a hinge region, preferably a human hinge region e.g. a human IgG1 hinge region.

According to a specific aspect, the antibody further comprises an Fc region characterized by a $CH3_{HC}/CH3_{HC}$ dimer. The Fc region is specifically characterized by a dimer of Fc chains each characterized by comprising the CH2-CH3 chain, which dimer can be a homodimer or a heterodimer, e.g. wherein a first Fc chain differs from a second Fc chain in at least one point mutation in the CH2 and/or CH3 domains.

Specifically, the antibody comprises only one LC/HC dimer, wherein the HC is further dimerized with an Fc chain comprising CH2-CH3, thereby obtaining the Fc region. Such antibody is specifically characterized by only one Fab arm and the Fc region.

According to a specific aspect, the invention provides for a domain-exchanged antibody comprising a light chain (LC) and a heavy chain (HC), which HC is dimerised with another HC thereby forming a HC/HC dimer, which comprises at least one C-terminal extension, wherein the extension comprises a $CH3_{LC}/CH3_{HC}$ domain pair. Such domain-exchanged antibody may specifically comprise two LC and two HC, wherein at least one HC is extended by one or two Fab arms. The antibody specifically comprises at least one at least one Fab arm and at least one domain-exchanged Fab arm, wherein a) a Fab arm comprises VL-CL domains paired with VH-CH1 domains to form a dimer of two domain chains; and b) a domain-exchanged Fab arm comprises $VL-CH3_{LC}$ domains paired with $VH-CH3_{HC}$ domains, thereby forming the $CH3_{LC}/CH3_{HC}$ domain pair.

Specifically, the antibody comprises one, two or three Fab arms, which are not domain-exchanged according to a) above, and one, two, or three domain-exchanged Fab arms according to b) above.

Figure 21:
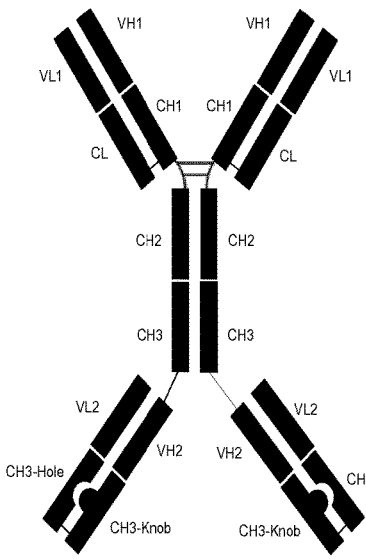
Figure 21:
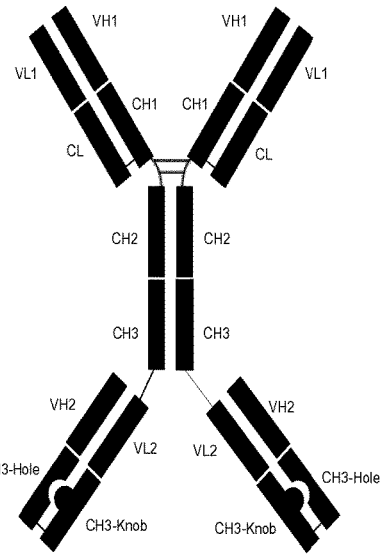
Figure 21:
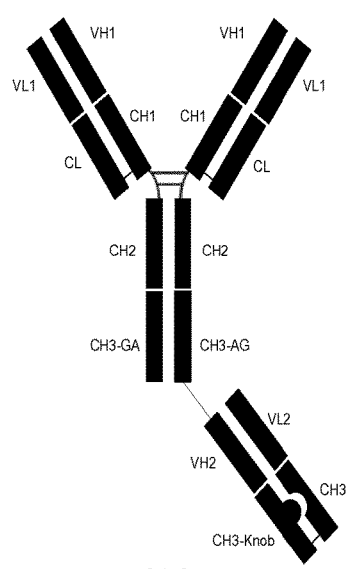
Figure 21:
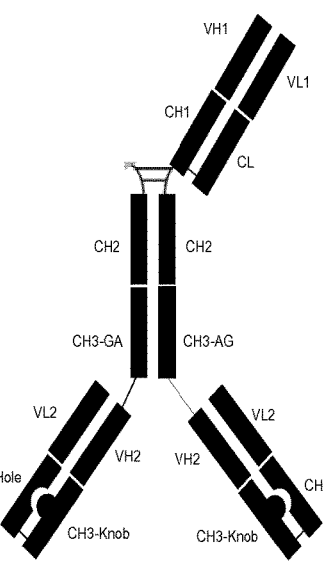
Figure 21:
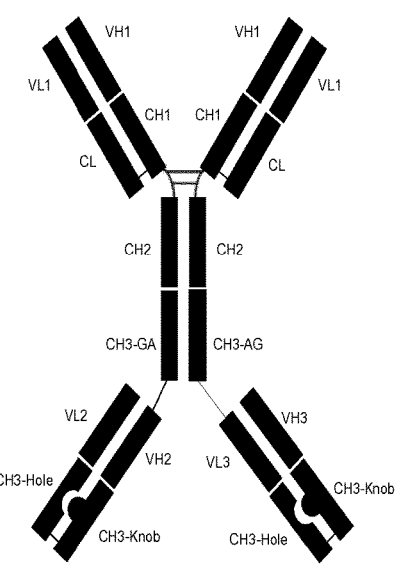

Specific embodiments are illustrated in FIG. 21.

For example, the HC of an antibody could be VH1-CH1-CH2-CH3-VH2-CH3$_{HET}$, VH1-CH1-CH2-CH3(AG_SEED)-VH2-CH3(knob), VH1-CH1-CH2-CH3(AG_SEED)-VL2-CH3(knob), VH2-CH3$_{HET}$-VH1-CH1-CH2-CH3.

For example, a tetravalent bispecific antibody may be obtained by adding the domain-exchanged Fab to the C-terminus of a native antibody.

Alternatively, an antibody that is bivalent for one target and monovalent for a second target, may be obtained by combining a heterodimeric HC/HC pair, where only one HC in the pair has a second domain-exchanged Fab linked to the C-terminus.

According to a specific aspect, said one or more domain-exchanged Fab arms in the C-terminal extension of the antibody comprise a CH3 domain which is engineered to alter the pH dependent FcRn binding. For example, at least one of the CH3 domains of the $CH3_{LC}/CH3_{HC}$ domain pair can be engineered to comprise at least one mutation at the FcRn binding site to reduce pH-dependent FcRn binding.

Reduction of pH-dependent FcRn binding may be such that the binding affinity to bind FcRn in a pH-dependent way is less than 1-log, preferably about the same or less at pH5-6 as compared to the same binding affinity at physiological pH (pH7.4).

A CH3 domain with reduced pH-dependent FcRn binding may specifically comprise at least one of the H433A or H435A mutations, or both H433A or H435A mutations, wherein the numbering is according to the EU index of Kabat.

A specific embodiment of $CH3_{LC}$ and $CH3_{HC}$ variants without the native CH3 domain pH-dependent FcRn binding site is obtained by introduction of H433A and H435A mutations (numbering according to EU index of Kabat), which is part of the pH-dependent FcRn binding site contributed from the native CH3 domain sequence [9], sequences see FIG. 22.

The number of a mutated amino acid of a CH3 domain as described herein is provided as a position corresponding to the Kabat numbering. The Kabat numbering originally refers to the numbering of a naturally-occurring antibody. In an antibody of the invention, which comprises a domain-exchanged structure, the number of an amino acid in the CH3 domain according to the EU index of Kabat is specifically understood as the analogous position as determined by the CH3 domain structure in a naturally-occurring antibody.

Specifically, the CH3 domains in the $CH3_{LC}/CH3_{HC}$ domain pair are heterologous, in particular wherein a CH3 domain is incorporated into the antibody structure at a position which is "foreign" to the molecule. Thereby, a domain-exchanged antibody can be produced. The heterologous CH3 is herein also referred to as $CH3_{HET}$. Thus, the $CH3_{LC}/CH3_{HC}$ domain pair is specifically a heterologous dimer ($CH3_{HET}/CH3_{HET}$), wherein each of the $CH3_{HET}$ is N-terminally linked to a variable domain, e.g. wherein a first $CH3_{HET}$ antibody domain is N-terminally linked to VL domain, thereby producing a LC, and a second $CH3_{HET}$ is linked to a VH domain, thereby producing part of the HC, which first and second $CH3_{HET}$ form a dimer at least through contact of a beta-sheet region of the first and second $CH3_{HET}$ domains. Specifically, the first and second $CH3_{HET}$ domains are nonimmune CH3 domains, which do not incorporate an antigen-binding site in the structural loop region, such as a non-CDR binding site. The nonimmune CH3 domain specifically does not comprise a CDR-like binding site capable of antigen-binding.

Specifically, the $CH3_{HET}/CH3_{HET}$ dimer is a heterodimer consisting of two CH3 domains which differ from each other in the amino acid sequence, or a homodimer of two CH3 domains which have the same amino acid sequence.

Specifically, a structure is produced which is alike a full-length structure of an antibody, e.g. an IgG, thereby producing an IgG-like structure which is the same structure of an IgG, yet, with a domain-exchange by introducing an additional pair of $CH3_{HET}$ domains at a position which is different form the wild-type position, specifically to substitute the CH1/CL pair of domains which is to be exchanged for the pair of $CH3_{HET}$ domains. In the full-length antibody, one or both of the Fab arms may be a Fab-like structure. Thus, one or both pairs of LC and HC may comprise the domain-exchanged structure including the $CH3_{HET}/CH3_{HET}$ dimer.

Specifically, the IgG-like structure is obtained by extending the (Fab)$_2$-like structure through fusion of an Fc part. Thereby, each of the heavy chains is C-terminally extended by a CH2-CH3 domain sequence.

According to a specific embodiment, the antibody is an IgG antibody, wherein the LC is composed of VL-CH3, optionally wherein the domains are directly linked or wherein the LC is further comprising one or more linker or hinge regions as a junction between antibody domains.

According to a specific embodiment, the antibody is an IgG antibody, wherein the HC is composed of VH-CH3-CH2-CH3, optionally wherein the domains are directly linked or wherein the HC is further comprising one or more linker or hinge regions as a junction between antibody domains.

Specifically, the antibody of the invention has an IgG-like structure which comprises only one Fab-like structure and one wild-type Fab structure. Thus, according to a specific embodiment, the antibody comprises or is consisting of a) one LC composed of VL-CH3, and a HC composed of VH-CH3-CH2-CH3, wherein the VL-CH3 of the LC is dimerising with the VH-CH3 of the HC thereby forming a first LC/HC dimer, which is the domain-exchanged LC/HC dimer comprising a $CH3_{LC}/CH3_{HC}$ domain pair; and b) one LC composed of VL-CL, and a HC composed of VH-CH1-CH2-CH3, wherein the VL-CH1 of the LC is dimerising with the VH-CL of the HC, thereby forming a second LC/HC dimer;

wherein the HC of the first LC/HC dimer is dimerising with the HC of the second LC/HC dimer, such as to form an Fc part comprising a $CH3_{HC}/CH3_{HC}$ domain pair.

Specifically, the $CH3_{LC}/CH3_{HC}$ domain pair and/or the $CH3_{HC}/CH3_{HC}$ domain pair may include one or two engineered CH3 domains to improve the production of the cognate pair, such as to reduce the likelihood of mismatching CH3 dimers when producing the molecule by a recombinant expression system.

Specifically, a Fab-like structure is obtained by dimerizing the heavy chain consisting of VH-$CH3_{HET}$ with the light chain consisting of VL-$CH3_{HET}$.

Specifically, a (Fab)$_2$-like structure is obtained by linking two Fab structures via the linkage of the two heavy chains, wherein one or both of the Fab structures are Fab-like structures.

According to another specific embodiment, the antibody is an IgM or IgE antibody, wherein the HC is composed of VH-CH3-CH2-CH3-CH4, optionally wherein the domains are directly linked or wherein the HC is further comprising one or more linker or hinge regions as a junction between antibody domains.

Specifically, the IgM-like structure is obtained by extending the (Fab)$_2$-like structure through fusion of an Fc part. Thereby, each of the heavy chains is C-terminally extended by a CH2-CH3-CH4 domain sequence.

Specifically, the linker or hinge region would provide for a junction between the C-terminal region of the $CH3_{HET}$ of the HC and the N-terminal region of the CH2 domain, thus, the antibody HC may comprise or consist of the following structure VH-CH3-junction-CH2-CH3.

The linkage of domains is specifically by recombinant fusion or chemical linkage. Specific linkage may be through linking the C-terminus of one domain to the N-terminus of another domain, e.g. wherein one or more amino acid residues in the terminal regions are deleted to shorten the domain size, or extended to increase flexibility of the domains.

Specifically, the shortened domain sequence comprises a deletion of the C-terminal and/or N-terminal region, such as to delete at least 1, 2, 3, 4, or 5, up to 6, 7, 8, 9, or 10 amino acids.

Specifically a linking sequence, such as a linker or a hinge region or at least part of the hinge region of an immunoglobulin, (linking sequences herein also referred to as "junction") may be used, such as including at least 1, 2, 3, 4, or 5 amino acids, up to 10, 15, or 20 amino acids. The domain extension by a linker may be through an amino acid sequence that originates from the N-, or C-terminal region of an immunoglobulin domain that would natively be positioned adjacent to the domain, such as to include the native junction between the domains. Alternatively, the linker may contain an amino acid sequence originating from the hinge region. However, the linker may as well be an artificial sequence, e.g. consisting of Gly or Ser amino acids.

Specifically, the junction between any of the VH or VL domains and the CH3 domains comprises an amino acid sequence, which is a) at least part of the junction between the CH2 and the CH3 domains of a human IgG antibody, and/or b) at least part of the junction between the VL and the CL domains of a human IgG antibody; and/or c) at least part of the junction between the VH and the CH1 domains of a human IgG antibody; and/or d) an artificial linking sequence with a length of 5 to 20 amino acids, preferably 8 to 15 amino acids.

According to a specific aspect, any of the $CH3_{HET}$ domains is of a human or humanized antibody, preferably of an IgG1 and comprising the amino acid sequence identified as SEQ ID 41, or a functional variant of such CH3 domain, preferably with at least 60% sequence identity to SEQ ID 41, preferably at least 70%, 80%, 90%, or 95% sequence identity.

Alternatively, the $CH3_{HET}$ domain is of any of a human or humanized IgG2, IgG3, IgG4, IgA, IgM, IgE, or IgD antibody, or a functional variant of such CH3 domain, preferably with at least 60% sequence identity to any of SEQ ID 42, 43, 44, 45, 46, 47, or 48, preferably at least 70%, 80%, 90%, or 95% sequence identity.

Specifically, any of the constant domains of the antibody, e.g. 1, 2, 3, 4, 5, 6, 7, 8, 9, 10, 11, 12, or all of the antibody domains, are of human origin or humanized or functionally active variants thereof with at least 60% sequence identity to the respective human antibody domains, e.g. of human IgG domains.

According to a specific embodiment, all domains comprised in the antibody are of human origin or humanized or functionally active variants thereof with at least 60% sequence identity, or at least 70%, 80%, 90%, or 95% sequence identity, preferably wherein the origin of the immunoglobulin domains is any of an IgG1, IgG2, IgG3, IgG4, IgM, or IgE antibody. Specifically, all immunoglobulin domains originate from the same type or subtype of immunoglobulin.

According to one aspect, the first and/or the second $CH3_{HET}$ domain originate from an IgG1 antibody.

Specifically, the first and/or the second $CH3_{HET}$ domain comprises the amino acid sequence identified as any of SEQ ID 41, which optionally comprises one or more point mutations, preferably 1, 2, 3, 4, 5, 6, 7, 8, 9, or 10 point mutations.

Specifically, the antibody comprises variable domains to establish two separate antigen-binding sites, e.g. by one Fab and one Fab-like structure, thereby providing for two Fv structures. Such construct comprises one Fab arm which comprises the wild-type structure, wherein VL-CL is dimerised with VH-CH1, and a second Fab-like arm which comprises the VL-$CH3_{LC}$ which is dimerised with VH-$CH3_{HC}$, thereby incorporating the $CH3_{LC}/CH3_{HC}$ domain pair into the antibody.

Specifically, the antibody is a bispecific antibody targeting two different antigens or two different epitopes of an antigen.

Specifically, the antibody is a bispecific antibody comprising a first LC paired with a first HC forming a first LC/HC dimer comprising a first binding site recognizing a first epitope, and a second LC paired with a second HC forming a second LC/HC dimer comprising a second binding site recognizing a second epitope which is different from the first epitope or originates from a different antigen, wherein either the first LC/HC dimer or the second LC/HC dimer is domain-exchanged.

Specifically, at least one of the CH3 domains of the $CH3_{LC}/CH3_{HC}$ domain pair is an engineered CH3 domain capable to produce a cognate pair of the $CH3_{LC}/CH3_{HC}$ domains.

Accordingly, the first and/or the second $CH3_{HET}$ domain may be an engineered CH3 domain capable to preferentially produce a cognate pair of $CH3_{HET}/CH3_{HET}$. Such cognate pair is specifically dimerizing with increased rate, affinity or avidity, as compared to a native (wild-type) CH3 pair. Specifically, the cognate pair is engineered in a way that the modified CH3 preferentially dimerises (pairs) with another matching modified CH3, and recognizes another (wild-type or non-matching) CH3 domain to a less extent.

According to a specific aspect, the antibody comprises a $CH3_{HC}/CH3_{HC}$ domain pair e.g. such as contained in a HC/HC dimer, wherein at least one of the CH3 domains is an engineered CH3 domain capable to produce a cognate pair of the $CH3_{HC}/CH3_{HC}$ domains.

Specifically, the $CH3_{LC}/CH3_{HC}$ domain pair is composed of wild-type human IgG1 CH3 domains comprising the amino acid sequence identified as SEQ ID 41 or a functional variant thereof, and at least one of the CH3 domains of the $CH3_{HC}/CH3_{HC}$ domain pair is an engineered CH3 domain capable to produce the cognate pair of the $CH3_Hc/CH3_Hc$ domains.

According to a specific embodiment, a) at least one of the CH3 domains of the $CH3_{LC}/CH3_{HC}$ domain pair is a first engineered CH3 domain capable to produce a cognate pair of the $CH3_{LC}/CH3_{HC}$ domains; and b) at least one of the CH3 domains of the $CH3_{HC}/CH3_{HC}$ domain pair is a second engineered CH3 domain capable to produce the cognate pair of the $CH3_Hc/CH3_Hc$ domains;

wherein the first and second engineered CH3 domains differ in at least one point mutation.

Specifically, the engineered CH3 domain, such as any of the $CH3_{LC}/CH3_{HC}$ domains, or $CH3_{HET}$ domains, or $CH3_{HC}/CH3_{HC}$ domains, e.g. a CH3 domain of a heterodimeric pair or homodimeric pair of CH3 domains, comprises the amino acid sequence identified as SEQ ID 41 or a functional variant thereof with at least 60% sequence identity to SEQ ID 41, which engineered CH3 domain comprises one or more of the following:

a) one or more knob or hole mutations, preferably any of T366Y/Y407'T, F405A/T394'W, T366Y:F405A/T394'W: Y407'T, T366W/Y407'A and S354C:T366W/Y349'C: T366'S:L368'A:Y407'V;

b) a cysteine residue that is covalently linked to a cysteine residue of the other cognate CH3 domain, thereby introducing an interdomain disulfide bridge, preferably linking the C-terminus of both CH3 domains;

c) SEED CH3 heterodimers that are composed of alternating segments of human IgA and IgG CH3 sequences; and/or d) one or more mutations where repulsive charge suppresses heterodimer formation, preferably any of: K409D/D399'K, K409D/D399'R, K409E/D399'K, K409E/D399'R, K409D:K392D/D399'K:E356'K or K409D:K392D:K370D/D399'K:E356'K:E357'K; and/or e) one or more mutations selected for heterodimer formation and/or thermostability, preferably any of:
T350V:L351Y:F405A:Y407V/T350V:T366L:K392L:T394W,
T350V:L351Y:F405A:Y407V/T350V:T366L:K392M:T394W,
L351Y:F405A:Y407V/T366L:K392M:T394W,
F405A:Y407V/T366L:K392M:T394W, or
F405A:Y407V/T366L:T394W, wherein numbering is according to the EU index of Kabat.

In the specification of the point mutations described herein, the "slash" differentiates the point mutations on one chain or one domain from the point mutations from the other chain or other domain of the respective pair; the "indent" in the amino acid position numbering signifies the second chain or dimer of the heterodimer. The "colon" identifies the combination of point mutations on one of the chains or domains, respectively.

Any of the mutations selected for heterodimer formation and/or thermostability as mentioned above or further mutations in accordance with the disclosure of Von Kreudenstein et al. [8] can be used.

Preferably, either (i) a knob; or (ii) a hole mutation, or (iii) a knob and hole mutation, is engineered on one chain or domain, and the counterpart (i) hole, or (ii) knob mutation, or (iii) hole and knob mutation, is engineered on the other chain of the heterodimer.

Specifically, a pair of CH3 domains comprising one or two engineered CH3 domains may comprise more than one (additional) interdomain disulfide briges, e.g. 2, or 3, connecting the pair of two CH3 domains.

Specifically, different mutations (according to a) above) are engineered in both CH3 domains of a respective pair of CH3 domains to produce a matching pair, wherein one domain comprises a steric modification of a contact surface in the beta-sheet region that is preferentially attached to the respective contact surface of the other domain through the complementary steric modification. Such steric modifications mainly result from the different amino acid residues and side chains, e.g. to produce a "knob" or "hole" structure, which are complementary to form a "knob into hole" dimer.

According to a specific aspect, each of a first and a second CH3 domains of a pair of CH3 domains, e.g. the $CH3_{LC}/CH3_{HC}$, or the first and the second $CH3_{HET}$ domains, or the $CH3_{HC}/CH3_{HC}$ domains, is of the IgG type with the amino acid sequence identified as SEQ ID 41 or a functional variant of SEQ ID 41, which is engineered to obtain a strand-exchange by incorporating at least one beta strand IgA segment of at least 2 amino acids length, and which comprises a cognate pair of CH3 domains through pairing an IgA segment of the first CH3 domain with an IgA segment of the second CH3 domain. Such strand-exchanged CH3 domains specifically may comprise alternating segments of IgA and IgG amino acid sequences, e.g. incorporating at least 1, 2, 3, 4, or 5 different IgA segments, each located at different positions and separated from each other by a non-IgA segment, e.g. IgG segments.

According to a specific aspect, the antibody is an effector-function competent antibody comprising a Fc gamma receptor binding site and/or a C1q binding site located in any of the CH2 and/or CH3 domains.

Specifically, the antibody is effector competent which comprises an Fcγ receptor binding site in the HC and optionally in the Fc region.

Specifically, the antibody is characterized by any of an ADCC and/or CDC activity.

According to another specific aspect, the antibody is an effector-negative (EN) antibody comprising a Fc region deficient in binding to an Fc gamma receptor and/or C1q.

Specifically, the effector-negative antibody is characterized by a human IgG2 CH2 sequence, or an engineered variant thereof, comprising a modified human IgG2 CH2 domain (F296A, N297Q) described in U.S. Pat. No. 8,562,986, fused to the N-terminus of the C-terminal CH3 domain, e.g. as used in "VH(1)-CH3_KNOB (T366Y)-CH2$_{EN}$-CH3$_{AG}$" (SEQ ID 15).

Specifically, when used to form an effector-negative Fc region without any binding domain, as used to comprise one chain in the monovalent effector-negative antibodies, the effector-negative Fc region was comprising a modified human IgG1 hinge (C220S) and modified human IgG2 CH2 domain (F296A, N297Q) described in U.S. Pat. No. 8,562,986 fused to the N-terminus of the C-terminal CH3 domain, e.g. as used in "huFc_g1hingeEN-CH2$_{EN}$-CH3$_{GA}$" (SEQ ID 16).

Specifically, the antibody is effector deficient (herein also referred to as effector negative), with substantially reduced or no binding to an Fcγ receptor or CD16a via the Fc region.

Specifically, the antibody has a substantially reduced or no ADCC and/or CDC.

Specifically, the antibody comprises an Fc part of an antibody which comprises an FcRn binding site at the interjunction of the CH2 with the CH3 domain, and/or an Fc gamma receptor binding site within the N-terminal region of the CH2 domain, and/or a C1q binding site within the N-terminal region of the CH2 domain.

According to a specific aspect, the antibody comprises a pH-dependent FcRn binding site located in any of the CH2 and/or CH3 domains. Specifically, the FcRn binding site has an affinity to bind the FcRn with a Kd of less than $10^{-4}$ M, or less than $10^{-5}$M, $10^{-6}$M, $10^{-7}$M, or $10^{-8}$M in a pH-dependent manner.

Specifically, the binding affinity to bind FcRn in a pH dependent way is at least 1-log, preferably at least 2-log or 3-log increased at pH5-6 as compared to the same binding affinity at physiological pH (pH7.4).

According to a further aspect, the antibody is engineered to alter the pH dependent FcRn binding. For example, at least one of the CH3 domains of the $CH3_{LC}/CH3_{HC}$ domain pair can be engineered to comprise at least one mutation at the FcRn binding site to reduce pH-dependent FcRn binding, specifically at least one of the H433A or H435A mutations, or both H433A and H435A mutations, wherein the numbering is according to the EU index of Kabat. Reduction of pH-dependent FcRn binding may be such that the binding affinity to bind FcRn in a pH dependent way is less than 1-log, preferably about the same or less at pH5-6 as compared to the same binding affinity at physiological pH (pH7.4).

By such modulation of FcRn binding, antibodies may be provided which comprise only the FcRn binding site of a (wild-type) Fc fragment located between the C-terminal CH2 and CH3 domains interface.

A specific embodiment of $CH3_{LC}$ and $CH3_{HC}$ variants without the native CH3 domain pH-dependent FcRn binding site is obtained by introduction of H433A and H435A mutations (numbering according to EU index of Kabat), which is part of the pH-dependent FcRn binding site contributed from the native CH3 domain sequence [9], sequences see FIG. 22.

According to a specific aspect, the antibody is any of a) a bispecific antibody specifically recognizing a first and a second target, which comprises a first pair of heavy and light chains (H1/L1) incorporating the binding site recognizing the first target, and a second pair of heavy and light chains (H2/L2) incorporating the binding site recognizing the second target; or b) a one-armed antibody specifically recognizing a target by a monovalent binding site, which comprises a pair of heavy and light chains (H1/L1) incorporating the binding site recognizing the target, wherein the heavy chain (H1) is bound to another heavy chain (H2) composed of a constant region, thereby forming an Fc region. Specifically, the one-armed antibody comprises a H2, which is a Fc chain comprising CH2-CH3 antibody domains. The one-armed antibody is specifically characterized by the Fc region composed of a CH2-CH3 dimer (either homodimer or heterodimer). Specifically, the Fc region is characterized by a $CH3_{HC}/CH3_{HC}$ dimer.

In particular, any of the bispecifc antibodies or one-armed antibodies is characterized by monovalent binding of the respective target. Therefore, each of the bispecifc antibodies or one-armed antibodies is specifically characterized by only one binding site per target. For example, the bispecific antibody comprises only one binding site recognizing a first target, and only one binding site recognizing a second target. Specifically, the one-armed antibody comprises only one binding site recognizing the target.

Specifically, the antibody is a bispecific antibody, wherein the first target is CD3 or CD16, and the second target is EGFR.

Specifically, the antibody is a one-armed antibody, wherein the target is EGFR.

Specifically, the antibody is a one-armed antibody, wherein the target is CD3.

Specifically, the antibody is a one-armed antibody, wherein the target is CD16.

Specific embodiments refer to any of the antibodies exemplified herein, or comprising any of the heavy and light chains or any of the pairs of heavy and light chains described in the Examples section. Specifically, an antibody as described herein may comprise or consist of the heavy and light chains described in the Examples section.

Specifically, the antibody is provided for medical, diagnostic or analytical use.

The invention further provides for a pharmaceutical preparation comprising the antibody of the invention, preferably comprising a parenteral or mucosal formulation, optionally containing a pharmaceutically acceptable carrier or excipient.

The invention further provides for an isolated nucleic acid encoding an antibody of the invention.

The invention further provides for an expression cassette or a plasmid comprising the nucleic acid of the invention and optionally further sequences to express the antibody encoded by the nucleic acid sequence, such as regulatory sequences.

Specifically, the expression cassette or the plasmid comprises a coding sequence to express the HC and/or LC or more than one HC and/or more than one LC of an antibody of the invention. For example, the antibody may comprise two different HC and two different LC, and the coding sequences for two different HC and two different LC are employed to produce a heterodimeric antibody.

The invention further provides for a production host cell comprising at least one expression cassette or a plasmid incorporating one or more nucleic acid molecules encoding an antibody of the invention and optionally further sequences to express the immunoglobulin.

The invention further provides for a method of producing an antibody according to the invention, wherein a host cell according to the invention is cultivated or maintained under conditions to produce said antibody.

FIGURES

FIG. 1:

FIG. 1A: Schematic illustration of domain-exchanged bispecific antibodies with CH3 domain exchange in one of the Fab arms and SEED technology (GA/AG) in the C-terminal CH3 domains (i.e. the $CH3_{HC}/CH3_{HC}$ domain pair). The C-terminal GA SEED domain is shown fused to the native Fab domain and the C-terminal AG SEED domain is shown fused to the CH3 domain-exchanged Fab. However the native or CH3 domain-exchanged Fabs can be fused to either C-terminal SEED domain, so the relative orientation of Fabs between the $CH3_{HC}/CH3_{HC}$ domain pair could also be reversed (not illustrated here).

1A-1: SEED technology in C-terminal CH3 domain paired with CH3 Knobs-into-holes domain-exchanged Fab comprised of Knob in the heavy chain and Hole in the light chain elements of the Fab. 1A-2: Equivalent to (1A-1) example, but with domain-exchanged Fab comprised of Hole in the heavy chain and Knob in the light chain elements of the Fab. 1A-3: SEED technology in C-terminal CH3 domain paired with CH3 domain-exchanged Fab comprised of "electrostatic steering" [7] positive charge variants in the heavy chain and negative charge variants in the light chain elements of the Fab. 1A-4: Equivalent to (1A-3) example, but with domain-exchanged Fab comprised of "electrostatic steering" [7] negative charge variants in the heavy chain and positive charge variants in the light chain elements of the Fab. 1A-5: SEED technology in C-terminal CH3 domain paired with CH3 domain-exchanged Fab comprised of "Chain A" [8] variants in the heavy chain and "Chain B" variants in the light chain elements of the Fab. 1A-6: Equivalent to (1A-5) example, but with domain-exchanged Fab comprised of "Chain B" [8] variants in the heavy chain and "Chain A" variants in the light chain elements of the Fab. 1A-7: SEED technology in C-terminal CH3 domain paired with CH3 domain-exchanged Fab comprised of "AG" SEED [2] variants in the heavy chain and "GA" SEED variants in the light chain elements of the Fab. 1A-8: Equivalent to (1A-7) example, but with domain-exchanged Fab comprised of "GA" SEED [2] variants in the heavy chain and "AG" SEED variants in the light chain elements of the Fab.

Figure 1B:
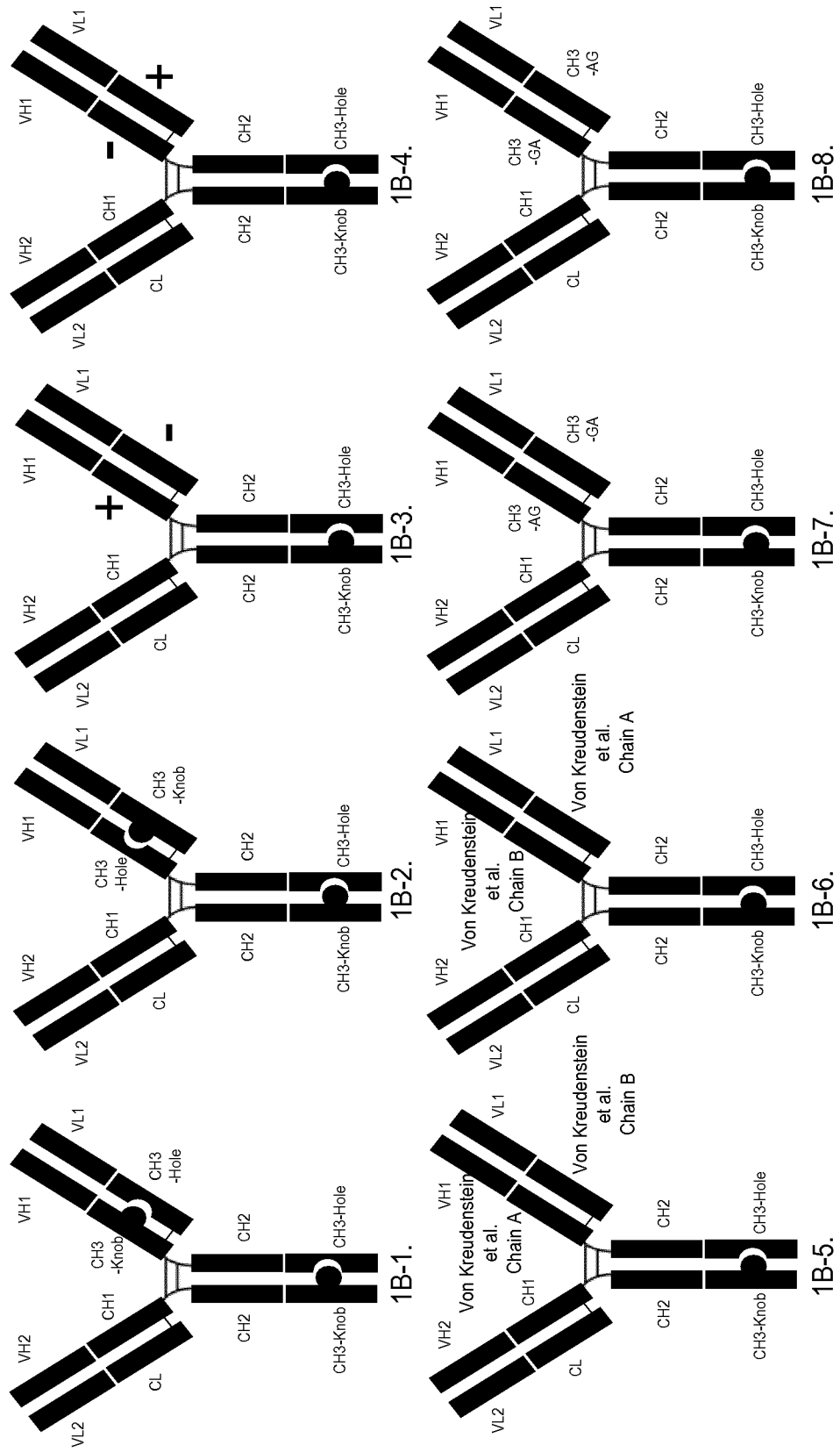

FIG. 1B: Schematic illustration of domain-exchanged bispecific antibodies with CH3 domain exchange in one of the Fab arms and Knobs-into-Holes (KiH) technology in the C-terminal CH3 domains (i.e. the $CH3_{HC}/CH3_{HC}$ domain pair). The C-terminal "Knob" domain is shown fused to the native Fab domain and the C-terminal "Hole" domain is shown fused to the CH3 domain-exchanged Fab. However the native or CH3 domain-exchanged Fabs can be fused to either C-terminal "Knob" or "Hole" domains, so the relative orientation of Fabs between the $CH3_{HC}/CH3_{HC}$ domain pair could also be reversed (not illustrated here).

1B-1: Knobs-into-Holes technology in C-terminal CH3 domain paired with CH3 Knobs-into-holes domain-exchanged Fab comprised of Knob in the heavy chain and Hole in the light chain elements of the Fab. 1B-2: Equivalent to (1B-1) example, but with domain-exchanged Fab comprised of Hole in the heavy chain and Knob in the light chain elements of the Fab. 1B-3: Knobs-into-Holes technology in C-terminal CH3 domain paired with CH3 domain-exchanged Fab comprised of "electrostatic steering" [7] positive charge variants in the heavy chain and negative charge variants in the light chain elements of the Fab. 1B-4: Equivalent to (1B-3) example, but with domain-exchanged Fab comprised of "electrostatic steering" [7] negative charge variants in the heavy chain and positive charge variants in the light chain elements of the Fab. 1B-5: Knobs-into-Holes technology in C-terminal CH3 domain paired with CH3 domain-exchanged Fab comprised of "Chain A" [8] variants in the heavy chain and "Chain B" variants in the light chain elements of the Fab. 1B-6: Equivalent to (1B-5) example, but with domain-exchanged Fab comprised of "Chain B" [8] variants in the heavy chain and "Chain A" variants in the light chain elements of the Fab. 1B-7: Knobs-into-Holes technology in C-terminal CH3 domain paired with CH3 domain-exchanged Fab comprised of "AG" SEED [2] variants in the heavy chain and "GA" SEED variants in the light chain elements of the Fab. 1B-8: Equivalent to (1B-7) example, but with domain-exchanged Fab comprised of "GA" SEED [2] variants in the heavy chain and "AG" SEED variants in the light chain elements of the Fab.

Figure 1C:
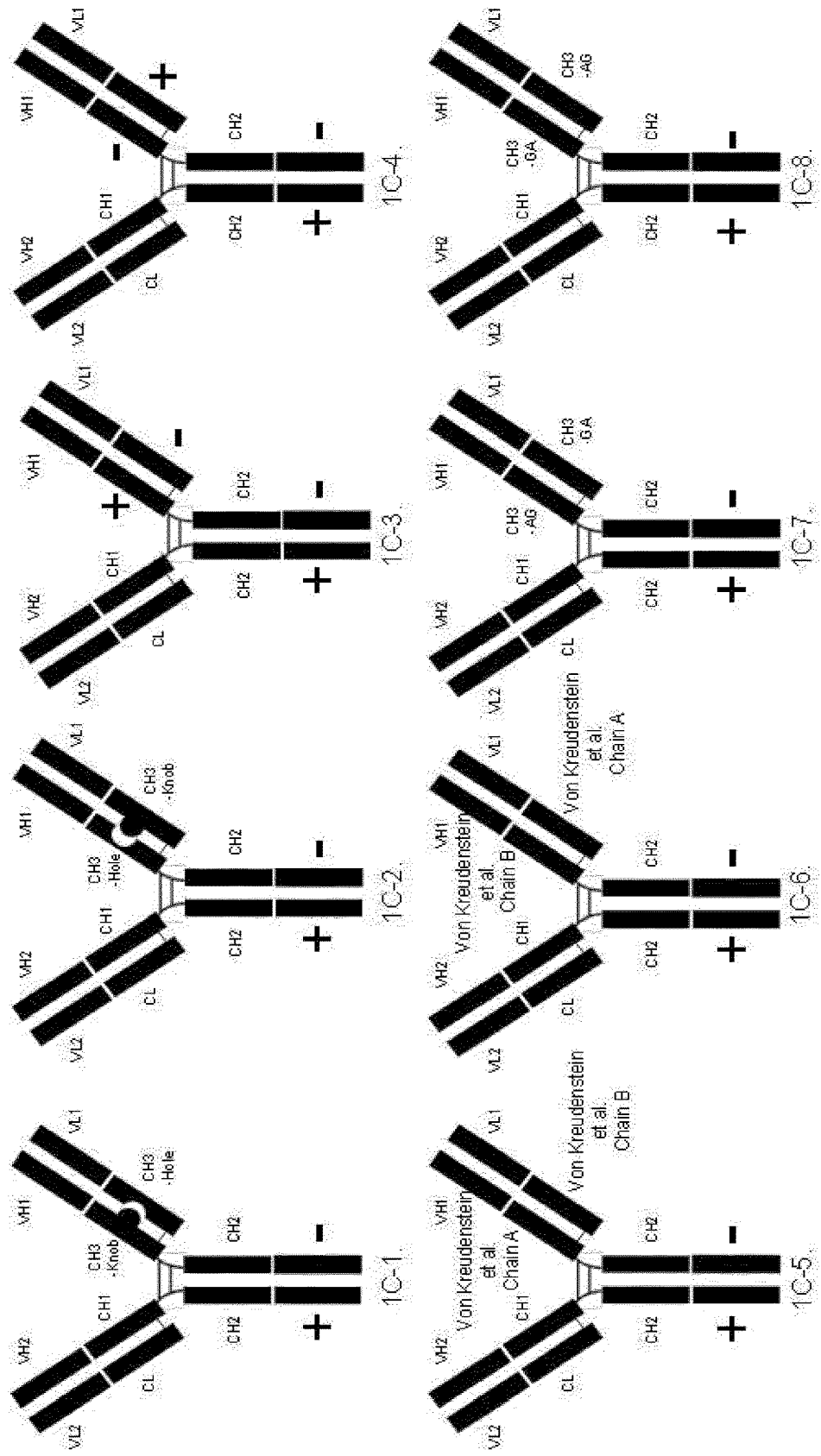

FIG. 1C: Schematic illustration of domain-exchanged bispecific antibodies with CH3 domain exchange in one of the Fab arms and Electrostatic Steering (Ref. 7) technology in the C-terminal CH3 domains (i.e. the $CH3_{HC}/CH3_{HC}$ domain pair). The C-terminal Electrostatic Steering [7] positive charge variant domain is shown fused to the native Fab domain and the C-terminal negative charge variant domain is shown fused to the CH3 domain-exchanged Fab. However the native or CH3 domain-exchanged Fabs can be fused to either C-terminal positive or negative charge variant domains, so the relative orientation of Fabs between the $CH3_{HC}/CH3_{HC}$ domain pair could also be reversed (not illustrated here).

1C-1: Electrostatic Steering technology in C-terminal CH3 domain paired with CH3 Knobs-into-holes domain-exchanged Fab comprised of Knob in the heavy chain and Hole in the light chain elements of the Fab. 1C-2: Equivalent to (1C-1) example, but with domain-exchanged Fab comprised of Hole in the heavy chain and Knob in the light chain elements of the Fab. 1C-3: Electrostatic Steering technology in C-terminal CH3 domain paired with CH3 domain-exchanged Fab comprised of "electrostatic steering" [7] positive charge variants in the heavy chain and negative charge variants in the light chain elements of the Fab. 1C-4: Equivalent to (1C-3) example, but with domain-exchanged Fab comprised of "electrostatic steering" [7] negative charge variants in the heavy chain and positive charge variants in the light chain elements of the Fab. 1C-5: Electrostatic Steering technology in C-terminal CH3 domain paired with CH3 domain-exchanged Fab comprised of "Chain A" [8] variants in the heavy chain and "Chain B" variants in the light chain elements of the Fab. 1C-6: Equivalent to (1C-5) example, but with domain-exchanged Fab comprised of "Chain B" [8] variants in the heavy chain and "Chain A" variants in the light chain elements of the Fab. 1C-7: Electrostatic Steering technology in C-terminal CH3 domain paired with CH3 domain-exchanged Fab comprised of "AG" SEED [2] variants in the heavy chain and "GA" SEED variants in the light chain elements of the Fab. 1C-8: Equivalent to (1C-7) example, but with domain-exchanged Fab comprised of "GA" SEED [2] variants in the heavy chain and "AG" SEED variants in the light chain elements of the Fab.

Figure 1D:
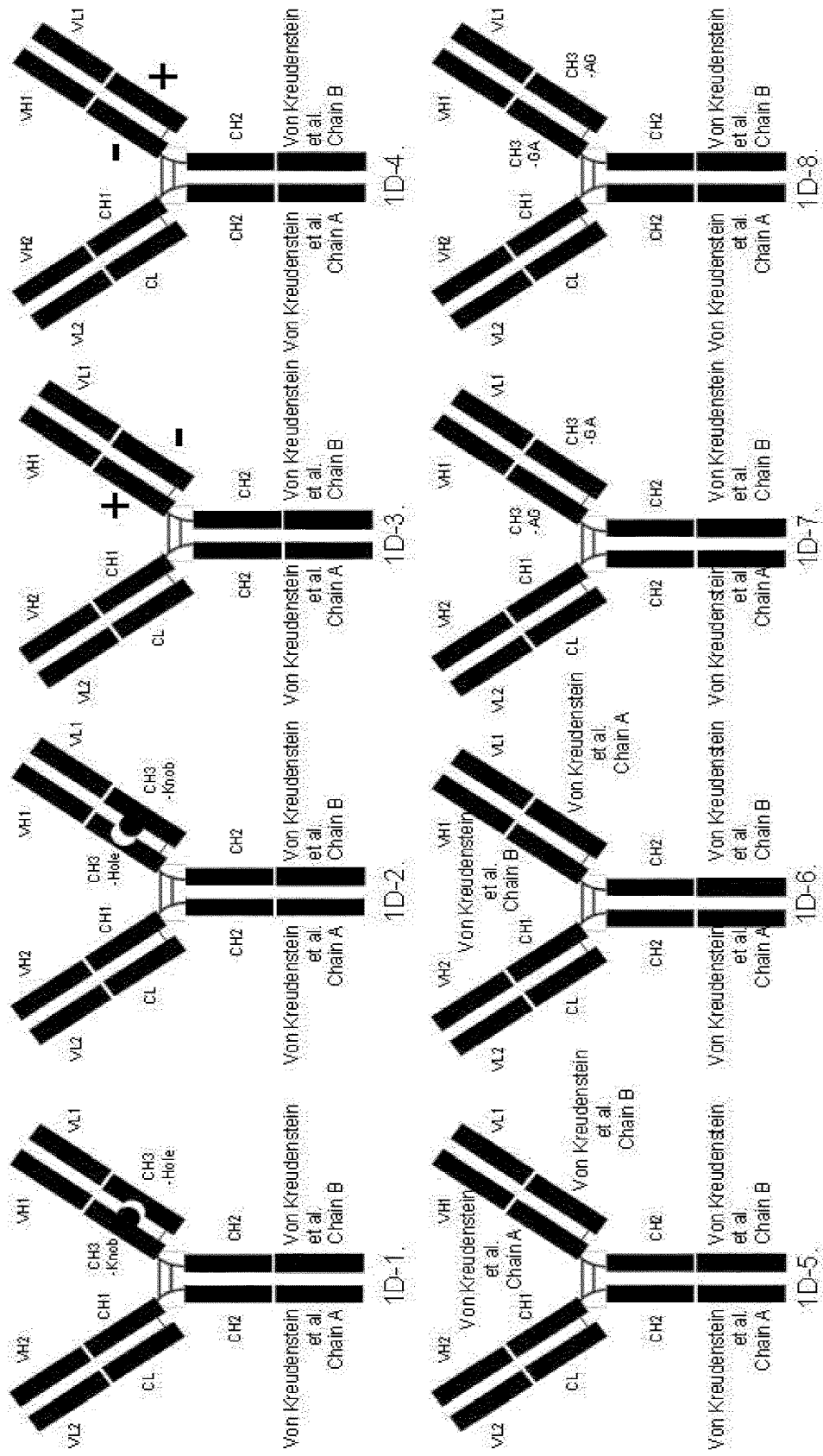

FIG. 1D: Schematic illustration of domain-exchanged bispecific antibodies with CH3 domain exchange in one of the Fab arms and engineered "Chain A" and "Chain B" variant domains (Von Kreudenstein Ref. 8) technology in the C-terminal CH3 domains (i.e. the $CH3_{HC}/CH3_{HC}$ domain pair). The C-terminal Chain A [8] variant domain is shown fused to the native Fab domain and the C-terminal Chain B [8] variant domain is shown fused to the CH3 domain-exchanged Fab. However the native or CH3 domain-exchanged Fabs can be fused to either C-terminal Chain A or Chain B variant domains, so the relative orientation of Fabs between the $CH3_{HC}/CH3_{HC}$ domain pair could also be reversed (not illustrated here).

1D-1: Chain A and Chain B variant domains technology [8] in C-terminal CH3 domains paired with CH3 Knobs-into-holes domain-exchanged Fab comprised of Knob in the heavy chain and Hole in the light chain elements of the Fab. 1D-2: Equivalent to (1D-1) example, but with domain-exchanged Fab comprised of Hole in the heavy chain and Knob in the light chain elements of the Fab. 1D-3: Chain A and Chain B variant domains technology [8] in C-terminal CH3 domain paired with CH3 domain-exchanged Fab comprised of "electrostatic steering" [7] positive charge variants in the heavy chain and negative charge variants in the light chain elements of the Fab. 1D-4: Equivalent to (1D-3) example, but with domain-exchanged Fab comprised of "electrostatic steering" [7] negative charge variants in the heavy chain and positive charge variants in the light chain elements of the Fab. 1D-5: Chain A and Chain B variant domains technology [8] in C-terminal CH3 domain paired with CH3 domain-exchanged Fab comprised of "Chain A" [8] variants in the heavy chain and "Chain B" variants in the light chain elements of the Fab. 1D-6: Equivalent to (1D-5) example, but with domain-exchanged Fab comprised of "Chain B" (Ref. 8) variants in the heavy chain and "Chain A" variants in the light chain elements of the Fab. 1D-7: Chain A and Chain B variant domains technology [8] in C-terminal CH3 domain paired with CH3 domain-exchanged Fab comprised of "AG" SEED [2] variants in the heavy chain and "GA" SEED variants in the light chain elements of the Fab. 1D-8: Equivalent to (1D-7) example, but with domain-exchanged Fab comprised of "GA" SEED [2] variants in the heavy chain and "AG" SEED variants in the light chain elements of the Fab.

Figure 2A:
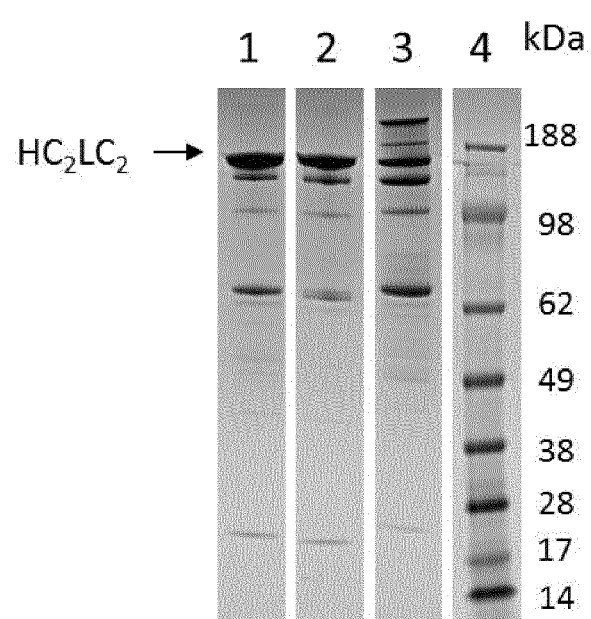

FIG. 2:

FIG. 2A: Characterization of domain-exchanged heterodimeric bispecific antibodies by non-reducing SDS-PAGE. SDS-PAGE was stained with Colloidal Blue Stain Kit (Invitrogen). Lane 1: non-reduced domain-exchanged heterodimeric bispecific antibody 1(Fab domain-exchange on the $CH3_{AG}$-heavy chain). Lane 2: non-reduced domain-exchanged heterodimeric bispecific antibody 2 (Fab domain-exchange on the $CH3_{GA}$-heavy chain). Lane 3: non-reduced domain-exchanged heterodimeric bispecific antibody 3 (containing CH3 wt domain-exchanged Fab arm on the $CH3_{GA}$-heavy chain). Lane 4: protein standard SeeBlue Plus 2 Pre-Stained Molecular Weight Marker (Invitrogen).

Figure 2B:
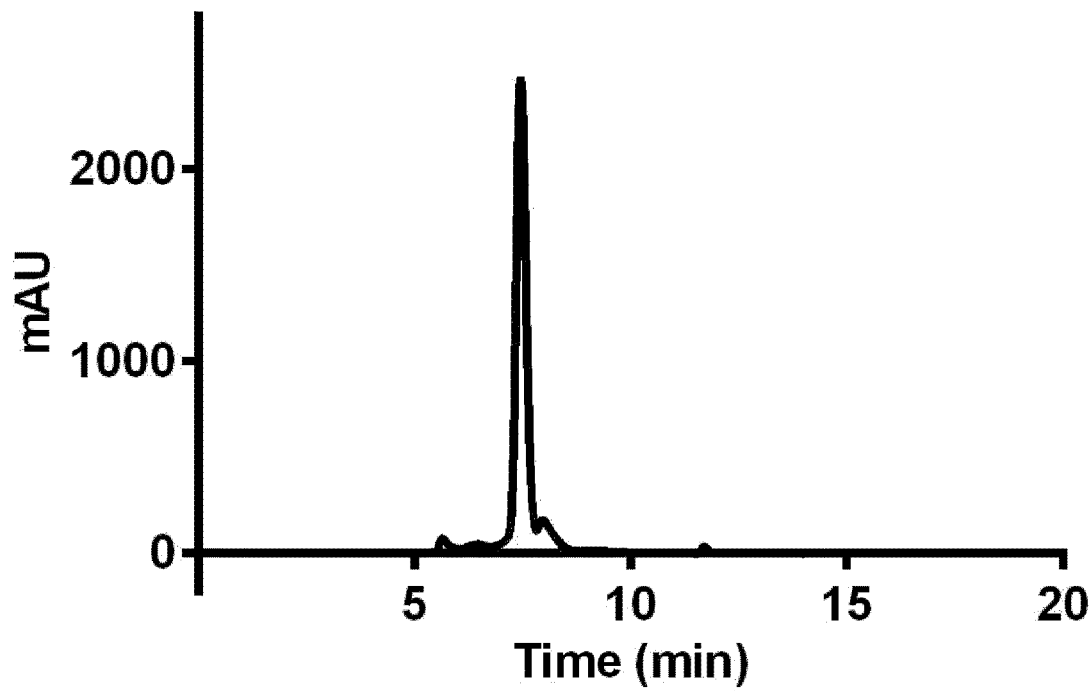

FIG. 2B: SEC profile of the domain-exchanged heterodimeric bispecific antibody 1 (see Examples 1 and 2).

Figure 2C:
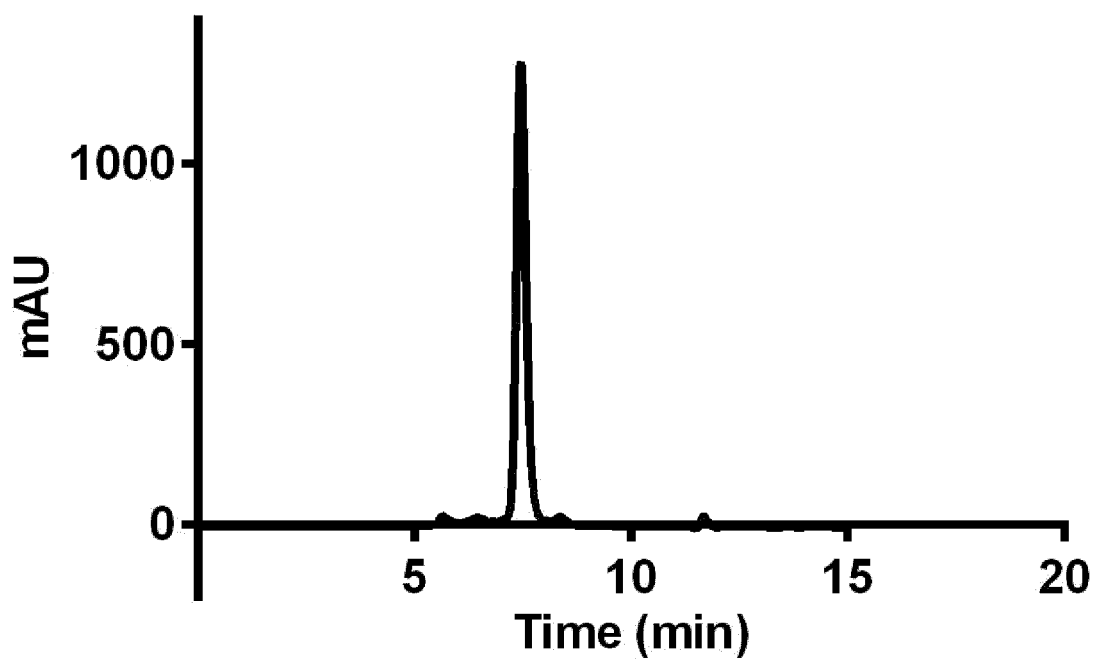

FIG. 2C: SEC profile of the domain-exchanged heterodimeric bispecific antibody 2 (see Examples 1 and 2).

Figure 2D:
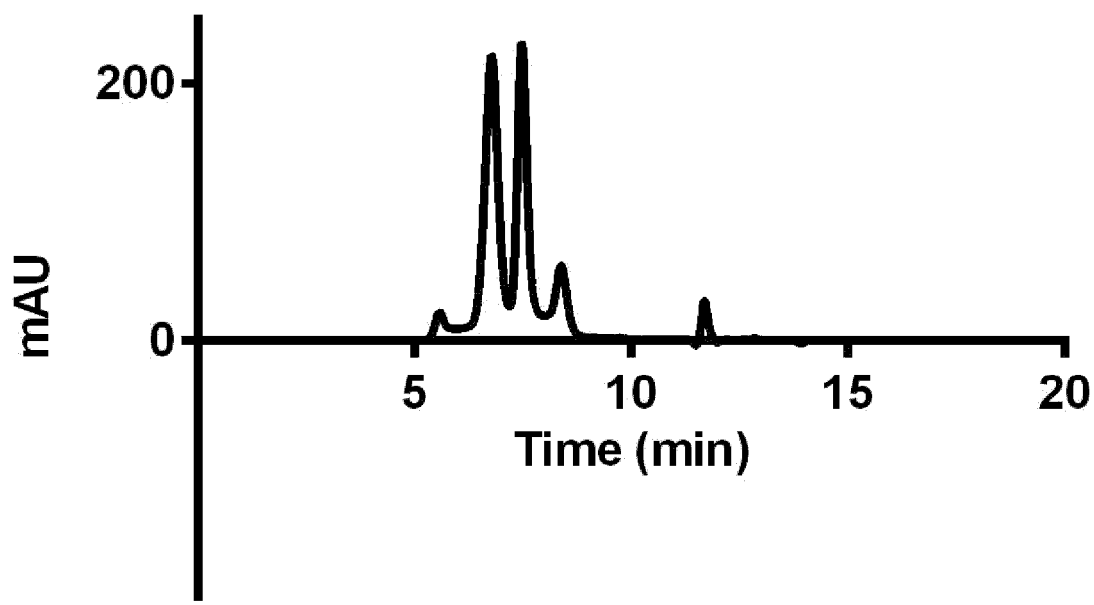

FIG. 2D: SEC profile of the domain-exchanged heterodimeric bispecific antibody 3 (see Examples 1 and 2).

Figure 3A:
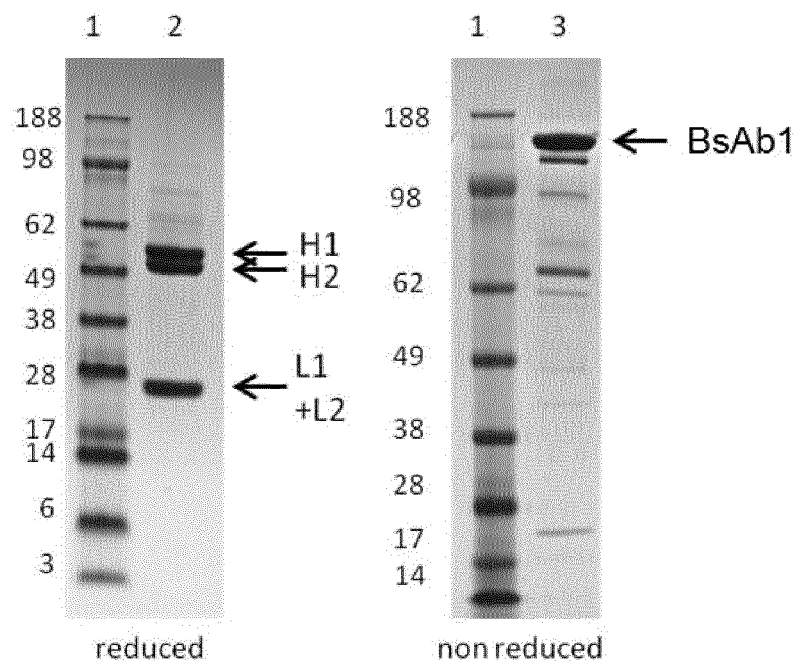

FIG. 3:

FIG. 3A: Characterization of the domain-exchanged bispecific antibody 1 (BsAb1) by SDS-PAGE under reducing or non-reducing conditions. SDS-PAGE was stained with Colloidal Blue Stain Kit (Invitrogen). Lane 1: Protein standard SeeBlue Plus 2 Pre-Stained Molecular Weight Marker (Invitrogen). Lane 2: Reduced SDS-PAGE profile shows H1 band corresponding to VH(1)-CH3_KNOB (T366Y)-CH2-$CH3_{AG}$ (SEQ ID 2), H2 band that corresponds to VH(2)-CH1-CH2-$CH3_{GA}$ (SEQ ID 4) and L1+L2 band that corresponds to VL(1)-CH3_HOLE (Y407T) (SEQ ID 1) and VL(2)-CL (SEQ ID 3). Lane 3: Non-reduced SDS-PAGE profile shows main band bispecific antibody corresponding to the domain-exchanged bispecific antibody BsAb1.

Figure 3B:
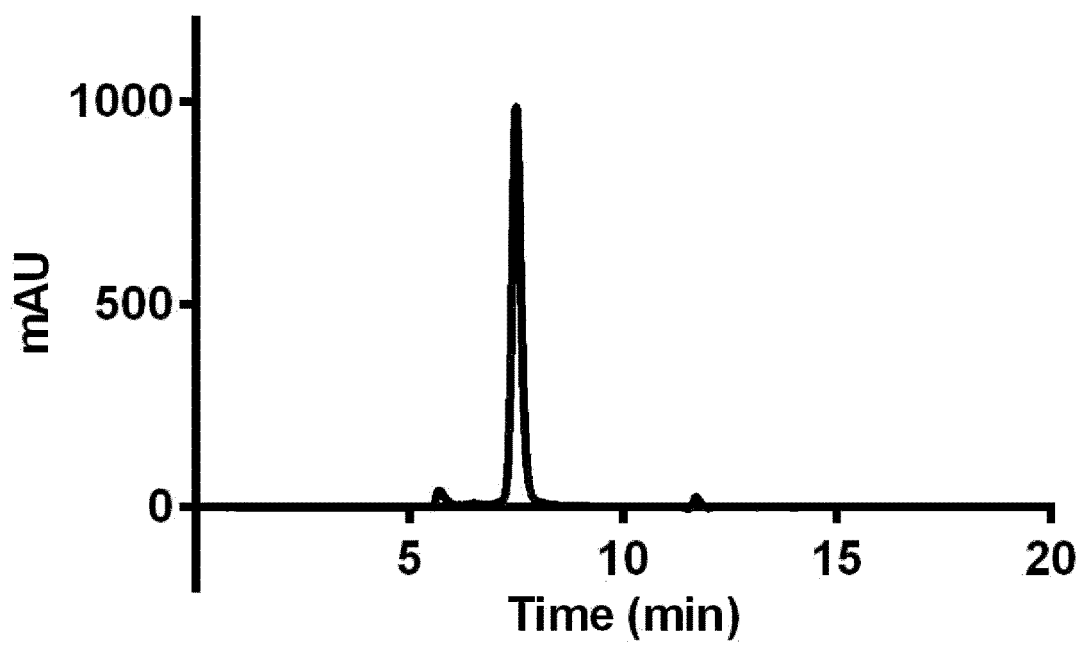

FIG. 3B: SEC profile of the domain-exchanged bispecific antibody BsAb1.

Figure 4:
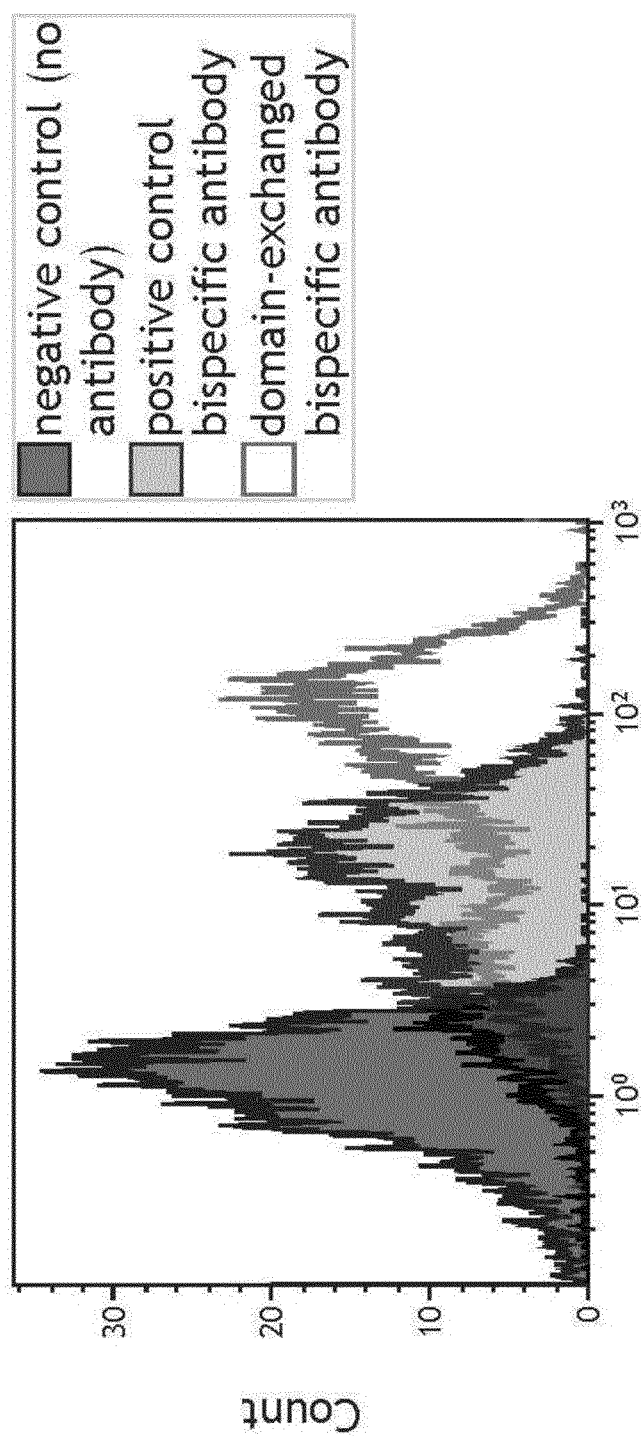

FIG. 4: FACS analysis of domain-exchanged bispecific antibody BsAb1.

Figure 5:
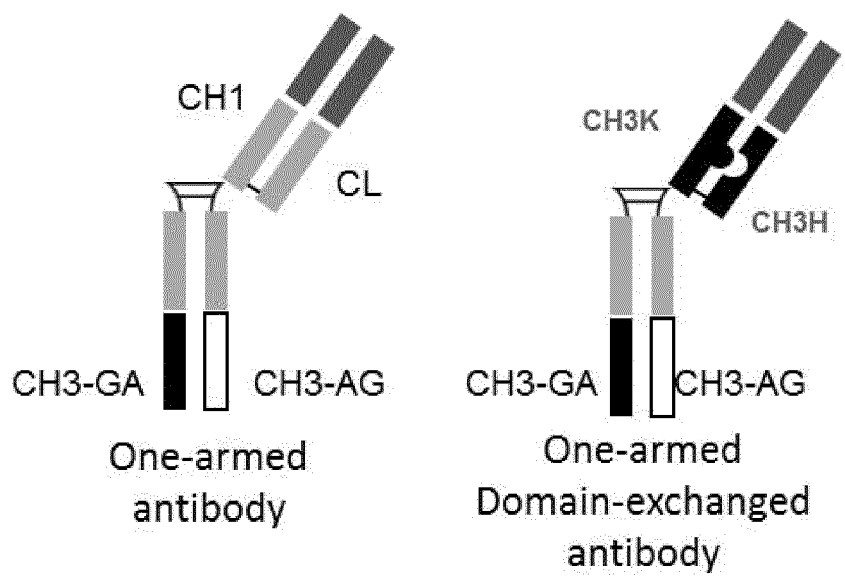

FIG. 5: Schematic illustration of one-armed antibodies, either containing the unengineered Fab domain or the CH3 domain exchange in the Fab arm fused to the SEED AG domain.

Figure 6A:
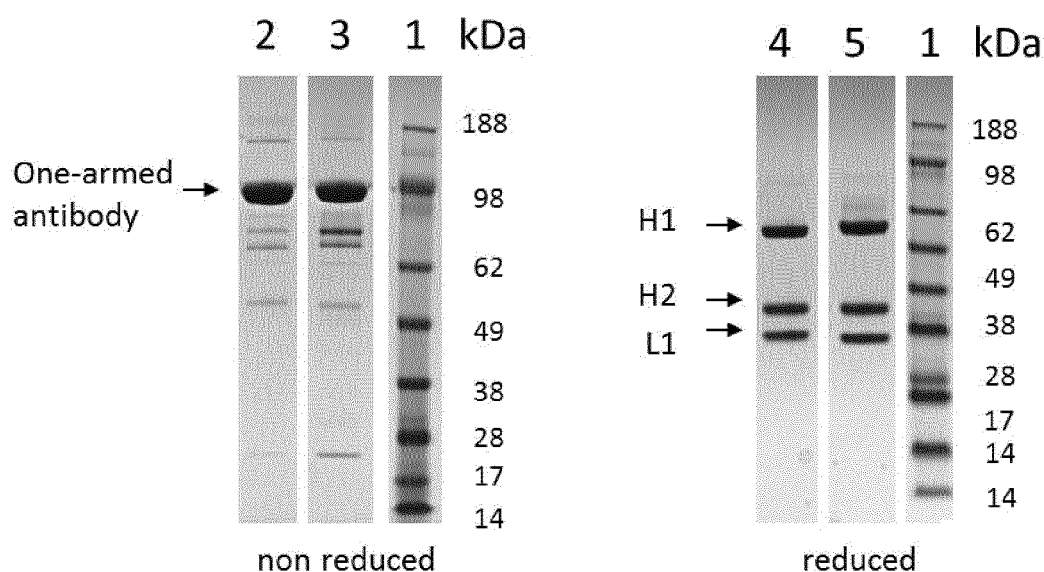

FIG. 6:

FIG. 6A: Characterization of one-armed antibodies, either containing the unengineered Fab domain or the CH3 domain-exchanged Fab, by SDS-PAGE under non-reducing and reducing conditions. SDS-PAGE was stained with Colloidal Blue Stain Kit (Invitrogen). Lane 1: protein standard SeeBlue Plus 2 Pre-Stained Molecular Weight Marker (Invitrogen). Lane 2: Non-reduced profile shows main band one-armed antibody corresponding to the unengineered antibody (CH1/CL Fab). Lane 3: Non-reduced profile shows main band one-armed antibody corresponding to the domain-exchanged Fab antibody. Lane 4: Reduced profile shows H1 band corresponding to VH(1)-CH1-CH2-$CH3_{AG}$ (SEQ ID 11), H2 band that corresponds to huFc-GA SEED (SEQ ID 9) and L1 band that corresponds to VL(1)-CL (SEQ ID 10). Lane 5: Reduced profile shows H1 band corresponding to VH(1)-CH3_KNOB (T366Y)-CH2-$CH3_{AG}$ (SEQ ID 2), H2 band that corresponds to huFc-GA SEED (SEQ ID 9) and L1 band that corresponds to VL(1)-CH3_HOLE (Y407T) (SEQ ID 1).

Figure 6B:
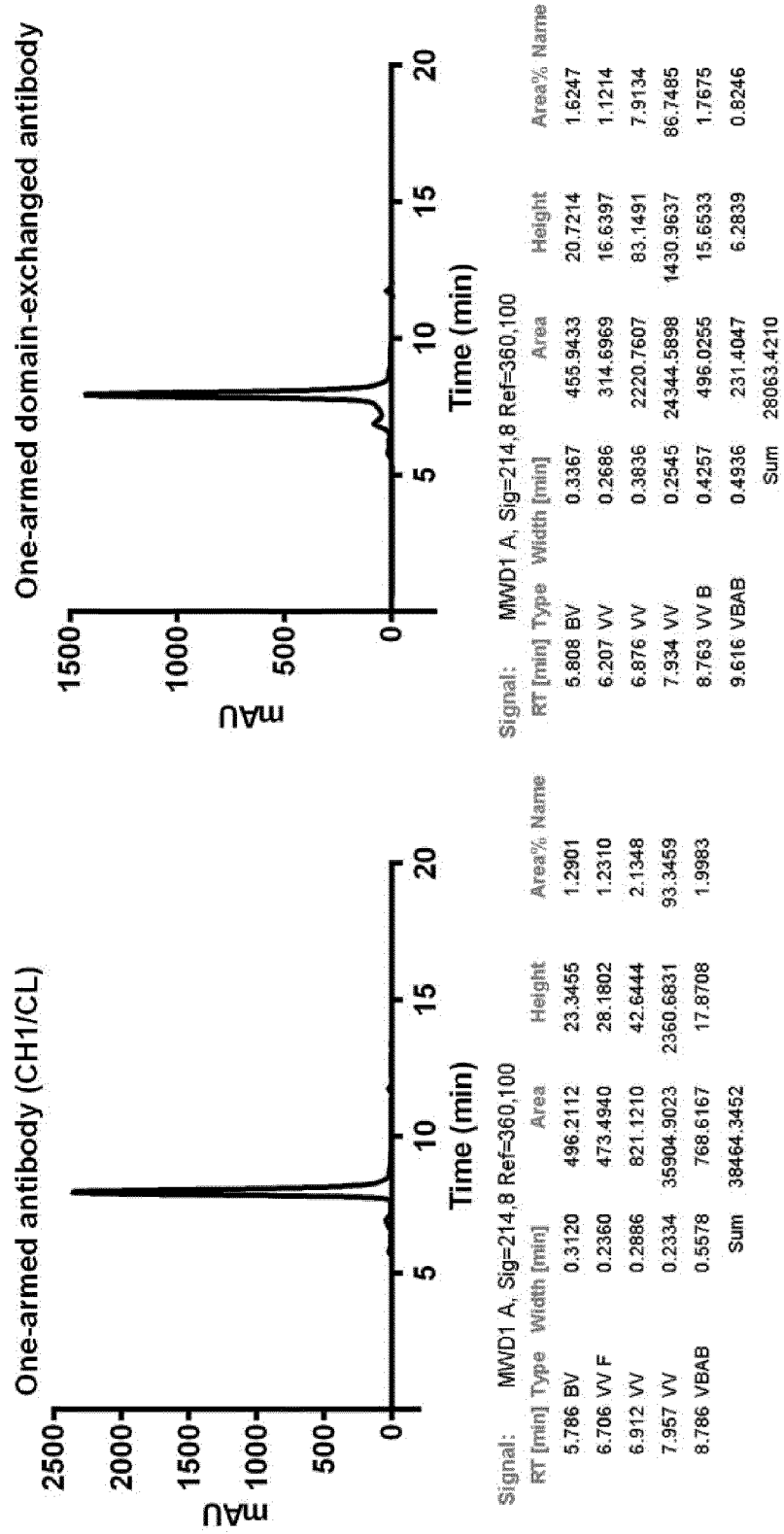

FIG. 6B: SEC profile of one-armed antibodies containing unengineered CH1/CL domains in the Fab or domain-exchanged Fab using CH3-KiH cognate domain pair in the Fab arm (see Example 6).

Figure 7:
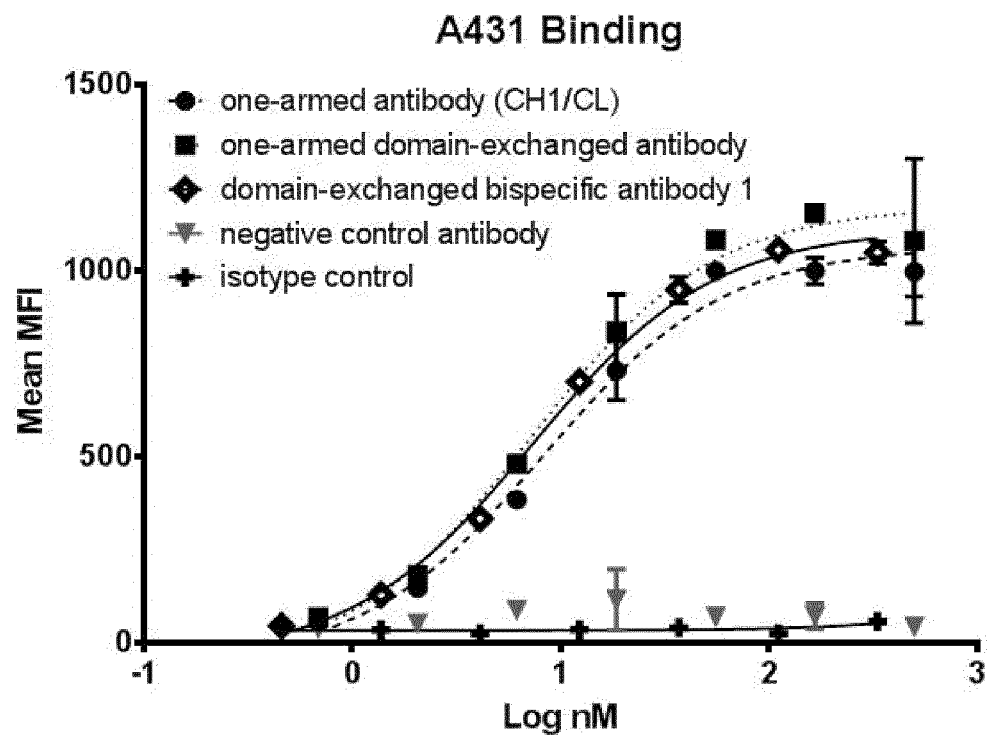

FIG. 7: Antigen binding of one-armed antibodies (unengineered Fab and domain-exchanged Fab) and BsAb1 to EGFR-positive cells (A431 cells). Cell binding was measured by flow cytometry. The antibodies were tested in serial dilutions (1:3) and binding was detected using an anti-human Fc F(ab)2 secondary antibody conjugated with phycoerythrin. Measurements were performed in duplicates.

Figure 8A:
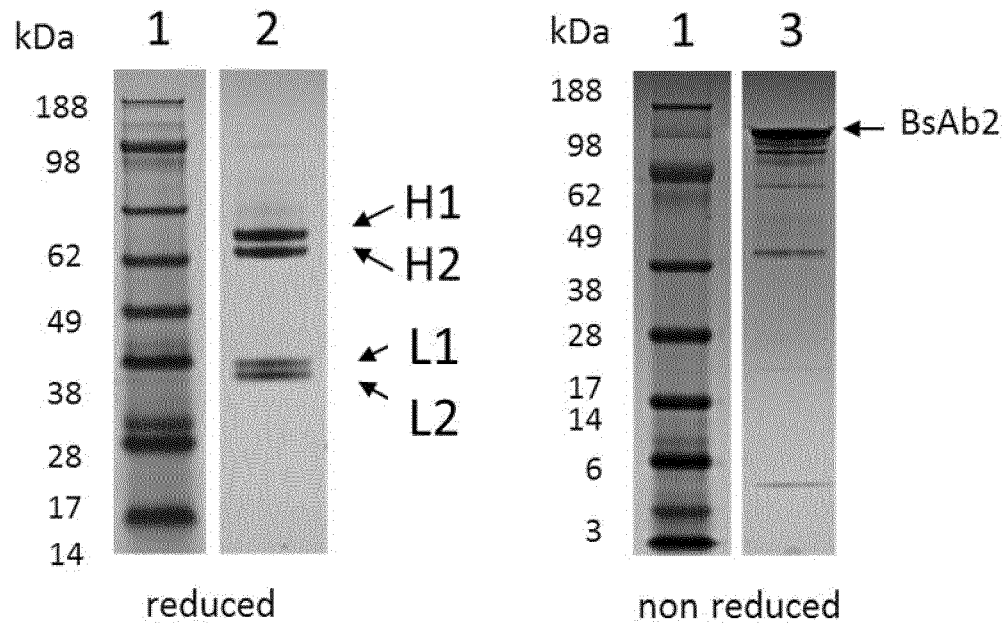

FIG. 8:

FIG. 8A: Characterization of the domain-exchanged BsAb2 (anti-CD16× anti-EGFR CH3-KiH) by SDS-PAGE, under reducing or non-reducing conditions. SDS-PAGE was stained with Colloidal Blue Stain Kit (Invitrogen). Lane 1: protein standard SeeBlue Plus 2 Pre-Stained Molecular Weight Marker, (Invitrogen). Lane 2: Reduced profile shows H1 band corresponding to VH(1)-CH3_KNOB (T366Y)-CH2-$CH3_{AG}$ (SEQ ID 2), H2 band that corresponds to VH(3)-CH1-CH2-$CH3_{GA}$ (SEQ ID 13), L1 band that corresponds to VL(3)-CL (SEQ ID 12) and L2 band corresponding to VL(1)-CH3_HOLE (Y407T) (SEQ ID 1). Lane 3: non-reduced profile shows main band corresponding to the domain-exchanged BsAb2 (anti-CD16× anti-EGFR CH3-KiH).

Figure 8B:
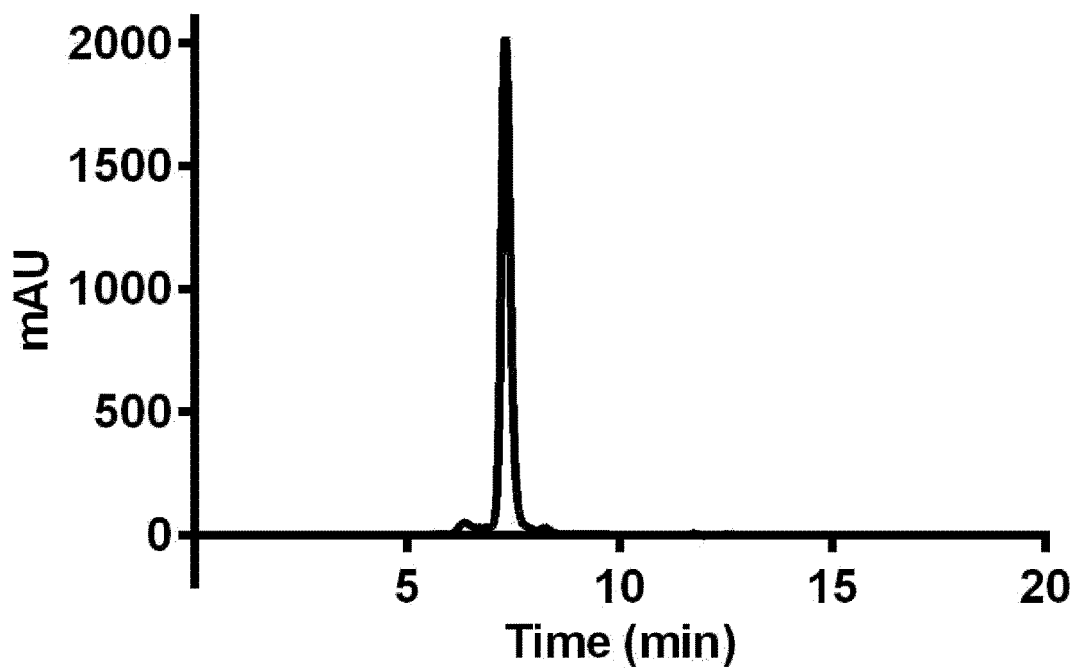

FIG. 8B: SEC profile of the domain-exchanged exchanged BsAb2 (anti-CD16× anti-EGFR CH3-KiH).

Figure 9:
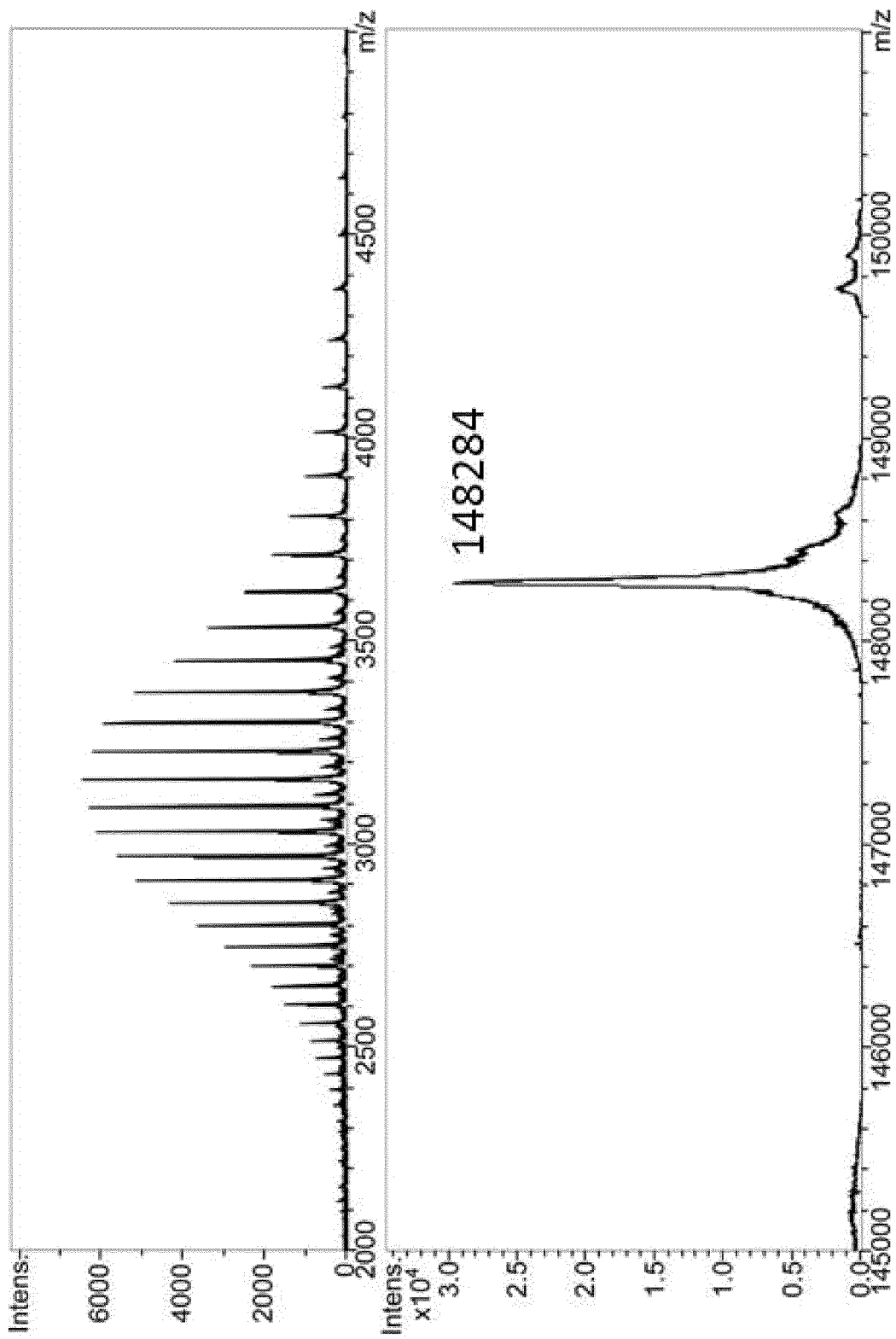

FIG. 9: LC-MS analysis of domain-exchanged bispecific antibody BsAb1 (anti-CD3× anti-EGFR CH3-KiH). Samples were deglycosylated by PNGase before measurement. Deconvoluted sum spectrum gives the mass of the correctly assembled bispecific antibody.

Figure 10:
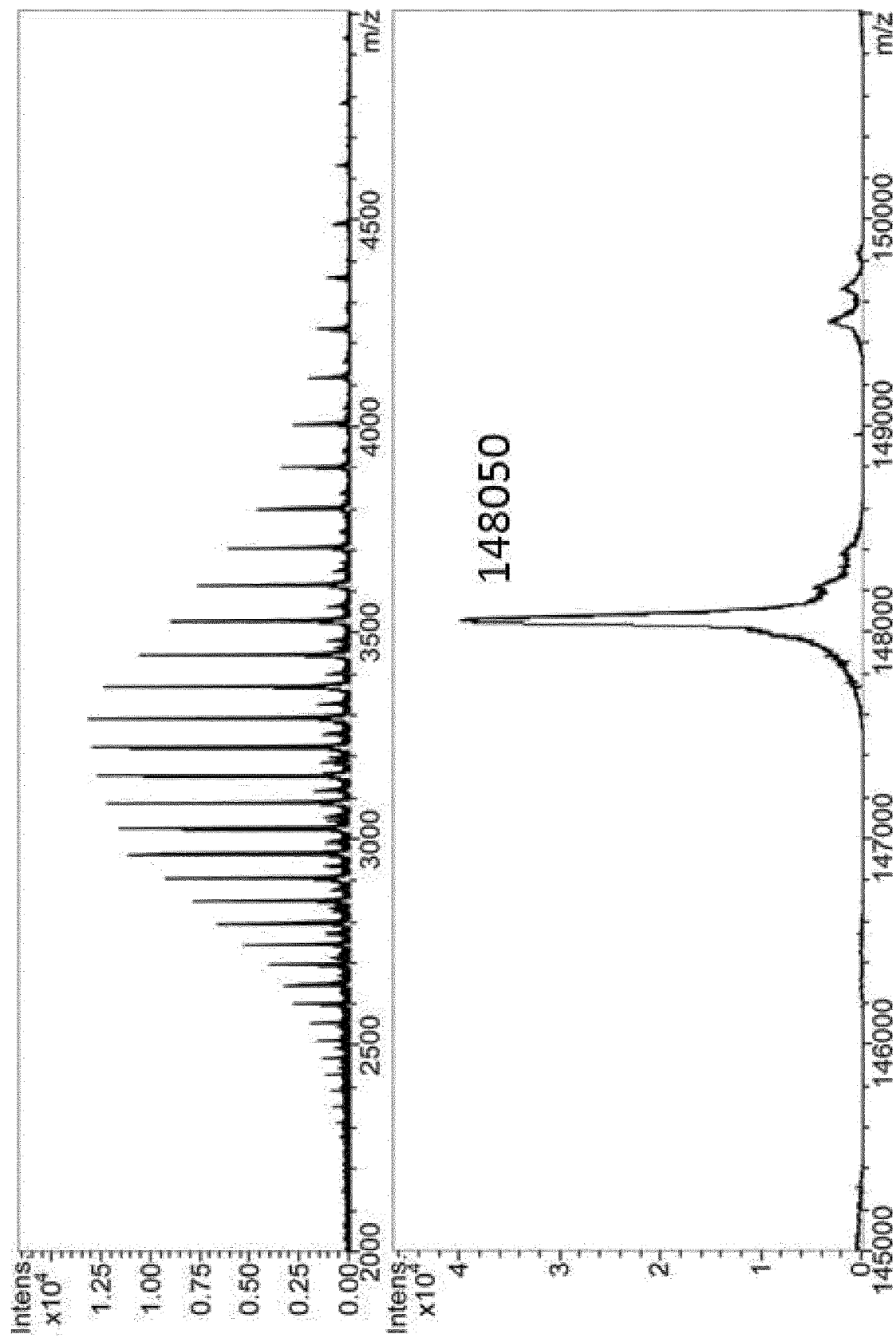

FIG. 10 LC-MS analysis of domain-exchanged exchanged bispecific antibody BsAb2 (anti-CD16× anti-EGFR CH3-KiH). Samples were deglycosylated by PNGase before measurement. Deconvoluted sum spectrum gives the mass of the correctly assembled bispecific antibody.

Figure 11:
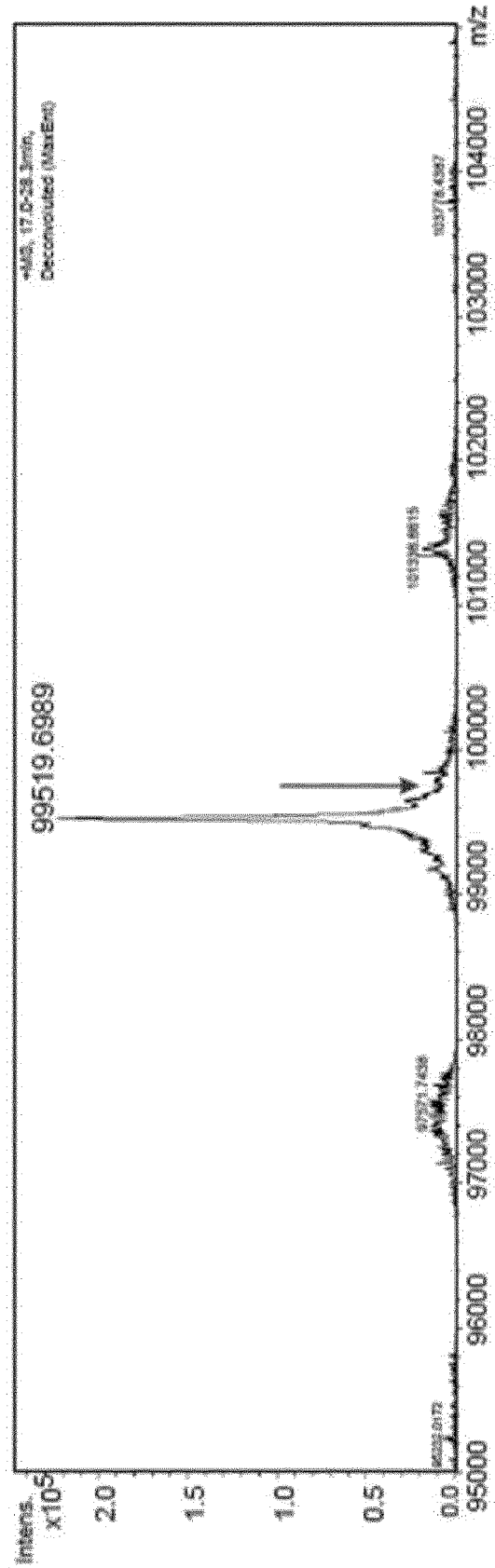

FIG. 11: Total mass determination of one-armed unengineered antibody coexpressed with 2 competing light chains by LC-MS. Only correctly assembled antibodies were found. Mispairing mAb could not be detected (position of potential mispaired mass marked with arrows).

Figure 12:
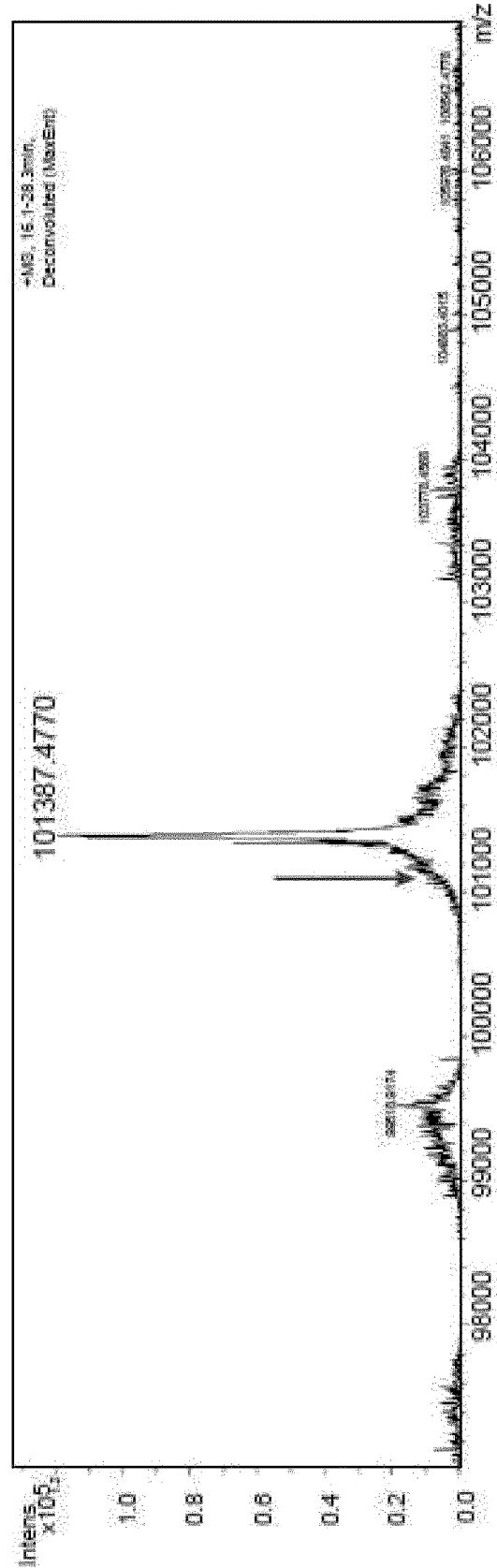

FIG. 12: Total mass determination of one-armed domain-exchanged antibody coexpressed with 2 competing light chains by LC-MS. Only correctly assembled antibodies were found. Mispairing mAb could not be detected (position of potential mispaired mass marked with arrows).

Figure 13:
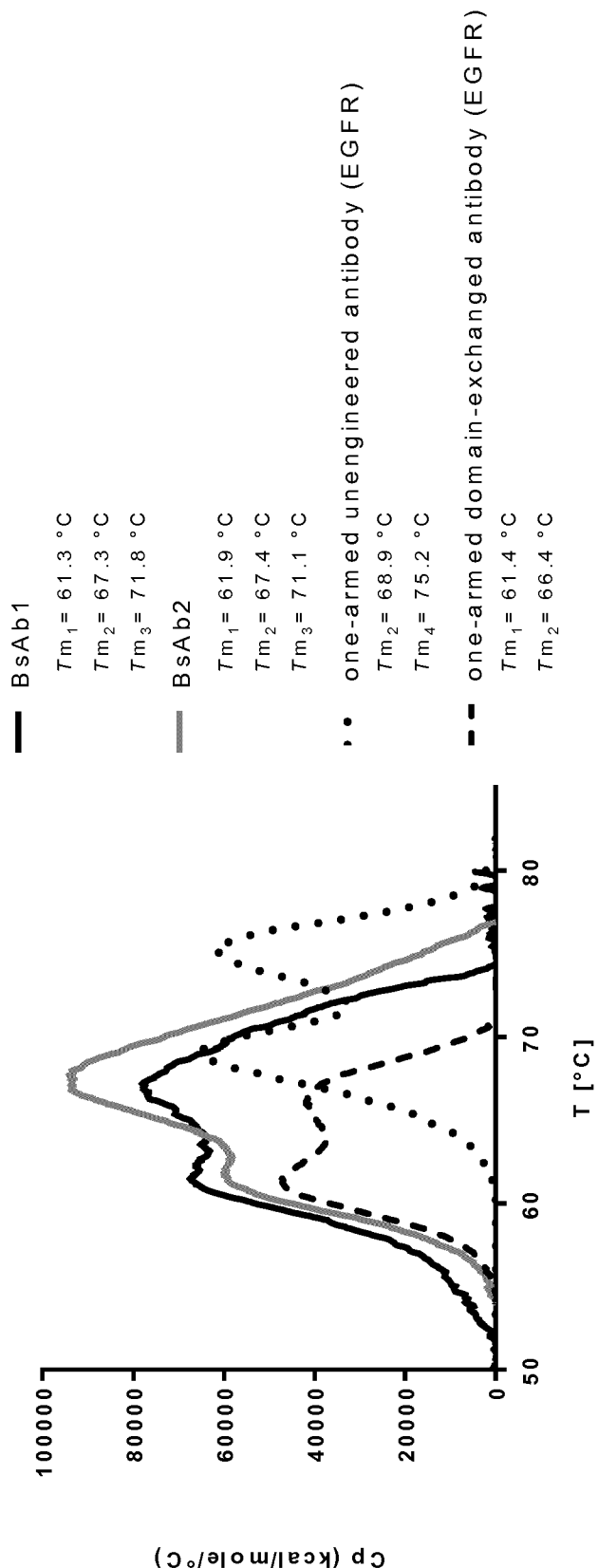

FIG. 13: DSC profiles of domain-exchanged bispecific antibodies BsAb1 and BsAb2.

Figure 14:
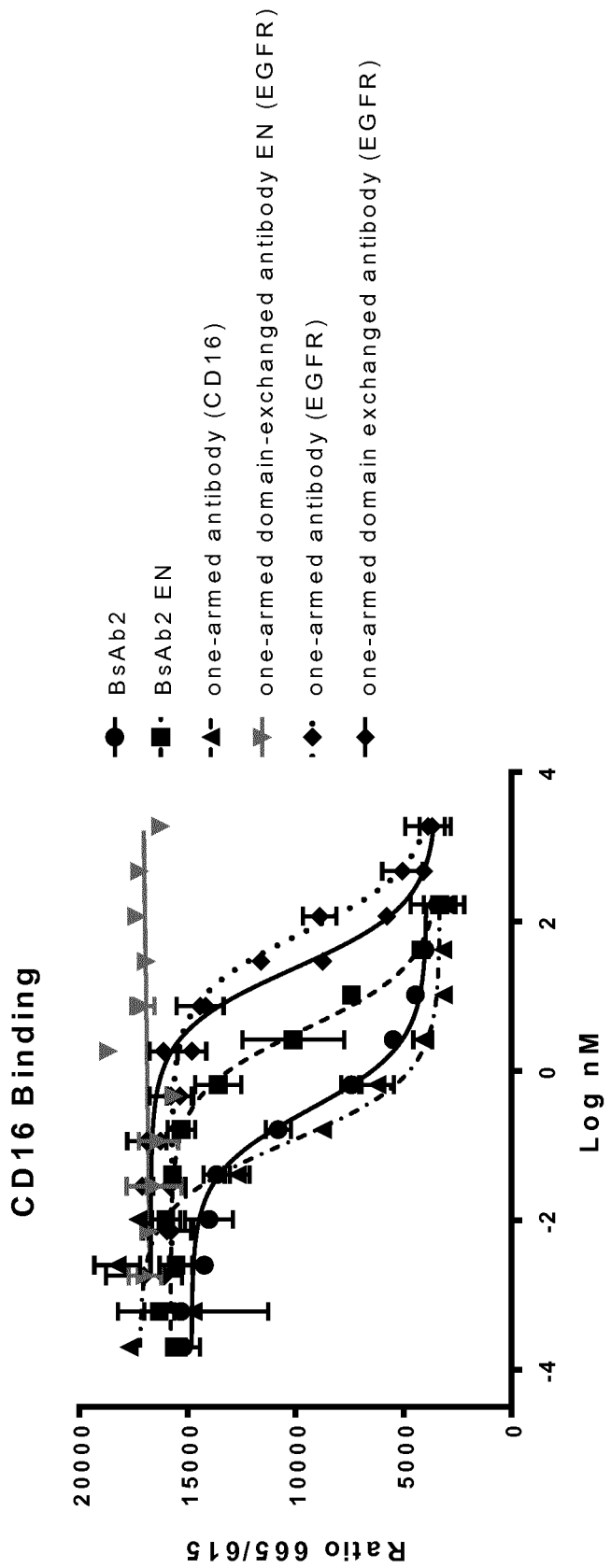

FIG. 14: Binding of antibodies to CD16a receptor. Binding was measured using CD16 HTRF cellular binding assay (CisBio). Measurement was performed in duplicates.

Figure 15:
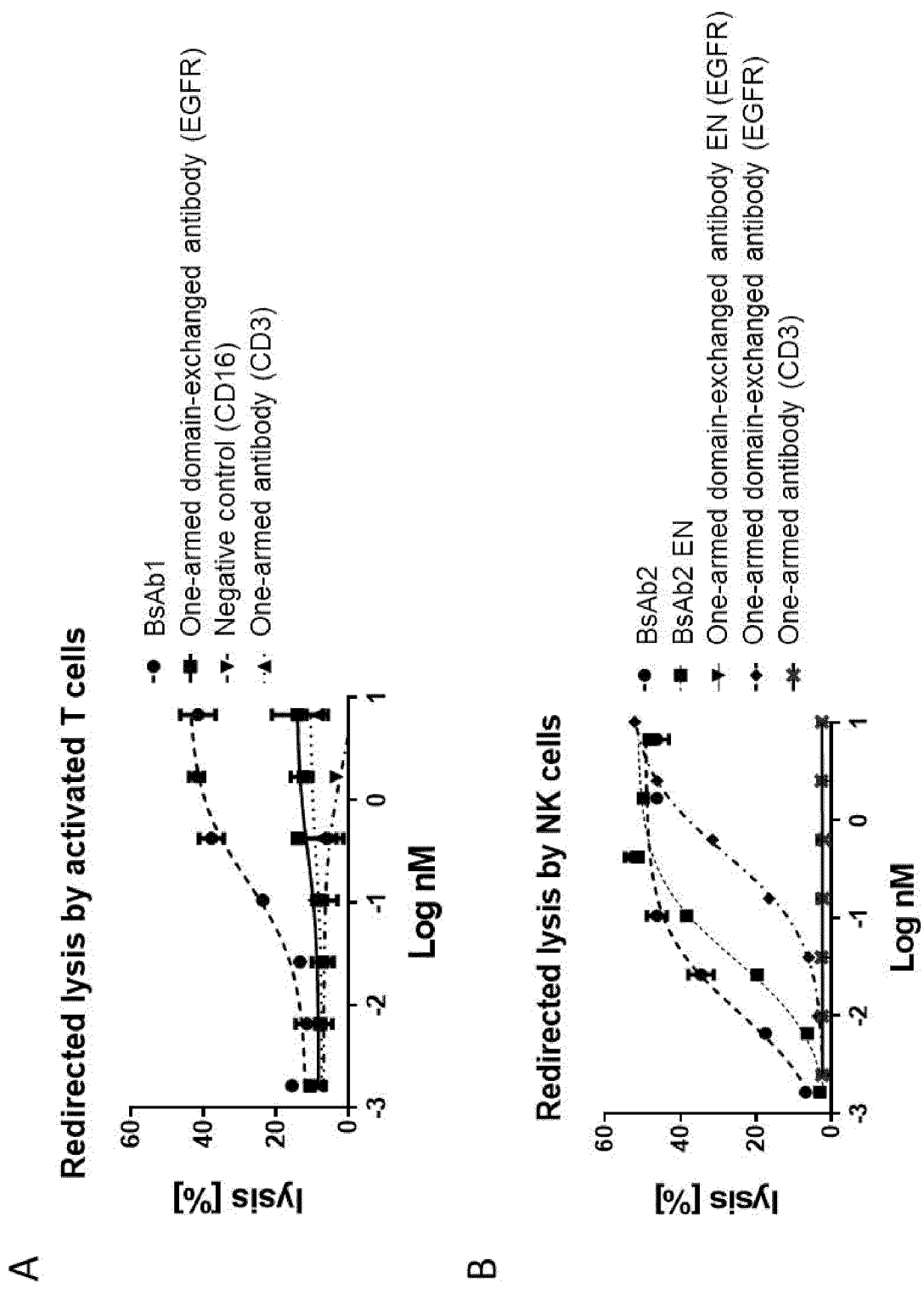

FIG. 15: Redirected lysis of A431 cells by effector cells in the presence of domain-exchanged bispecific antibody BsAb1 (A) and BsAb2 (B).

Figure 16:
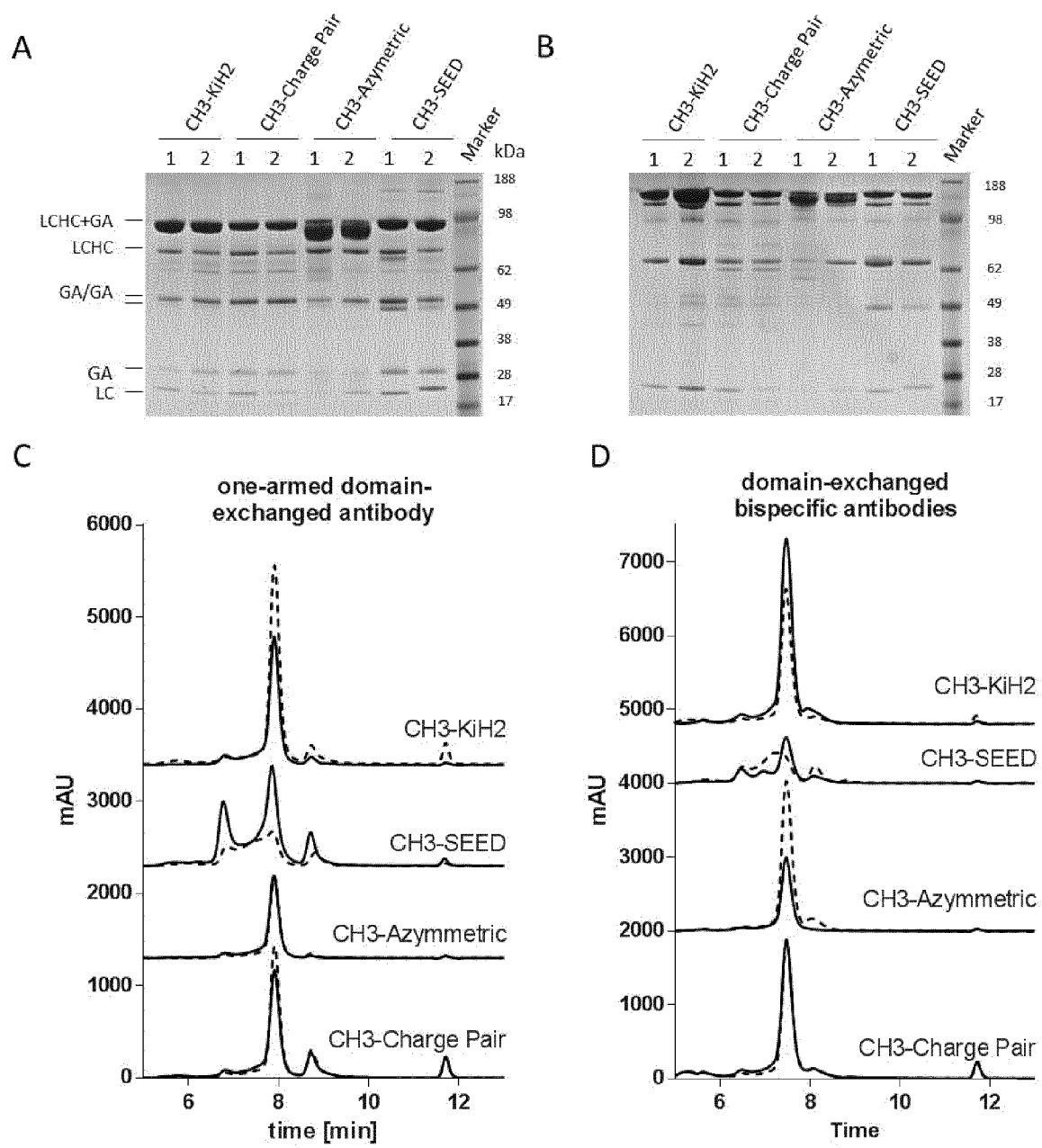

FIG. 16: Biophysical characterization of domain-exchanged antibodies with alternatively engineered Fab region by non-reducing SDS-PAGE and SEC of one-armed anti-EGFR SEED antibody (A and C) and domain-exchanged antibody (anti-CD3× anti-EGFR-CH3) (B and D). Proteins were produced in Expi293 cells and single-step purified by Protein A. Each lane of the SDS-PAGE gel was loaded with 5 µg protein and proteins were stained with Colloidal Blue Stain Kit (Invitrogen) after separation. Variant 1 and Variant 2 are indicated with 1 and 2 in the SDS-PAGE. SEC profiles of variants 1 are shown in black lines and variants 2 in dashed lines. (see Example 13 for more details)

Figure 17:
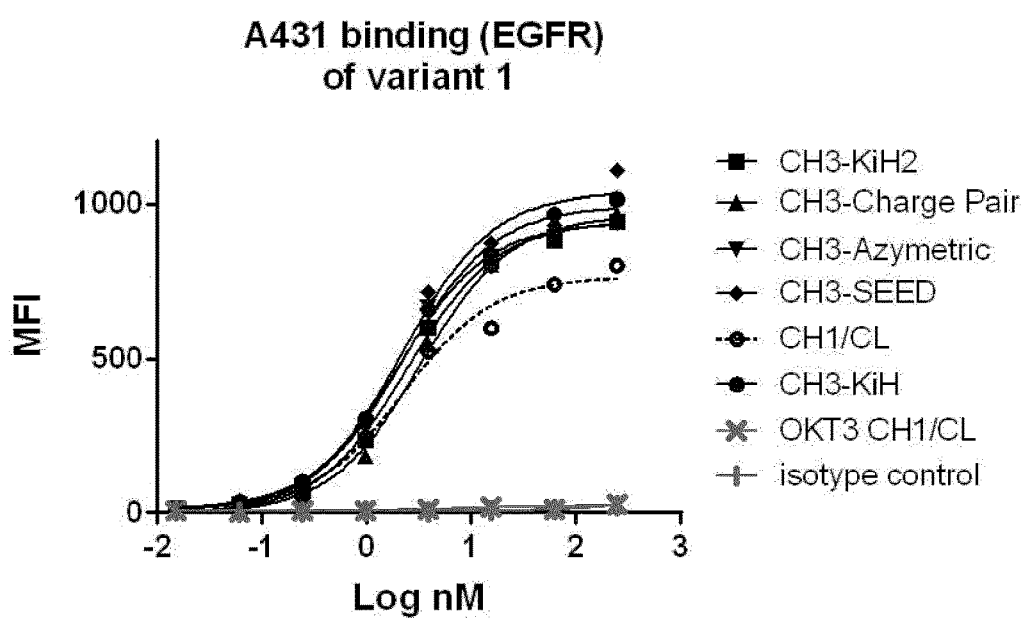
Figure 17:
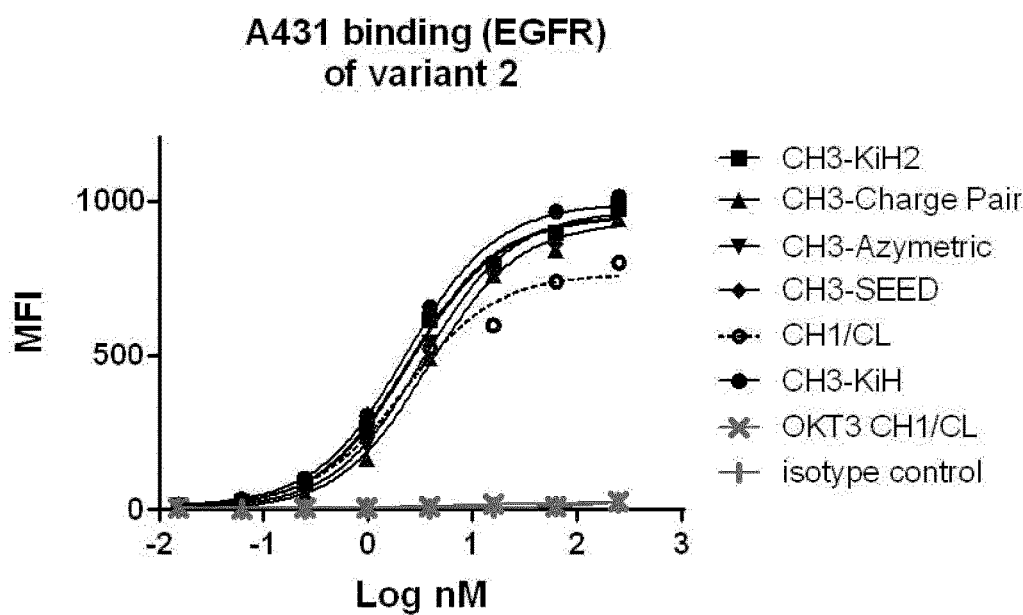

FIG. 17: EGFR binding of one-armed antibodies with alternatively domain-exchanged Fab arms of variants 1 (A) and variants 2 (B) measured by flow cytometry. The antibodies were tested in serial dilutions (1:3) and binding was detected using an anti-human Fc F(ab)2 antibody conjugated with phycoerythrin. Each data point represents the average of duplicates.

Figure 18:
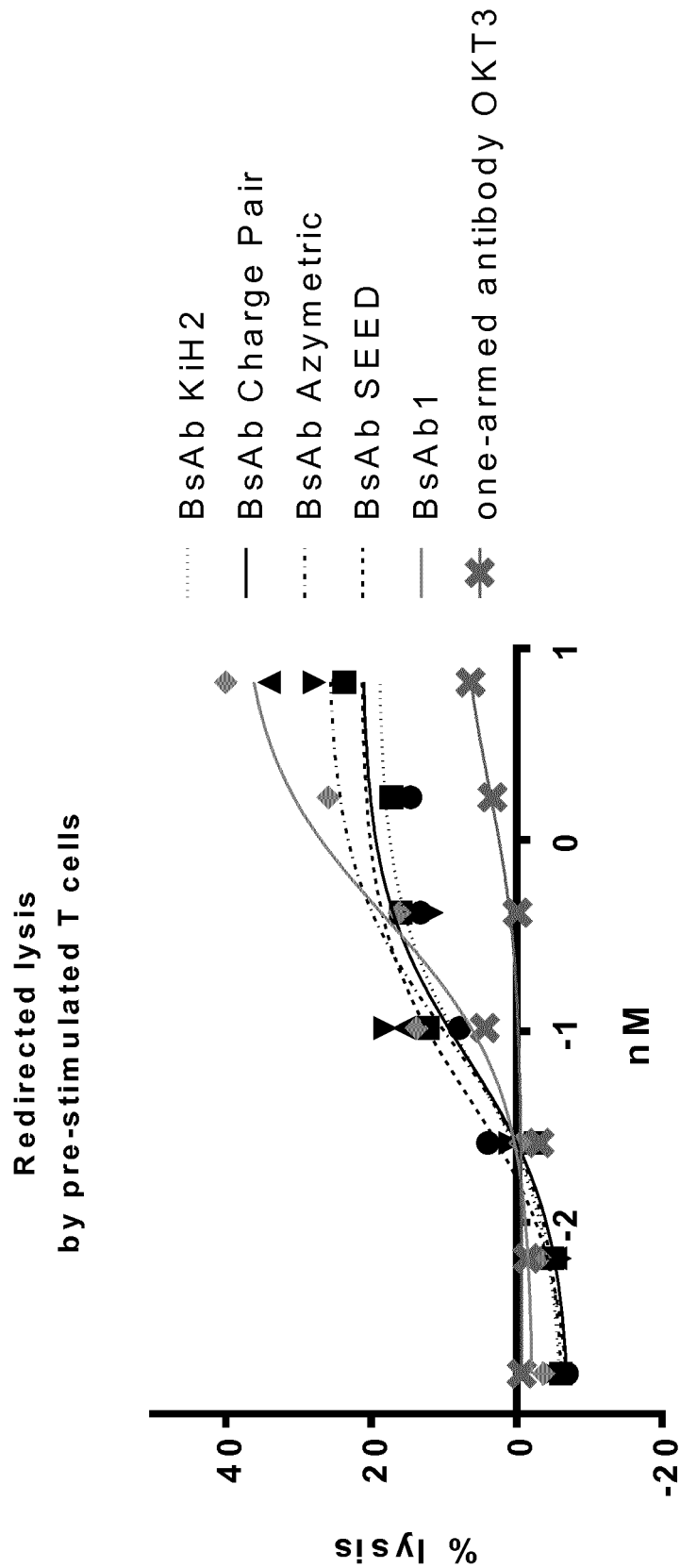

FIG. 18: Redirected lysis of target cells by activated T-cells in the presence of domain-exchanged bispecific antibodies with alternatively engineered Fab domains (variant 1). T cells were activated with IL-2 and anti-CD3 IgG in the culture medium for 24 h. Stimulated T cells were co-cultivated with A431 cells at E:T ratio of 10:1 in the presence of the tested antibodies in serial dilutions (1:4) for 18 h. Cell lysis (LDH release) was measured in the supernatant using CYTOTOX® 96 Non-Radioactive Cytotoxicity Assay (Promega). Each data point is the mean±SD of triplicates. For comparison, domain-exchanged BsAb1 (anti-CD3× anti-EGFR CH3-KiH) from previous examples was used.

Figure 19:
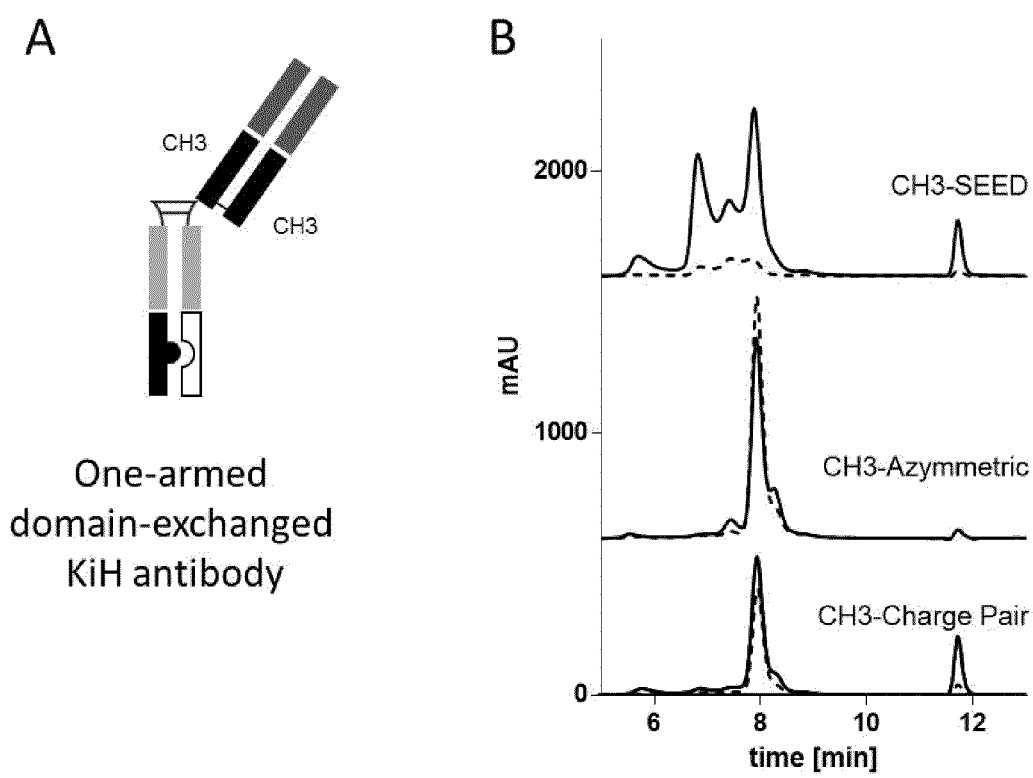

FIG. 19: Characterization of one-armed domain-exchanged KiH antibodies. These molecules, as illustrated in a schematic figure (A), were produced in Expi293 cells and after protein A purification analyzed by SEC (B). SEC profiles of variants 1 are shown in black lines and those of variants 2 in dashed lines.

Figure 20:
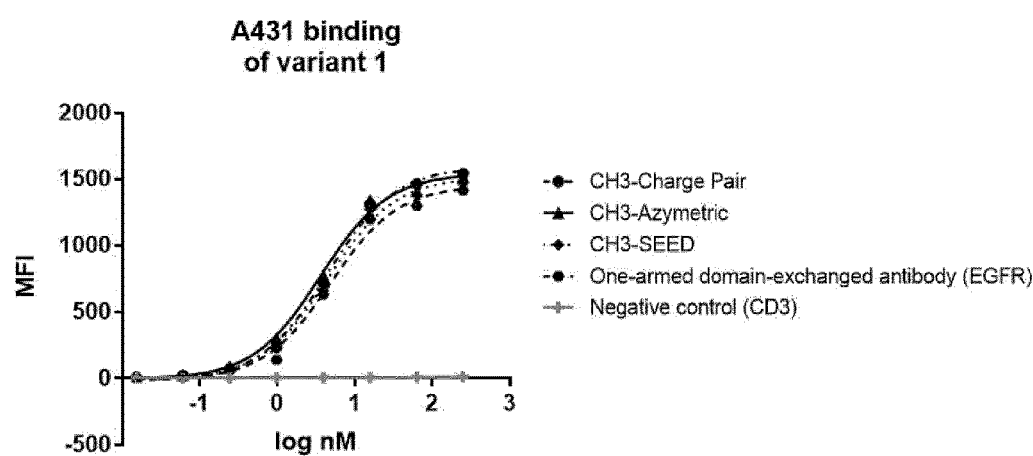
Figure 20:
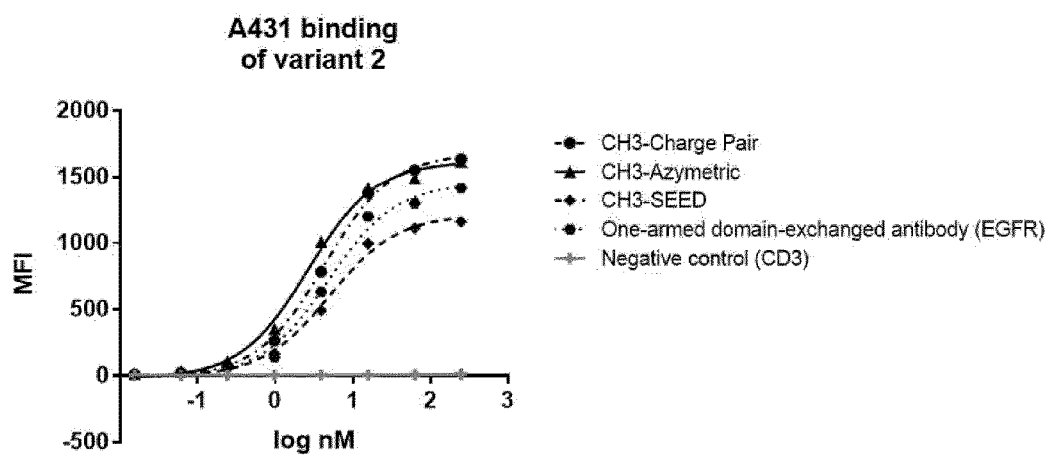

FIG. 20: EGFR binding of one-armed KiH antibodies with alternatively engineered Fab region of variants 1(A) and variants 2 (B) measured by flow cytometry. The antibodies were tested in serial dilutions (1:3) and antigen binding to A431 cells was detected using an anti-human Fc F(ab)2 antibody conjugated with phycoerythrin. Each data point represents a single measurement.

FIG. 21: Schematic illustration by a few examples of the variety of antibodies to be formed by linking CH3 domain-exchanged Fabs to different positions of an antibody and in combinations with engineered heterodimeric heavy chains. CH3 Domain-exchanged Fabs may be linked to different positions of a native antibody or to an engineered heterodimeric heavy chain pair. As illustrated in the examples, a variety of engineered CH3 domains can be used to form the heterodimeric heavy chains or to form the CH3 domain-exchanged Fabs (not all options are illustrated here).

21-1: Tetravalent bispecific antibody composed of native Ig antibody with N-terminal Fabs composed of paired VH1-CH1/VL1-CL domains combined with a CH3 Knobs-into-holes domain-exchanged Fab comprised of VH2-CH3 (Knob) and VL2-CH3(Hole), with the N-terminus of VH2-CH3(Knob) linked to the C-terminus of the native antibody.

21-2: Tetravalent bispecific antibody composed of native Ig antibody with N-terminal Fabs composed of paired VH1-CH1/VL1-CL domains combined with a CH3 Knobs-into-holes domain-exchanged Fab comprised of VH2-CH3(Hole) and VL2-CH3(Knob), with the N-terminus of VL2-CH3 (Knob) linked to the C-terminus of the native antibody.

21-3: Bispecific antibody, bivalent at N-terminus and monovalent at C-terminus composed of heterodimeric heavy chains assembled with SEED technology with N-terminal Fabs linked to each heavy chain composed of paired VH1-CH1/VL1-CL domains combined with a CH3 Knobs-into-holes domain-exchanged Fab comprised of VH2-CH3 (Knob) and VL2-CH3(Hole), with the N-terminus of VH2-CH3(Knob) linked to the C-terminus of only one of the SEED heavy chains.

21-4: Bispecific antibody, monovalent at N-terminus and bivalent at C-terminus composed of heterodimeric heavy chains assembled with SEED technology with an N-terminal Fab linked to only one of the SEED heavy chains composed of paired VH1-CH1/VL1-CL domains combined with a CH3 Knobs-into-holes domain-exchanged Fab comprised of VH2-CH3(Knob) and VL2-CH3(Hole), with the N-terminus of VH2-CH3(Knob) linked to the C-terminus of both of the SEED heavy chains.

21-5: Trispecific antibody, bivalent at N-terminus and with 2 different monovalent Fab domains at C-terminus composed of heterodimeric heavy chains assembled with SEED technology with N-terminal Fabs linked to each heavy chain composed of paired VH1-CH1/VL1-CL domains combined with one CH3 Knobs-into-holes domain-exchanged Fab comprised of VH2-CH3(Knob) and VL2-CH3(Hole) with the N-terminus of VH2-CH3(Knob) linked to the C-terminus of the GA SEED domain and a different CH3 Knobs-into-holes domain-exchanged Fab comprised of VH3-CH3(Knob) and VL3-CH3(Hole) with the N-terminus of VL3-CH3(Hole) linked to the C-terminus of the AG SEED domain.

FIG. 22:

Polypeptide sequences of the domain-exchanged bispecific antibody light and heavy chains:

Variable domains are italic characters. CH3 domain-exchanged sequence is underlined. SEED CH3-GA and SEED CH-AG domains are marked as bold. Introduced mutations forming knob, hole, or other variants designed to promote heterodimerization of CH3 domains (described in examples of some of the possible specific embodiments) are highlighted in grey and underlined.

SEQ ID 1:
VL(1)-CH3_HOLE (Y407T)

SEQ ID 2:
VH(1)-CH3_KNOB (T366Y)-CH2-CH3$_{AG}$

SEQ ID 3:
VL(2)-CL

SEQ ID 4:
VH(2)-CH1-CH2-CH3$_{GA}$

SEQ ID 5:
VH(2)-CH1-CH2-CH3$_{AG}$

SEQ ID 6:
VH(1)-CH3_KNOB (T366Y)-CH2-CH3$_{GA}$

SEQ ID 7:
VL(1)-CH3wt

-continued

SEQ ID 8:
VH(1)-CH3wt-CH2-CH3$_{GA}$

SEQ ID 9:
huFc_GA SEED

SEQ 10:
VL(1)-CL

SEQ 11:
VH(1)-CH1-CH2-CH3$_{AG}$

SEQ ID 12:
VL(3)-CL

SEQ ID 13:
VH(3)-CH1-CH2-CH3$_{GA}$

SEQ ID 14:
VH(3)-CH1-CH2-CH3$_{AG}$

SEQ ID 15:
VH(1)-CH3_KNOB (T366Y)-CH2$_{EN}$-CH3$_{AG}$

SEQ ID 16:
huFc_g1hingeEN-CH2$_{EN}$-CH3$_{GA}$

SEQ ID 17:
VH(3)-CH1-CH2$_{EN}$-CH3$_{GA}$

SEQ ID 18:
VH(1)-CH3_KNOB (T366W)-CH2-CH3$_{AG}$

SEQ ID 19:
VL(1)-CH3_HOLE (T366S, L368A, Y407V)

SEQ ID 20:
VH(1)-CH3_HOLE (T366S, L368A, Y407V)-CH2-CH3$_{AG}$

SEQ ID 21:
VL(1)-CH3_KNOB (T366W)

SEQ ID 22:
VH(1)-CH3 (E356K, D399K)-CH2-CH3$_{AG}$

SEQ ID 23:
VL(1)-CH3 (K392D, K409D)

SEQ ID 24:
VH(1)-CH3 (K392D, K409D)-CH2-CH3$_{AG}$

SEQ ID 25:
VL(1)-CH3 (E356K, D399K)

SEQ ID 26:
VH(1)-CH3 (T350V, L351Y, F405A, Y407V)-CH2-CH3$_{AG}$

SEQ ID 27:
VL(1)-CH3 (T350V, T366L, K392L, T394W)

SEQ ID 28:
VH(1)-CH3 (T350V, T366L, K392L, T394W)-CH2-CH3$_{AG}$

SEQ ID 29:
VL(1)-CH3 (T350V, L351Y, F405A, Y407V)

SEQ ID 30:
VH(1)-CH3_SEED (AG)-CH2-CH3$_{AG}$

SEQ ID 31:
VL(1)-CH3_SEED (GA)

SEQ ID 32:
VH(1)-CH3_SEED (GA)-CH2-CH3$_{AG}$

SEQ ID 33:
VL(1)-CH3_SEED (AG)

SEQ ID 34:
VH(1)-CH3 (E356K, D399K)-CH2-CH3_HOLE
(T366S, L368A, Y407V)

SEQ ID 35:
VH(1)-CH3 (K392D, K409D)-CH2-CH3_HOLE
(T366S, L368A, Y407V)

SEQ ID 36:
VH(1)-CH3 (T350V, L351Y, F405A, Y407V)-CH2-
CH3_HOLE (T366S, L368A, Y407V)

SEQ ID 37:
VH(1)-CH3 (T350V, T366L, K392L, T394W)-CH2-
CH3_HOLE (T366S, L368A, Y407V)

SEQ ID 38:
VH(1)-CH3_SEED (AG)-CH2-CH3_HOLE
(T366S, L368A, Y407V)

SEQ ID 39:
VH(1)-CH3_SEED (GA)-CH2-CH3_HOLE
(T366S, L368A, Y407V)

SEQ ID 40:
huFc_KNOB (T366W)

Amino acid sequences of human CH3 domains
SEQ ID 41: CH3 of human IgG1
SEQ ID 42: CH3 of human IgG2
SEQ ID 43: CH3 of human IgG3
SEQ ID 44: CH3 of human IgG4
SEQ ID 45: CH3 of human IgA
SEQ ID 46: CH3 of human IgM
SEQ ID 47: CH3 of human IgE
SEQ ID 48: CH3 of human IgD Amino acid sequences used as examples of transition sequences flanking the N-terminus and C-terminus of exchanged domains within Domain-Exchanged Fab heavy and light chain elements
SEQ ID 49: human Ckappa chain 108-111 (Kabat EU numbering)
SEQ ID 50: human IgG1 heavy chain 345-348 (Kabat EU numbering)
SEQ ID 51: human IgG1 heavy chain 438-444 (Kabat EU numbering)
SEQ ID 52: human VH J-region 109-113 (Kabat EU numbering)
SEQ ID 53: human CH1 domain 118-122 (Kabat EU numbering)

DETAILED DESCRIPTION

The term "antibody" as used herein is defined as antigen-binding polypeptides that are either immunoglobulins or immunoglobulin-like molecules, or other proteins exhibiting modular antibody formats, e.g. composed of one or more antibody domains and bearing antigen-binding properties similar to immunoglobulins or antibodies, in particular proteins that may exhibit mono- or bi- or multi-specific, or mono-, bi- or multivalent binding properties, e.g. at least two specific binding sites for epitopes of e.g. antigens, effector molecules or structures, specifically of pathogen origin or of human structure, like self-antigens including cell-associated or serum proteins. The terms "antibody" and "immunoglobulin" are herein used interchangeably.

An antibody typically consists of or comprises antibody domains, which are understood as constant and/or variable domains of the heavy and/or light chains of immunoglobulins, with or without a linker sequence. Antibodies are specifically understood to consist of or comprise combinations of variable and/or constant antibody domains with or without a linking sequence or hinge region, including pairs of variable antibody domains, such as one or two VH/VL pairs. Polypeptides are understood as antibody domains, if comprising a beta-barrel structure consisting of at least two beta-strands of an antibody domain structure connected by a loop sequence. Antibody domains may be of native structure or modified by mutagenesis or derivatization, e.g. to modify the antigen binding properties or any other property, such as stability or functional properties, such as binding to the Fc receptors FcRn and/or Fcgamma receptor.

The term "antibody" as used herein specifically includes full-length antibodies, including antibodies of immunoglobulin-like structures, such as domain-exchanged antibodies. Specifically, an antibody can be a full-length antibody, e.g. of an IgG type (e.g., an IgG1, IgG2, IgG3, or IgG4 subtype), IgA1, IgA2, IgD, IgE, or IgM antibody.

The term further includes derivatives or combinations of antibodies with antibody domains, or antibody fragments.

The term "full length antibody" can be used to refer to any antibody molecule comprising at least most of the Fc domain, specifically including a dimer of heavy chains, thereby producing at least a $CH3_{HC}/CH3_{HC}$ pair, and other domains commonly found in a naturally occurring antibody structures. This term "full length antibody" is used herein to emphasize that a particular antibody molecule is not an antibody fragment.

In accordance therewith, an antibody is typically understood as a protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as immunoglobulin variable region genes. Light chains (LC) are classified as either kappa or lambda. Heavy chains (HC) are classified as gamma, mu, alpha, delta, or epsilon, which in turn define the immunoglobulin classes, IgG, IgM, IgA, IgD and IgE, respectively.

HC or LC are each composed of at least two domains connected to each other to produce a chain of domains. It is specifically understood that an antibody HC includes a VH antibody domain and at least one antibody domain C-terminally bound to the VH. An antibody LC includes a VL antibody domain and at least one antibody domain C-terminally bound to the VL.

The definition further includes domains of the heavy and light chains of the variable region (such as dAb, Fd, Vl, Vk, Vh, VHH) and the constant region or individual domains of an intact antibody such as CH1, CH2, CH3, CH4, Cl and Ck, as well as mini-domains consisting of at least two beta-strands of an immunoglobulin domain connected by a structural loop. Typically, an immunoglobulin having an antigen-binding site through a specific CDR structure is able to bind a target antigen through the CDR loops of a pair of VH/VL domains.

The term "antibody" shall specifically include antibodies or immunoglobulins in the isolated form, which are substantially free of other antibodies or immunoglobulins directed against different target antigens and/or comprising a different structural arrangement of antibody domains. Still, an isolated antibody may be comprised in a combination preparation, containing a combination of the isolated antibody, e.g. with at least one other antibody, such as monoclonal antibodies or antibody fragments having different specificities.

The term "antibody" shall apply to antibodies or immunoglobulins of animal origin, including human species, such as mammalian, including human, murine, rabbit, goat, lama, cow and horse, or avian, such as hen, which term shall particularly include recombinant immunoglobulins which are based on a sequence of animal origin, e.g. human sequences.

The term "antibody" specifically applies to human antibodies.

The term "human" as used with respect to an antibody or immunoglobulin, is understood to include antibodies having variable and constant regions derived from human germline immunoglobulin sequences. A human antibody may include amino acid residues not encoded by human germline immunoglobulin sequences (e.g., mutations introduced by random or site-specific mutagenesis in vitro or by somatic mutation in vivo), for example in the CDRs. Human antibodies include antibodies isolated from human immunoglobulin libraries or from animals transgenic for one or more human immunoglobulin.

A human antibody is preferably selected or derived from the group consisting of IgA1, IgA2, IgD, IgE, IgG1, IgG2, IgG3, IgG4 and IgM.

A murine antibody is preferably selected or derived from the group consisting of IgA, IgD, IgE, IgG1, IgG2A, IgG2B, IgG2C, IgG3 and IgM.

The term "antibody" further applies to chimeric antibodies or immunoglobulins, e.g. chimeric antibodies, with sequences of origin of different species, such as sequences of murine and human origin.

The term "chimeric" as used with respect to an immunoglobulin or an antibody refers to those molecules wherein one portion of each of the amino acid sequences of heavy and light chains is homologous to corresponding sequences in immunoglobulins derived from a particular species or belonging to a particular class, while the remaining segment of the chain is homologous to corresponding sequences in another species or class. Typically the variable region of both light and heavy chains mimics the variable regions of immunoglobulins derived from one species of mammals, while the constant portions are homologous to sequences of immunoglobulins derived from another. For example, the variable region can be derived from presently known sources using readily available B-cells or hybridomas from non-human host organisms in combination with constant regions derived from, for example, human cell preparations.

The term "antibody" may further apply to humanized antibodies or immunoglobulins.

The term "humanized" as used with respect to an antibody or immunoglobulin refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen-binding sites may be wild-type or modified, e.g. by one or more amino acid substitutions, preferably modified to resemble human immunoglobulins more closely. Some forms of humanized immunoglobulins preserve all CDR sequences (for example a humanized mouse antibody which contains all six CDRs from the mouse antibody). Other forms have one or more CDRs which are altered with respect to the original antibody.

The term "antibody" further applies to monoclonal or polyclonal antibodies, specifically a recombinant antibody, which term includes all antibodies and antibody structures that are prepared, expressed, created or isolated by recombinant means, such as antibodies originating from animals, e.g. mammalians including human, that comprises genes or sequences from different origin, e.g. chimeric, humanized antibodies, or hybridoma derived antibodies. Further examples refer to antibodies isolated from a host cell transformed to express the antibody, or antibodies isolated from a recombinant, combinatorial library of antibodies or antibody domains, or antibodies prepared, expressed, created or isolated by any other means that involve splicing of antibody gene sequences to other DNA sequences.

The term "antibody" is understood to include functionally active variants of new or existing, e.g. naturally occurring antibodies. It is further understood that the term variant of an antibody, in particular variants of antibody-like molecules, or antibody variants, shall also include derivatives of such molecules as well. A derivative is any combination of one or more antibodies and or a fusion protein in which any domain or minidomain of the antibody may be fused at any position to one or more other proteins, such as to other antibodies or antibody fragments, but also to ligands, enzymes, toxins and the like. The antibodies of the invention can specifically be used as isolated polypeptides or as combination molecules, e.g. through recombination, fusion or conjugation techniques, with other peptides or polypeptides. The peptides are preferably homologous to immunoglobulin domain sequences, and are preferably at least 5 amino acids long, more preferably at least 10 or even at least 50 or 100 amino acids long, and constitute at least partially the loop region of the immunoglobulin domain.

A derivative of the antibody may also be obtained by association or binding to other substances by various chemical techniques such as covalent coupling, electrostatic interaction, di-sulphide bonding etc. The other substances bound to the immunoglobulins may be lipids, carbohydrates, nucleic acids, organic and inorganic molecules or any combination thereof (e.g. PEG, prodrugs or drugs). A derivative would also comprise an antibody with the same amino acid sequence but made completely or partly from non-natural or chemically modified amino acids. In a specific embodiment, the antibody is a derivative comprising an additional tag allowing specific interaction with a biologically acceptable compound. There is not a specific limitation with respect to the tag usable in the present invention, as far as it has no or tolerable negative impact on the binding of the immunoglobulin to its target. Examples of suitable tags include His-tag, Myc-tag, FLAG-tag, Strep-tag, Calmodulin-tag, GST-tag, MBP-tag, and S-tag. In another specific embodiment, the immunoglobulin is a derivative comprising a label. The term "label" as used herein refers to a detectable compound or composition which is conjugated directly or indirectly to the immunoglobulin so as to generate a "labeled" antibody. The label may be detectable by itself, e.g. radioisotope labels or fluorescent labels, or, in the case of an enzymatic label, may catalyze chemical alteration of a substrate compound or composition which is detectable.

A derivative of an antibody is e.g. derived from a parent antibody or antibody sequence, such as a parent antigen-binding (e.g. CDR) or framework (FR) sequence, e.g. mutants or variants obtained by e.g. in silico or recombinant engineering or else by chemical derivatization or synthesis.

The term "variants" as used herein shall specifically include any "mutant", "homolog", or "derivative" as described herein. The term "variant" shall specifically encompass functionally active variants. The functional variants of an antibody according to the invention are particularly functional with regard to antigen-binding and the dimerization of the LC and the HC, thereby forming a $CH3_{LC}/CH3_{HC}$ domain pair.

The term "variant" shall particularly refer to antibodies, such as mutant antibodies or fragments of antibodies, e.g. obtained by mutagenesis methods, in particular to delete, exchange, introduce inserts into a specific antibody amino acid sequence or region or chemically derivatize an amino acid sequence, e.g. in the constant domains to engineer the antibody stability, effector function or half-life, or in the variable domains to improve antigen-binding properties, e.g. by affinity maturation techniques available in the art. Any of the known mutagenesis methods may be employed, including point mutations at desired positions, e.g. obtained by randomization techniques. In some cases positions are chosen randomly, e.g. with either any of the possible amino acids or a selection of preferred amino acids to randomize the antibody sequences. The term "mutagenesis" refers to any art recognized technique for altering a polynucleotide or polypeptide sequence. Preferred types of mutagenesis include error prone PCR mutagenesis, saturation mutagenesis, or other site directed mutagenesis.

The term "functional variants" herein also referred to as "functionally active variant" may e.g. include a sequence resulting from modification of a parent sequence (e.g. from a parent antibody) by insertion, deletion or substitution of one or more amino acids, or chemical derivatization of one or more amino acid residues in the amino acid sequence, or nucleotides within the nucleotide sequence, or at either or both of the distal ends of the sequence, e.g. in a CDR or FR sequence, and which modification does not affect, in particular impair, the activity of this sequence. In the case of a binding site having specificity to a selected target antigen, the functionally active variant of an antibody would still have the predetermined binding specificity, though this could be changed, e.g. to change the fine specificity to a specific epitope, the affinity, the avidity, the Kon or Koff rate, etc. For example, an affinity matured antibody is specifically understood as a functionally active variant antibody. Hence, the modified CDR sequence in an affinity matured antibody is understood as a functionally active variant.

The functional activity is preferably determined by the structure and function of the variant as compared to a parent molecule, e.g. in an assay for determining the specificity of binding a target antigen and/or the required in vivo half-life of the molecule and/or the FcRn binding in a pH dependent way, e.g., determined in a standard assay by measuring functionality of the immunoglobulin.

The functional activity of an antibody in terms of antigen-binding is typically determined in an ELISA assay, BIAcore assay, Octet BLI assay, or FACS based assay when the antigen is expressed on cell surface.

Functionally active variants may be obtained, e.g. by changing the sequence of a parent antibody, e.g. a monoclonal antibody having a specific native structure of an immunoglobulin, such as an IgG1 structure, to obtain a variant having the same specificity in recognizing a target antigen, but having a structure which differs from the parent structure, e.g. to modify any of the immunoglobulin domains to introduce specific mutations, to produce bispecific constructs, or to produce a fragment of the parent molecule.

Typically, a parent immunoglobulin or sequence may be modified to produce variants which incorporate mutations within a sequence region besides the antigen-binding site, or within the binding site, that does not impair the antigen binding, and preferably would have a biological activity similar to the parent antibody, including the ability to bind an antigen, e.g. with substantially the same biological activity, as determined by a specific binding assay or functional test to target the antigen.

The term "substantially the same biological activity" as used herein refers to the activity as indicated by substantially the same activity being at least 20%, at least 50%, at least 75%, at least 90%, e.g. at least 100%, or at least 125%, or at least 150%, or at least 175%, or e.g. up to 200% of the activity as determined for the comparable or parent antibody.

The preferred variants as described herein are functionally active with regard to the antigen binding, preferably which have a potency to specifically bind the individual antigen, and not significantly binding to other antigens that are not target antigens, e.g. with a Kd value difference of at least 2 logs, preferably at least 3 logs. The antigen binding by a functionally active variant is typically not impaired, corresponding to about substantially the same binding affinity as the parent antibody or sequence, or antibody comprising a sequence variant, e.g. with a Kd value difference of less than 2 logs, preferably less than 3 logs, however, with the possibility of even improved affinity, e.g. with a Kd value difference of at least 1 log, preferably at least 2 logs.

Specific functional variants as described herein are domain-exchanged antibodies, in particular functional variants comprising one or more engineered $CH3_{HET}$ domains, which comprise one or more point mutations to improve the $CH3_{HET}/CH3_{HET}$ dimer formation.

In a preferred embodiment the functionally active variant of a parent antibody
 a) is a biologically active fragment of the antibody, the fragment comprising at least 50% of the sequence of the molecule, preferably at least 60%, at least 70%, at least 80%, at least 90%, or at least 95% and most preferably at least 97%, 98% or 99%;
 b) is derived from the antibody by at least one amino acid substitution, addition and/or deletion, wherein the functionally active variant has a sequence identity to the molecule or part of it, such as an antibody of at least 50% sequence identity, preferably at least 60%, more preferably at least 70%, more preferably at least 80%, still more preferably at least 90%, even more preferably at least 95% and most preferably at least 97%, 98% or 99%; and/or
 c) consists of the antibody or a functionally active variant thereof and additionally at least one amino acid or nucleotide heterologous to the polypeptide or the nucleotide sequence.

In one preferred embodiment of the invention, the functionally active variant of the antibody according to the invention is essentially identical to the variant described above, but differs from its polypeptide or the nucleotide sequence, respectively, in that it is derived from a homologous sequence of a different species. These are referred to as naturally occurring variants or analogs.

The term "functionally active variant" also includes naturally occurring allelic variants, as well as mutants or any other non-naturally occurring variants. As is known in the art, an allelic variant is an alternate form of a (poly) peptide that is characterized as having a substitution, deletion, or addition of one or more amino acids that does essentially not alter the biological function of the polypeptide.

Functionally active variants may be obtained by sequence alterations in the polypeptide or the nucleotide sequence, e.g. by one or more point mutations, wherein the sequence alterations retains or improves a function of the unaltered polypeptide or the nucleotide sequence, when used in combination of the invention. Such sequence alterations can include, but are not limited to, (conservative) substitutions, additions, deletions, mutations and insertions.

Specific functionally active variants are CDR variants. A CDR variant includes an amino acid sequence modified by at least one amino acid in the CDR region, wherein said modification can be a chemical or a partial alteration of the amino acid sequence, which modification permits the variant to retain the biological characteristics of the unmodified sequence. A partial alteration of the CDR amino acid sequence may be by deletion or substitution of one to several amino acids, e.g. 1, 2, 3, 4 or 5 amino acids, or by addition or insertion of one to several amino acids, e.g. 1, 2, 3, 4 or 5 amino acids, or by a chemical derivatization of one to several amino acids, e.g. 1, 2, 3, 4 or 5 amino acids, or combination thereof. The substitutions in amino acid residues may be conservative substitutions, for example, substituting one hydrophobic amino acid for an alternative hydrophobic amino acid.

Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc.

A point mutation is particularly understood as the engineering of a polynucleotide that results in the expression of an amino acid sequence that differs from the non-engineered amino acid sequence in the substitution or exchange, deletion or insertion of one or more single (non-consecutive) or doublets of amino acids for different amino acids.

Preferred point mutations refer to the exchange of amino acids of the same polarity and/or charge. In this regard, amino acids refer to twenty naturally occurring amino acids encoded by sixty-four triplet codons. These 20 amino acids can be split into those that have neutral charges, positive charges, and negative charges:

The "neutral" amino acids are shown below along with their respective three-letter and single-letter code and polarity:
 Alanine: (Ala, A) nonpolar, neutral;
 Asparagine: (Asn, N) polar, neutral;
 Cysteine: (Cys, C) nonpolar, neutral;
 Glutamine: (Gln, Q) polar, neutral;
 Glycine: (Gly, G) nonpolar, neutral;
 Isoleucine: (Ile, I) nonpolar, neutral;
 Leucine: (Leu, L) nonpolar, neutral;
 Methionine: (Met, M) nonpolar, neutral;
 Phenylalanine: (Phe, F) nonpolar, neutral;
 Proline: (Pro, P) nonpolar, neutral;
 Serine: (Ser, S) polar, neutral;
 Threonine: (Thr, T) polar, neutral;
 Tryptophan: (Trp, W) nonpolar, neutral;
 Tyrosine: (Tyr, Y) polar, neutral;
 Valine: (Val, V) nonpolar, neutral; and
 Histidine: (His, H) polar, positive (10%) neutral (90%).
The "positively" charged amino acids are:
 Arginine: (Arg, R) polar, positive; and
 Lysine: (Lys, K) polar, positive.
The "negatively" charged amino acids are:
 Aspartic acid: (Asp, D) polar, negative; and
 Glutamic acid: (Glu, E) polar, negative.

"Percent (%) amino acid sequence identity" with respect to antibody sequences is defined as the percentage of amino acid residues in a candidate sequence that are identical with the amino acid residues in the specific polypeptide sequence, after aligning the sequence and introducing gaps, if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full length of the sequences being compared.

An antibody variant is specifically understood to include homologs, analogs, fragments, modifications or variants with a specific glycosylation pattern, e.g. produced by glycoengineering, which are functional and may serve as functional equivalents, e.g. binding to the specific targets and with functional properties. An antibody or CH3 antibody domain may be glycosylated or unglycosylated. For example, a recombinant antibody as described herein may be expressed in an appropriate mammalian cell to allow a specific glycosylation of the molecule as determined by the host cell expressing the immunoglobulin.

The term "beta-sheet" or "beta strand" of an antibody domain, in particular of a constant antibody domain such as a CH3 domain is herein understood in the following way. An antibody domain typically consists of at least two beta strands connected laterally by at least two or three backbone hydrogen bonds, forming a generally twisted, pleated sheet. A beta strand is a single continuous stretch of amino acids of typically 3 to 10 amino acids length adopting such an extended conformation and involved in backbone hydrogen bonds to at least one other strand, so that they form a beta sheet. In the beta sheet, the majority of beta strands are arranged adjacent to other strands and form an extensive hydrogen bond network with their neighbors in which the N—H groups in the backbone of one strand establish hydrogen bonds with the C=O groups in the backbone of the adjacent strands.

The structure of antibody constant domains, such as CH2 or CH3 domains, is similar to that of variable domains, consisting of beta-strands connected by loops, some of which contain short alpha-helical stretches. The framework is mostly rigid and the loops are comparatively more flexible, as can be seen from the b-factors of various Fc crystal structures. An antibody CH3 domain typically has seven beta strands forming a beta-sheet (A-B-C-D-E-F-G), wherein the beta strands are linked via loops, three loops being located at the N-terminal tip of the CH3 domain (A-B, C-D, E-F), and further three loops being located at the N-terminal tip of the CH3 domain (B-C, D-E, F-G). A "loop region" of a CH3 domain refers to the portion of the protein located between regions of beta strands (for example, each CH3 domain comprises seven beta sheets, A to G, oriented from the N- to C-terminus).

Preferably a pair of CH3 domains, such as the $CH3_{HET}/CH3_{HET}$ dimer is produced by connecting a binding surface involving the A, B and E strands, herein also referred to as the beta-sheet region of a first CH3 which is brought into contact with the beta-sheet region of a second CH3 to produce a dimer.

A "CH3 domain" is herein specifically understood as a polypeptide obtained from an antibody CH3 domain, such as from a Fc fragment of an antibody. The Fc fragment can be from an IgG, IgA, IgD, IgE or IgM. Specifically, the CH3 domain as described herein may comprise an aminoacid sequence of a human IgG1 antibody (identified as SEQ ID 41), a human IgG2 antibody (identified as SEQ ID 42), a human IgG3 antibody (identified as SEQ ID 43), or a human IgG4 antibody (identified as SEQ ID 44), or a human IgA antibody (identified as SEQ ID 45), or a human IgM antibody (identified as SEQ ID 45), or a human IgM antibody (identified as SEQ ID 46), or a human IgE antibody (identified as SEQ ID 47), or a human IgD antibody (identified as SEQ ID 48), or a functional variant thereof, e.g. with a certain sequence identity.

In one embodiment described herein, the CH3 domain may comprise mutations, e.g. can have at least a portion of one or more beta strands replaced with heterologous sequences, such as to include one or more point mutations, e.g. knob or hole mutations.

Specific knob mutations are one or more amino acid substitutions to increase the contact surface between two domains by incorporating one or more amino acids which provide for an additional protuberance of a beta-strand structure, e.g. one or more of CH3 knob mutations selected from the group consisting of T366Y, T366W, T394W, F405A. A specific knob modification denotes the mutation T366W in the CH3 domain of an antibody (numbering according to EU index of Kabat). Knob mutations specifically provide a matching (cognate) surface to bind another antibody domain, e.g. which is modified to incorporate hole mutations.

Specific hole mutations are one or more amino acid substitutions to increase the contact surface between two domains by incorporating one or more amino acids which provide for an additional cave of a beta-strand structure, e.g. one or more of CH3 hole mutations selected from the group consisting T366S, L368A and Y407V. A specific hole-modification denotes any of the mutations T366S, L368A, Y407V, Y407T in the CH3 domain of an antibody (numbering according to EU index of Kabat). Hole mutations specifically provide a matching (cognate) surface to bind another antibody domain, e.g. which is modified to incorporate knob mutations.

Matching knob into hole mutations are, e.g. T366Y on one CH3 domain and the matching Y407'T on the second CH3 domain of the CH3 domain pair, herein referred to as T366Y/Y407'T. Further matching mutations are T366Y/Y407'T,
F405A/T394'W,
T366Y:F405A/T394'W:Y407'T,
T366W/Y407'A, and/or
S354C:T366W/Y349'C:T366'S:L368'A:Y407'V.

Specific CH3 mutations include an intermolecular beta-strand swap, e.g. wherein one or more segments or sequences within a CH3 beta strand are mutated to incorporate segments or sequences of antibody domains which differ from the original CH3 domain, e.g. of antibody domains of a different type or subtype. Specific mutants are obtained by strand exchange, wherein a CH3 domain of an IgG type incorporates one or more segments or sequences of a CH3 domain of an IgA type. If two strand exchanged CH3 domains are mutated to form a cognate pair, the IgA segments or sequences of each of the CH3 domains produce an interdomain contact surface which is cognate, such that the mutated CH3 domains preferentially pair with each other over a wild-type CH3 domain. Specific examples of such modifications of antibody domains to incorporate a segment swap may be strand-exchange engineered domains (SEED). Such modifications may be used to produce asymmetric and bispecific immunoglobulins, in particular bispecific antibodies by preferentially pairing the SEED modified CH3 domains of the heavy chains. This is based on exchanging structurally related sequences of immunoglobulin within the conserved CH3 domains. Alternating sequences from human IgA and IgG in the SEED CH3 domains generate two asymmetric but complementary domains, designated AG and GA. The SEED design allows efficient generation of AG/GA heterodimers, while disfavoring homodimerization of AG and GA SEED CH3 domains.

Specific CH3 mutations include the incorporation of cysteine residues which are capable of forming disulfide bridges to stabilize an antibody domain by an additional intradomain disulfide bridge, or a pair of antibody domains by an additional interdomain disulfide bridge. Disulfide bonds are usually formed from the oxidation of thiol groups of two cysteins, thereby linking the S-atoms to form a disulfide bridge between the two cysteine residues. Specifically, cysteine may be inserted (by an additional amino acid or an amino acid substitution) in the C-terminal region or at the C-terminus of a CH3 domain. A pair of CH3 that bear the additional cysteine modification can be stabilized by disulfide bond formation between the CH3 pair, thereby producing a CH3/CH3 dimer. In some embodiments disulfide-linked immunoglobulin or immunoglobulin domains comprises homodimers or heterodimers, thus, pairs of the same or different domains.

In order to allow proper pairing of the immunoglobulin chains or domains, any of the CH3 mutations may specifically be employed, e.g. the knobs-into-holes technology, the SEED technology, charge repulsion technology, disulfide linkage or the cross-mAb technology can be used in order to reduce the amount of not correctly associated molecules.

A "pair" of antibody domains, e.g. a pair of CH3 domains, is understood as a set of two antibody domains, where one has an area on its surface or in a cavity that specifically binds to, and is therefore complementary to, an area on the other one.

Immunoglobulin domains, in particular antibody domains, may associate to form a pair of immunoglobulin domains through contact of a beta-sheet region. Such domain pair is also referred to as a dimer, which is e.g. associated by electrostatic interaction, recombinant fusion or covalent linkage, placing two domains in direct physical association, e.g. including both in solid and in liquid form. Specifically described herein is a CH3/CH3 dimer which can be a pair of CH3 domains consisting of the same primary, secondary and tertiary structure, e.g. the same amino acid sequence, i.e. a "homodimer", or a pair of CH3 domains which differ in any of the primary, secondary and tertiary structure, e.g. which differ in the amino acid sequence of any of the beta strand or loop regions. Specific heterodimers may be produced to form a cognate pair of CH3/CH3 domains.

The term "cognate" with respect to a pair of domains or domain dimer is understood as domains which have a matching binding point or structure to obtain a contact surface on each of the domains to which preferentially form a pair of such domains. Specific CH3 domains are understood as "cognate" or a cognate pair of CH3/CH3 domains, if at least one of the CH3 domains is modified to preferentially bind its cognate CH3 binding partner to produce the CH3/CH3 pair. Specifically, both CH3 domains may be modified by matching mutations, e.g. knob-into-hole mutations, SEED mutations, additional cysteine residues for disulfide bridge formation, or modifications employing charge repulsion technology.

The term "heterologous" with respect to an antibody domain that is incorporated into an immunoglobulin, e.g. a heterologous CH3 domain, herein also referred to as $CH3_{HET}$, is understood to encompass a foreign CH3 domain incorporated into an antibody or antibody HC or LC. An immunoglobulin that is engineered to incorporate a $CH3_{HET}$ domain by substituting an existing or naturally-occurring immunoglobulin domain, e.g. a CL, CH1, or a CH2 domain of the parent immunoglobulin structure, is herein understood as a "domain-exchanged" immunoglobulin. Such domain-exchanged immunoglobulin may be further modified to produce functional variants, e.g. fragments, mutants or amino acid extensions, e.g. domain additions.

The term "foreign" in the context of parts of molecules, such as amino acids, amino acid sequences or immunoglobulin domains, shall mean the newly introduced parts that may be naturally occurring, but foreign to the site of modification, or (functional) variants of such naturally occurring parts, or else may be substitutes of naturally occurring parts.

"Foreign" with reference to CH3 domain means that the CH3 domain is of a different origin and/or of the same origin (e.g. of the same type or subtype, and/or the same species) but differs in its position in the immunoglobulin molecules. For example, an additional $CH3_{HET}$ of the same species and immunoglobulin type or subtype is placed at a position other than the C-terminal antibody domain of an Fc. Any CH3 domain placed into a Fab part of an antibody is understood to be a $CH3_{HET}$. Typically, such Fab would include a pair of $CH3_{HET}/CH3_{HET}$, each $CH3_{HET}$ being N-terminally linked to a variable domain. Specific examples of $CH3_{HET}$ in a HC are C-terminally linked to any further antibody domain, e.g. a constant domain, preferably selected from the group consisting of CH2, CH3, and CH4. Thereby, new HC and/or LC may be produced incorporating a $CH3_{HET}$ domain. Specifically, new pairs of HC/HC and/or HC/LC may be produced which comprise a $CH3_{HET}/CH3_{HET}$ pair, preferably a cognate pair of $CH3_{HET}/CH3_{HET}$.

It is specifically described herein that the $CH3_{HET}$ domain employed in the antibody of the invention is a nonimmune domain. Such nonimmune CH3 domain is specifically understood not to comprise an antigen-binding site in the loop region. A CH3 domain would not naturally comprise any CDR loop region or antigen-binding site, therefore a wild-type CH3 domain is understood as a nonimmune domain. Some antibody engineering techniques enable the incorporation of an antigen-binding site into the loop region of a constant domain, such as a CH3 domain. Such loop region of a constant domain is referred to as a "structural loop region" which employs the binding of an antigen by one or more loops of a constant domain. In contrast to such "immune" CH3 domain which are able to bind an antigen through interaction with the structural loop region, the $CH3_{HET}$ domain as used herein is a nonimmune domain, thus, does not comprise such antigen-binding site in the structural loop region.

An antibody comprising $CH3_{HET}$ at a position other than in the CH2-CH3 context of an Fc part of an antibody, in particular a domain-exchanged immunoglobulin, specifically comprises a new type of linkage, at least a new N-terminal linkage to another domain, thereby providing a new structure at the interface of two domains. The preferred linker sequence is either a natural linker sequence, a terminal sequence obtained from naturally occurring domain linking sequences, e.g. hinge sequences, or of naturally linked domains of a naturally occurring immunoglobulin structure, e.g. the C-terminal amino acid region of 1-20, or 2-10, or 3-8 amino acid length obtained from an antibody domain that is naturally linked to the N-terminus of the $CH3_{HET}$ domain, e.g. the C-terminal region of a CH2 domain, can be used as a linker connecting to the N-terminus or to the CH3 domain which is deleted by the N-terminal region of 1-20, or 2-10, or 3-8 amino acid length to provide an N-terminally shortened CH3 sequence. Alternatively, a functionally suitable artificial sequence may be used as a linker. Specifically, the N-terminus of the $CH3_{HET}$ domain may be the natural N-terminus, or the N-terminus of the N-terminally shortened or extended CH3 sequence, which is linked to the C-terminus of the a C-terminally shortened or extended second domain.

The term "multivalent" with respect to an antibody as described herein shall refer to a molecule having at least two binding sites to bind the same target antigen, specifically binding the same or different epitopes of such target antigen. The term shall include bivalent antibodies or molecules with 2 or more valencies to bind the target antigen, e.g. through at least 2, 3, 4 or even more binding sites. For example, a bivalent antibody may have two antigen-binding sites through two pairs of VH/VL domains, both binding the same target antigen.

The term "multispecific" with respect to an antibody as described herein shall refer to a molecule having at least two binding sites specifically binding at least two different target antigens. The term shall include bispecific antibodies or molecules with 2 or more specificities to bind more than one target antigen, e.g. through at least 2, 3, 4 or even more binding sites. For example, a bispecific antibody may bind one target antigen through one pair of VH/VL domains (Fv region), and another target antigen by a second pair of VH/VL domains (Fv region).

The term "antigen" or "target" as used according to the present invention shall in particular include all antigens and target molecules capable of being recognised by a binding site of an antibody. Specifically preferred antigens as targeted by the molecule according to the invention are those antigens or molecules, which have already been proven to be or are capable of being immunologically or therapeutically relevant, especially those, for which a clinical efficacy has been tested. The term "target" or "antigen" as used herein shall in particular comprise molecules selected from the group consisting of (human or other animal) tumor associated receptors and soluble tumor associated antigens, which are self antigens, such as receptors located on the surface of tumor cells or cytokines or growth factors that are abundantly present in the circulation of cancer patients and associated with such tumor. Further antigens may be of pathogen origin, e.g. microbial or viral pathogens.

The target antigen is either recognized as a whole target molecule or as a fragment of such molecule, especially substructures, e.g. a polypeptide or carbohydrate structure of targets, generally referred to as "epitopes", e.g. B-cell epitopes, T-cell epitope), which are immunologically relevant, i.e., are also recognisable by natural or monoclonal antibodies. The term "epitope" as used herein according to the present invention shall in particular refer to a molecular structure which may completely make up a specific binding partner or be part of a specific binding partner to a binding site of an immunoglobulin of the present invention. The term epitope may also refer to haptens. Chemically, an epitope may either be composed of a carbohydrate, a peptide, a fatty acid, an organic, biochemical or inorganic substance or derivatives thereof and any combinations thereof. If an epitope is a polypeptide, it will usually include at least 3 amino acids, preferably 8 to 50 amino acids, and more preferably between about 10-20 amino acids in the peptide. There is no critical upper limit to the length of the peptide, which could comprise nearly the full length of a polypeptide sequence of a protein. Epitopes can be either linear or conformational epitopes. A linear epitope is comprised of a single segment of a primary sequence of a polypeptide or carbohydrate chain. Linear epitopes can be contiguous or overlapping. Conformational epitopes are comprised of amino acids or carbohydrates brought together by folding of the polypeptide to form a tertiary structure and the amino acids are not necessarily adjacent to one another in the linear sequence. Specifically, epitopes are at least part of diagnostically relevant molecules, i.e. the absence or presence of an epitope in a sample is qualitatively or quantitatively correlated to either a disease or to the health status of a patient or to a process status in manufacturing or to environmental and food status. Epitopes may also be at least part of therapeutically relevant molecules, i.e. molecules which can be targeted by the specific binding domain which changes the course of the disease.

As used herein, the term "specificity" or "specific binding" refers to a binding reaction which is determinative of the cognate ligand of interest in a heterogeneous population of molecules. Thus, under designated conditions (e.g. immunoassay conditions), the immunoglobulin binds to its particular target and does not bind in a significant amount to other molecules present in a sample. The specific binding means that binding is selective in terms of target identity, high, medium or low binding affinity or avidity, as selected. Selective binding is usually achieved if the binding constant or binding dynamics is at least 10 fold different, preferably the difference is at least 100 fold, and more preferred a least 1000 fold.

The term "variable binding region" also called "CDR region" as used herein refers to molecules with varying structures capable of binding interactions with antigens. Those molecules can be used as such or integrated within a larger protein, thus forming a specific region of such protein with binding function. The varying structures can be derived from natural repertoires of binding proteins such as from immunoglobulins or antibodies. The varying structures can as well be produced by randomisation techniques, in particular those described herein. These include mutagenized CDR or non-CDR regions (e.g. structural loop regions of constant antibody domains), loop regions of immunoglobulin variable domains or constant domains, in particular CDR loops of immunoglobulins. Typically, binding structures of the immunoglobulin according to the invention are formed by such variable binding regions.

The term "cytotoxic" or "cytotoxic activity" as used for the purpose of the invention shall refer to any specific molecule directed against cellular antigens that, when bound to the antigen, activates programmed cell death and triggers apoptosis. Specific immunoglobulins are effective by its activity on effector cells resulting in activation of cytotoxic T-cells or cells which mediate antibody-dependent cell cytotoxicity (ADCC), complement dependent cytotoxicity (CDC) and/or cellular phagocytosis (ADCP). Specific antibodies kill antibody-coated target cells by apoptosis inducing programmed cell death and/or by binding to Fc receptors of effector cells mediating ADCC and/or CDC activity.

An antibody of the present invention may or may not exhibit Fc effector function. Fc may recruit complement and aid elimination of a target antigen or a target cell through binding a surface antigen by formation of immune complexes.

Specific antibodies may be devoid of an active Fc moiety or Fc effector function, thus, either composed of antibody domains that do not contain an Fc part of an antibody or that do not contain an Fcgamma receptor binding site, or comprising antibody domains lacking Fc effector function, e.g. by modifications to reduce Fc effector functions, in particular to abrogate or reduce ADCC and/or CDC activity. Alternative antibodies may be engineered to incorporate modifications to increase Fc effector functions, in particular to enhance ADCC and/or CDC activity.

Such modifications may be effected by mutagenesis, e.g. mutations in the Fcgamma receptor binding site or by derivatives or agents to interfere with ADCC and/or CDC activity of an antibody format, so to achieve reduction or increase of Fc effector function.

The term "antigen-binding site" or "binding site" refers to the part of an antibody that participates in antigen binding. The antigen binding site is formed by amino acid residues of the N-terminal variable ("V") regions of the heavy ("H") and/or light ("L") chains, or the variable domains thereof. Three highly divergent stretches within the V regions of the heavy and light chains, referred to as "hypervariable regions", are interposed between more conserved flanking stretches known as framework regions. The antigen-binding site provides for a surface that is complementary to the three-dimensional surface of a bound epitope or antigen, and the hypervariable regions are referred to as "complementarity-determining regions", or "CDRs." The binding site incorporated in the CDRs is herein also called "CDR binding site".

The term "expression" is understood in the following way. Nucleic acid molecules containing a desired coding sequence of an expression product such as e.g. an antibody as described herein, and control sequences such as e.g. a promoter in operable linkage, may be used for expression purposes. Hosts transformed or transfected with these sequences are capable of producing the encoded proteins. In order to effect transformation, the expression system may be included in a vector; however, the relevant DNA may also be integrated into the host chromosome. Specifically the term refers to a host cell and compatible vector under suitable conditions, e.g. for the expression of a protein coded for by foreign DNA carried by the vector and introduced to the host cell.

Coding DNA is a DNA sequence that encodes a particular amino acid sequence for a particular polypeptide or protein such as e.g. an antibody. Promoter DNA is a DNA sequence which initiates, regulates, or otherwise mediates or controls the expression of the coding DNA. Promoter DNA and coding DNA may be from the same gene or from different genes, and may be from the same or different organisms. Recombinant cloning vectors will often include one or more replication systems for cloning or expression, one or more markers for selection in the host, e.g. antibiotic resistance, and one or more expression cassettes.

"Vectors" used herein are defined as DNA sequences that are required for the transcription of cloned recombinant nucleotide sequences, i.e. of recombinant genes and the translation of their mRNA in a suitable host organism.

An "expression cassette" refers to a DNA coding sequence or segment of DNA that code for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct".

Expression vectors comprise the expression cassette and additionally usually comprise an origin for autonomous replication in the host cells or a genome integration site, one or more selectable markers (e.g. an amino acid synthesis gene or a gene conferring resistance to antibiotics such as zeocin, kanamycin, G418 or hygromycin), a number of restriction enzyme cleavage sites, a suitable promoter sequence and a transcription terminator, which components are operably linked together. The term "vector" as used herein includes autonomously replicating nucleotide sequences as well as genome integrating nucleotide sequences. A common type of vector is a "plasmid", which generally is a self-contained molecule of double-stranded DNA that can readily accept additional (foreign) DNA and which can readily be introduced into a suitable host cell. A plasmid vector often contains coding DNA and promoter DNA and has one or more restriction sites suitable for inserting foreign DNA. Specifically, the term "vector" or "plasmid" refers to a vehicle by which a DNA or RNA sequence (e.g. a foreign gene) can be introduced into a host cell, so as to transform the host and promote expression (e.g. transcription and translation) of the introduced sequence.

The term "host cell" as used herein shall refer to primary subject cells transformed to produce a particular recombinant protein, such as an antibody as described herein, and any progeny thereof. It should be understood that not all progeny are exactly identical to the parental cell (due to deliberate or inadvertent mutations or differences in environment), however, such altered progeny are included in these terms, so long as the progeny retain the same functionality as that of the originally transformed cell. The term "host cell line" refers to a cell line of host cells as used for expressing a recombinant gene to produce recombinant polypeptides such as recombinant antibodies. The term "cell line" as used herein refers to an established clone of a particular cell type that has acquired the ability to proliferate over a prolonged period of time. Such host cell or host cell line may be maintained in cell culture and/or cultivated to produce a recombinant polypeptide.

The term "isolated" or "isolation" as used herein with respect to a nucleic acid, an antibody or other compound shall refer to such compound that has been sufficiently separated from the environment with which it would naturally be associated, so as to exist in "substantially pure" form. "Isolated" does not necessarily mean the exclusion of artificial or synthetic mixtures with other compounds or materials, or the presence of impurities that do not interfere with the fundamental activity, and that may be present, for example, due to incomplete purification. In particular, isolated nucleic acid molecules of the present invention are also meant to include those chemically synthesized.

With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

With reference to polypeptides or proteins, such as isolated immunoglobulins, the term "isolated" shall specifically refer to compounds that are free or substantially free of material with which they are naturally associated such as other compounds with which they are found in their natural environment, or the environment in which they are prepared (e g. cell culture) when such preparation is by recombinant DNA technology practiced in vitro or in vivo. Isolated compounds can be formulated with diluents or adjuvants and still for practical purposes be isolated—for example, the polypeptides or polynucleotides can be mixed with pharmaceutically acceptable carriers or excipients when used in diagnosis or therapy.

The term "recombinant" as used herein shall mean "being prepared by or the result of genetic engineering". Alternatively, the term "engineered" is used. For example, a modified immunoglobulin or immunoglobulin domain may be modified to produce a variant by engineering the respective parent sequence to produce an engineered immunoglobulin or domain. A recombinant host specifically comprises an expression vector or cloning vector, or it has been genetically engineered to contain a recombinant nucleic acid sequence, in particular employing nucleotide sequence foreign to the host. A recombinant protein is produced by expressing a respective recombinant nucleic acid in a host. The term "recombinant antibody", as used herein, includes immunoglobulins and in particular antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant antibodies comprise antibodies engineered to include rearrangements and mutations which occur, for example, during antibody maturation.

Once antibodies with the desired structure are identified, such antibodies can be produced by methods well-known in the art, including, for example, hybridoma techniques or recombinant DNA technology.

In the hybridoma method, a mouse or other appropriate host animal, such as a hamster, is immunised to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell.

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

Recombinant monoclonal antibodies can, for example, be produced by isolating the DNA encoding the required antibody chains and transfecting a recombinant host cell with the coding sequences for expression, using well-known recombinant expression vectors, e.g. the plasmids of the invention or expression cassette(s) comprising the nucleotide sequences encoding the antibody sequences. Recombinant host cells can be prokaryotic and eukaryotic cells, such as those described above.

According to a specific aspect, the nucleotide sequence may be used for genetic manipulation to humanise the antibody or to improve the affinity, or other characteristics of the antibody. For example, the constant region may be engineered to more nearly resemble human constant regions to avoid immune response, if the antibody is used in clinical trials and treatments in humans. It may be desirable to genetically manipulate the antibody sequence to obtain greater affinity to the target antigen. It will be apparent to one of skill in the art that one or more polynucleotide changes can be made to the antibody and still maintain its binding ability to the target antigen.

The production of antibody molecules, by various means, is generally well understood. U.S. Pat. No. 6,331,415 (Cabilly et al.), for example, describes a method for the recombinant production of antibodies where the heavy and light chains are expressed simultaneously from a single vector or from two separate vectors in a single cell. Wibbenmeyer et al., (1999, Biochim Biophys Acta 1430(2):191-202) and Lee and Kwak (2003, J. Biotechnology 101:189-198) describe the production of monoclonal antibodies from separately produced heavy and light chains, using plasmids expressed in separate cultures of E. coli. Various other techniques relevant to the production of antibodies are provided in, e.g., Harlow, et al., ANTIBODIES: A LABORATORY MANUAL, Cold Spring Harbor Laboratory Press, Cold Spring Harbor, N.Y., (1988).

Monoclonal antibodies are produced using any method that produces antibody molecules by continuous cell lines in culture. Examples of suitable methods for pre-paring monoclonal antibodies include the hybridoma methods of Kohler et al. (1975, Nature 256:495-497) and the human B-cell hybridoma method (Kozbor, 1984, J. Immunol. 133:3001; and Brodeur et al., 1987, Monoclonal Antibody Production Techniques and Applications, (Marcel Dekker, Inc., New York), pp. 51-63).

The antibody as described herein may be used for administration to treat a subject in need thereof.

The term "subject" as used herein shall refer to a warm-blooded mammalian, particularly a human being or a non-human animal. Thus, the term "subject" may also particularly refer to animals including dogs, cats, rabbits, horses, cattle, pigs and poultry. In particular the antibody of the invention is provided for medical use to treat a subject or patient in need of prophylaxis or treatment of a disease condition. The term "patient" includes human and other mammalian subjects that receive either prophylactic or therapeutic treatment. The term "treatment" is thus meant to include both prophylactic and therapeutic treatment.

Specifically, the antibody of the invention is provided in substantially pure form. The term "substantially pure" or "purified" as used herein shall refer to a preparation comprising at least 50% (w/w), preferably at least 60%, 70%, 80%, 90% or 95% of a compound, such as a nucleic acid molecule or an antibody. Purity is measured by methods appropriate for the compound (e.g. chromatographic methods, polyacrylamide gel electrophoresis, HPLC analysis, and the like).

The term "therapeutically effective amount", used herein interchangeably with any of the terms "effective amount" or "sufficient amount" of a compound, e.g. an immunoglobulin of the present invention, is a quantity or activity sufficient to, when administered to the subject effect beneficial or desired results, including clinical results, and, as such, an effective amount or synonym thereof depends upon the context in which it is being applied.

An effective amount is intended to mean that amount of a compound that is sufficient to treat, prevent or inhibit such diseases or disorder. In the context of disease, therapeutically effective amounts of the immunoglobulin as described herein are specifically used to treat, modulate, attenuate, reverse, or affect a disease or condition that benefits from the interaction of the antibody with its target antigen.

The amount of the compound that will correspond to such an effective amount will vary depending on various factors, such as the given drug or compound, the pharmaceutical formulation, the route of administration, the type of disease or disorder, the identity of the subject or host being treated, and the like, but can nevertheless be routinely determined by one skilled in the art.

The antibody of the invention may specifically be used in a pharmaceutical composition. Therefore, a pharmaceutical composition is provided which comprise an antibody as described herein and a pharmaceutically acceptable carrier or excipient. These pharmaceutical compositions can be administered in accordance with the present invention as a bolus injection or infusion or by continuous infusion. Pharmaceutical carriers suitable for facilitating such means of administration are well-known in the art.

Pharmaceutically acceptable carriers generally include any and all suitable solvents, dispersion media, coatings, isotonic and absorption delaying agents, and the like that are physiologically compatible with an antibody provided by the invention. Further examples of pharmaceutically acceptable carriers include sterile water, saline, phosphate buffered saline, dextrose, glycerol, ethanol, and the like, as well as combinations of any thereof.

In one such aspect, an antibody can be combined with one or more carriers appropriate a desired route of administration, antibodies may be, e.g. admixed with any of lactose, sucrose, starch, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, polyvinyl alcohol, and optionally further tableted or encapsulated for conventional administration. Alternatively, an immunoglobulin may be dissolved in saline, water, polyethylene glycol, propylene glycol, carboxymethyl cellulose colloidal solutions, ethanol, corn oil, peanut oil, cotton-seed oil, sesame oil, tragacanth gum, and/or various buffers. Other carriers, adjuvants, and modes of administration are well known in the pharmaceutical arts. A carrier may include a controlled release material or time delay material, such as glyceryl monostearate or glyceryl distearate alone or with a wax, or other materials well known in the art.

Additional pharmaceutically acceptable carriers are known in the art and described in, e.g. REMINGTON'S PHARMACEUTICAL SCIENCES. Liquid formulations can be solutions, emulsions or suspensions and can include excipients such as suspending agents, solubilizers, surfactants, preservatives, and chelating agents.

Pharmaceutical compositions are contemplated wherein an antibody of the present invention and one or more therapeutically active agents are formulated. Stable formulations of the antibody of the present invention are prepared for storage by mixing said antibody having the desired degree of purity with optional pharmaceutically acceptable carriers, excipients or stabilizers, in the form of lyophilized formulations or aqueous solutions. The formulations to be used for in vivo administration are specifically sterile, preferably in the form of a sterile aqueous solution. This is readily accomplished by filtration through sterile filtration membranes or other methods. The immunoglobulin and other therapeutically active agents disclosed herein may also be formulated as immunoliposomes, and/or entrapped in microcapsules.

Administration of the pharmaceutical composition comprising an antibody of the present invention, may be done in a variety of ways, including orally, subcutaneously, intravenously, intranasally, intraotically, transdermally, mucosal, topically, e.g., gels, salves, lotions, creams, etc., intraperitoneally, intramuscularly, intrapulmonary, vaginally, parenterally, rectally, or intraocularly.

Examplary formulations as used for parenteral administration include those suitable for subcutaneous, intramuscular or intravenous injection as, for example, a sterile solution, emulsion or suspension.

The invention specifically provides for exemplary antibodies as detailed in the examples provided herein. Further antibody variants are feasible, e.g. including functional variants of the exemplified immunoglobulins, e.g. where the Fc is further engineered to improve the structure and function of the molecule, or where antibodies comprising different CDR binding sites or with different specificity are produced, in particular, wherein two different Fv regions are obtained.

The foregoing description will be more fully understood with reference to the following examples. Such examples are, however, merely representative of methods of practicing one or more embodiments of the present invention and should not be read as limiting the scope of invention.

EXAMPLES

Example 1: Construction, Expression, Purification and Characterization of a CH3 Domain Exchange Antibody A CH3 domain exchange antibody may be formed using wild-type CH3 domains or a variety of engineered CH3 domains to replace the CH1 and/or CL domains in the domain-exchanged Fab arm of the antibody, and then assembled into a variety of configurations, as illustrated in part in FIG. 1.

In Example 1 synthetic DNA was generated encoding light and heavy chains of three different domain-exchanged heterodimeric antibodies with the following amino acid characteristics:

Domain-Exchanged Heterodimeric Antibody 1:

Fab Arm 1 and Corresponding Engineered Light and Heavy Chain:

CH1 and CL domains in one Fab arm of the complete antibody were replaced with CH3 domains to create a VL(1)-CH3_HOLE (Y407T) light chain (SEQ ID 1) and a VH(1)-CH3_KNOB (T366Y)-CH2-CH3$_{AG}$ heavy chain (SEQ ID 2). The VL(1) and VH(1) domains together form the Fv of the EGFR-specific antibody hu425 (Matuzumab)[1].

The transition from the VL(1) domain to the CH3 domain in the VL(1)-CH3 chain was formed by 4 amino acid residues of Ckappa sequence RTVA (SEQ ID 49, R being residue 108 of human kappa chain (Kabat EU numbering)), directly followed by the amino acid sequence starting with EPQV (SEQ ID 50, E being residue 345 of human IgG1 heavy chain (Kabat EU numbering)) belonging to the A-strand of the CH3 domain. The CH3 domain sequence ended with QKSLSLS (SEQ ID 51, Q being residue 438 of human IgG1 heavy chain (Kabat EU numbering)) followed by residues GEC (representing the C-terminal residues 212-214 (Kabat EU numbering) of the Ckappa chain).

The transition from the VH(1) domain to the CH3 domain in the VH(1)-CH3-CH2-CH3 chain was such that the J-region (ending with the amino acid sequence VTVSS (SEQ ID 52, the first V being residue 109 of the human VH region)

was followed by 5 residues ASTKG belonging to the human CH1 domain (SEQ ID 53, A being residue 118 of human IgG1 heavy chain (Kabat EU numbering)) directly followed by the amino acid sequence starting with EPQV (SEQ ID 50, E being residue 345 of human IgG1 heavy chain (Kabat EU numbering)) belonging to the A-strand of the CH3 domain. The CH3 domain sequence ended with QKSLSLS (SEQ ID 51, Q being residue 438 of human IgG1 heavy chain (Kabat EU numbering)) followed by residues KSC representing a part of the human heavy chain hinge region (K being residue 218 of human IgG1 heavy chain (Kabat EU numbering)).

The CH3 domain of the VL(1)-CH3 chain was engineered in order to preferentially produce a cognate pair with the CH3 domain that is located C-terminally to the VH(1) domain in the VH(1)-CH3-CH2-CH3 chain, specifically it contained a "hole" mutation Y407T (Kabat EU numbering) according to Ridgway et al 1996, so this chain is more fully designated as VL(1)-CH3_HOLE (Y407T) (SEQ ID 1).

The CH3 domain that is located C-terminally to the VH(1) domain in the VH(1)-CH3-CH2-CH3 chain was engineered in order to preferentially produce a cognate pair with the CH3 domain of the VL(1)-CH3 chain, specifically it contained a "knob" mutation T366Y (Kabat EU numbering) according to Ridgway et al 1996.

The C-terminal CH3 domain of the VH(1)-CH3-CH2-CH3 heavy chain of this antibody was engineered in order to preferentially produce a cognate pair with the C-terminal CH3 domain of the second heavy chain of the antibody. The specific engineering of this CH3 domain was that of an "AG" CH3 domain according to Davis et al. 2010, so this chain is more fully designated as VH(1)-CH3_KNOB (T366Y)-CH2-CH3$_{AG}$ (SEQ ID 2).

The resulting bispecific antibody 1 (BsAb1) is recognizing both targets CD3×EGFR, and is specifically characterized by the following heavy and light chains: H1 (SEQ ID 2), H2 (SEQ ID 4), L1 (SEQ ID 1) and L2 (SEQ ID 3).

Fab Arm 2 and Engineered Heavy Chain

The second half of the heterodimeric antibody was formed by the following chains:

The light chain (SEQ ID 3) encoded the VL sequence of the CD3-specific antibody OKT3 (VL2) and was composed of the sequence encoding VL(2)-CL domain.

The heavy chain (SEQ ID 4) encoded the VH sequence of the CD3-specific antibody OKT3 (VH2) and was composed of the sequence encoding VH(2)-CH1-CH2-CH3$_{GA}$ domains. The C-terminal CH3 domain of this VH(2)-CH1-CH2-CH3$_{GA}$ chain was engineered in order to preferentially produce a cognate pair with the C-terminal CH3 domain of the first heavy chain (VH(1)-CH3-CH2-CH3$_{AG}$) of the antibody. The specific engineering of this CH3 domain was that of a "GA" CH3 domain according to Davis et al. 2010, so this chain is designated as VH(2)-CH1-CH2-CH3$_{GA}$ (SEQ ID 4).

Domain-Exchanged Heterodimeric Antibody 2

This antibody was engineered similarly to the Fab arms in the domain-exchanged heterodimeric antibody 1. However, in the domain-exchanged heterodimeric antibody 2 the OKT3 Fab arm is fused to the heavy chain containing a C-terminal CH3$_{AG}$ domain (VH(2)-CH1-CH2-CH3$_{AG}$ (SEQ ID 5)), whereas the domain-exchanged engineered hu425 Fab arm is fused to the heavy chain containing a C-terminal CH3$_{GA}$ domain (VH(1)-CH3_KNOB (T366Y)-CH2-CH3$_{GA}$ (SEQ ID 6)).

As a result, this bispecific antibody is recognizing both targets CD3×EGFR, and is specifically characterized by the following heavy and light chains: H1 (SEQ ID 6), H2 (SEQ ID 5), L1 (SEQ ID 1) and L2 (SEQ ID 3).

Domain-Exchanged Heterodimeric Antibody 3

This antibody was engineered similarly to the Fab arms as the domain-exchanged heterodimeric antibody 2. In the domain-exchanged heterodimeric antibody 3, the OKT3 Fab arm is fused to the heavy chain containing a C-terminal CH3$_{AG}$ domain and the domain-exchanged engineered hu425 Fab arm is fused to the heavy chain containing a C-terminal CH3$_{GA}$ domain. However, in domain-exchanged heterodimeric antibody 3, a wild type (wt) CH3 domain was exchanged C-terminally to both VL1 and VH1 in the engineered hu425 Fab arm instead of the paired cognate "knob" and "hole" engineered CH3 domains used in domain-exchanged heterodimeric antibodies 1 and 2. Domain-exchanged heterodimeric antibody 3 used sequences VL(1)-CH3$_{wt}$ (SEQ ID 7) and VH(1)-CH3$_{wt}$-CH2-CH3$_{GA}$ (SEQ ID 8) for the hu425 Fab arm.

As a result, this bispecific antibody is recognizing both targets CD3×EGFR, and is specifically characterized by the following heavy and light chains: H1 (SEQ ID 8), H2 (SEQ ID 5), L1 (SEQ ID 7) and L2 (SEQ ID 3).

The synthetic DNAs encoding the described antibody chains were flanked with sequences for restriction enzymes for cloning into the pTT5 mammalian expression vector.

Example 2: Vector Construction for Expression of Human Ig-Like Bispecific Antibody Generation of the three human domain-exchanged heterodimeric antibodies described in Example 1 is done by expression of combinations of four different genes within one cell, following the specific combinations of gene sequences as specified in the table below. Generation of domain-exchanged heterodimeric antibody 1 is by co-expression of SEQ ID 1, 2, 3 and 4. Generation of domain-exchanged heterodimeric antibody 2 is by co-expression of SEQ ID 1, 3, 5 and 6. Generation of domain-exchanged heterodimeric antibody 3 is by co-expression of SEQ ID 3, 5, 7, and 8.

|  |  |  | Domain-exchanged heterodimeric antibody | | |
|---|---|---|---|---|---|
|  |  |  | 1 | 2 | 3 |
| Fab arm 1 | Light chain 1 | | VL(1)-CH3_HOLE (Y407T) (SEQ ID No. 1) | VL(1)-CH3_HOLE (Y407T) (SEQ ID No. 1) | VL1-CH3$_{wt}$ (SEQ ID No. 7) |
|  | Heavy chain 1 | | VH(1)-CH3_KNOB (T366Y)-CH2-CH3$_{AG}$ (SEQ ID No. 2) | VH(1)-CH3_KNOB (T366Y)-CH2-CH3$_{GA}$ (SEQ ID No. 6) | VH1-CH3$_{wt}$-CH2-CH1-CH3$_{GA}$ (SEQ ID No. 8) |
| Fab arm 2 | Light chain 2 | | VL(2)-CL (SEQ ID No. 3) | VL(2)-CL (SEQ ID No. 3) | VL(2)-CL (SEQ ID No. 3) |
|  | Heavy chain 2 | | VH(2)-CH1-CH2-CH3$_{GA}$ (SEQ ID No. 4) | VH2-CH1-CH2-CH3$_{AG}$ (SEQ ID No. 5) | VH2-CH1-CH2-CH3$_{AG}$ (SEQ ID No. 5) |

To express these sequences eight different mammalian pTT5 (Shi et al. 2005) based expression vectors were constructed each containing one of the genes encoding:

```
SEQ ID 1:
VL(1)-CH3_HOLE (Y407T)

SEQ ID 2:
VH(1)-CH3_KNOB (T366Y)-CH2-CH3_AG

SEQ ID 3:
VL(2)-CL

SEQ ID 4:
VH(2)-CH1-CH2-CH3_GA

SEQ ID 5:
VH(2)-CH1-CH2-CH3_AG

SEQ ID 6:
VH(1)-CH3_KNOB (T366Y)-CH2-CH3_GA

SEQ ID 7:
VL(1)-CH3wt

SEQ ID 8:
VH(1)-CH3wt-CH2-CH3_GA
```

For VL1 and VH1 the variable domains of the anti-EGFR antibody Matuzumab (hu425) (Kim, 2004) were used.

For VL2 and VH2 the variable domains of the anti-CD3 antibody OKT3 (Van Wauwe et al. 1980) were used.

FIG. 1A illustrates schematically the structures of several of the possible domain-exchanged bispecific antibodies that achieve heterodimerization of the two different heavy chains with the strand-exchange engineered domain (SEED) CH3 heterodimer technology, using AG and GA versions of the CH3 domains (see Davis et al. 2010 and Patent US 20070287170 A1). FIG. 1A-1 specifically illustrates the structure of domain-exchanged heterodimeric antibody 1 of Example 1.

Example 3: Expression and Characterization of Bispecific Antibodies

The domain-exchanged heterodimeric antibodies 1, 2, and 3 described in Examples 1 and 2 were expressed in mammalian cells in small scale according to standard techniques. The resulting proteins were purified by Protein A affinity chromatography and characterized by non-reducing SDS-polyacrylamide gel electrophoresis (SDS-PAGE) and analytical size exclusion chromatography (SEC) (FIG. 2). The non-reducing gel showed predominantly a single band with a molecular weight corresponding to the expected size for both domain-exchanged antibody 1 and 2 (FIG. 2A). For the domain-exchanged antibody 3 SDS-PAGE showed the band of the expected size and showed additional bands corresponding to higher molecular weight protein complexes (FIG. 2A).

These purified proteins were further characterized by analytical SEC showing a main peak eluting from the SEC column after ~7.5 min (similar to the expected elution time for standard IgG antibodies) for domain-exchanged antibodies 1, 2 and 3, with minor contamination by other protein species for domain-exchanged antibodies 1 and 2 (FIGS. 2B and 2C) and additional peaks for antibody 3 (FIG. 2D). Thus use of a domain-exchanged Fab arm produced proteins the expected size of the bispecific antibodies. Next, we proceeded to perform extensive biochemical and functional characterization and testing with a variety of bispecific antibodies formed with domain-exchanged Fab arms.

Example 4: Expression and Characterization of Domain-Exchanged Bispecific Antibody 1 in Large Scale Domain-exchanged heterodimeric bispecific antibodies 1 and 2 have similar biophysical characteristics, e.g. similar non-reducing SDS-PAGE pattern and SEC profiles. Expression of domain-exchanged heterodimeric bispecific antibody 1 yielded higher expression levels and was chosen for further characterizations.

Domain-exchanged heterodimeric bispecific antibody 1 was expressed in mammalian cells according to standard techniques by co-expression of SEQ ID 1, 2, 3 and 4 genes in larger scale (300 mL culture medium). The resulting protein was purified by Protein A affinity chromatography and from this point on this specific domain-exchanged heterodimeric bispecific antibody will be called BsAb1, with the understanding from the preceeding Examples that this is the domain-exchanged antibody composed by co-expression of SEQ ID 1, 2, 3 and 4. Purified BsAb1 (anti-CD3× anti-EGFR CH3-KiH) was characterized by non-reducing and reducing SDS-PAGE and analytical SEC (FIG. 3).

The non-reduced SDS-PAGE showed predominantly a single band with a molecular weight corresponding to the expected size of BsAb1. When the samples were reduced before SDS-PAGE, the profile showed the band labeled H1 band corresponding to VH(1)-CH3_Knob (T366Y)-CH2-CH3_AG (SEQ ID 2), H2 band corresponding to VH(2)-CH1-CH2-CH3_GA (SEQ ID 4) and L1+L2 band corresponding to VL(1)-CH3_Hole (Y407T) (SEQ ID 1) and VL(2)-CL (SEQ ID 3) (FIG. 3A).

Furthermore the purified protein characterized by analytical SEC showed a main peak of >90% eluting from the column after ~7.5 min, which is comparable to elution of standard IgG antibodies (FIG. 3B).

Example 5: Bispecific Binding Assay

To test simultaneous binding of BsAb1 (anti-CD3× anti-EGFR CH3-KiH) to the two antigens CD3 and EGFR, CD3+ Jurkat cells were first stained with BsAb1 or with control bispecific anti-CD3 anti-EGFR antibody followed by an incubation step with EGFR. Bispecific binding was detected with fluorescein isothiocyanate labeled anti-EGFR detection antibody and analyzed by flow cytometry (FIG. 4).

Example 6: Generation and Characterization of One-Armed Antibody Containing CH3 Domain in the Fab Arm One-armed antibodies containing either the CH3 domain-exchanged (KiH cognate pair) or the unengineered Fab region were generated by co-expression of three different genes. FIG. 5 illustrates schematically the structure of the one-armed antibody (unengineered and domain-exchanged). The different mammalian pTT5 based expression vectors containing the gene encoding each antibody chain were constructed as previously described.

Generation of the human domain-exchanged one-armed antibody is done by co-expression of the three different genes encoding the amino acid sequences given in SEQ ID 1, SEQ ID 2 and SEQ ID 9 (huFc_GA SEED) within one cell. The unengineered one-armed antibody was generated by co-expression of the three different genes encoding the amino acid sequences given in SEQ ID 9, SEQ ID 10 (VL(1)-CL) and SEQ ID 11 (VH(1)-CH1-CH2-CH3$_{AG}$).

For VL1 and VH1 the variable domains of the anti-EGFR antibody Matuzumab (hu425) (Kim, 2004) were used.

The resulting one-armed antibodies recognize EGFR, and are specifically characterized by the following light and heavy chains. Domain-exchanged one-armed anti-EGFR: H1 (SEQ ID 2), H2 (SEQ ID 9), and L1 (SEQ ID 1). Unengineered one-armed anti-EGFR: H1 (SEQ ID 11), H2 (SEQ ID 9), and L1 (SEQ ID 10).

Both antibodies were expressed in mammalian cells according to standard techniques. The resulting proteins were purified by protein A affinity chromatography and characterized by non-reducing and reducing SDS-PAGE and analytical SEC (FIG. 6). The non-reducing gel showed predominantly a single band with a molecular weight corresponding to the one-armed antibody. When the samples were reduced before SDS-PAGE, the profile of one-armed antibody (CH1/CL) shows H1 band corresponding to VH(1)-CH1-CH2-CH3$_{AG}$ (SEQ ID 11), H2 band that corresponds to huFc_GA SEED (SEQ ID 9) and L1 band that corresponds to VL(1)-CL (SEQ ID 10) (FIG. 6A). The reduced profile of the domain-exchanged antibody shows H1 band corresponding to VH(1)-CH3_KNOB (T366Y)-CH2-CH3$_{AG}$ (SEQ ID 2), H2 band that corresponds to huFc_GA SEED (SEQ ID 9) and L1 band that corresponds to VL(1)-CH3_HOLE (Y407T) (SEQ ID 1) (FIG. 6A). When the purified proteins were characterized by analytical SEC they both showed a main peak of >90% eluting from the column after ~8 min (FIG. 6B).

Example 7: Monovalent Binding to EGFR-Positive Cells by Flow Cytometry

The one-armed antibody employing the CH3 domain-exchanged anti-EGFR Fab domain was tested for target binding and compared to the one-armed antibody with unengineered anti-EGFR Fab (CH1/CL) (see Example 6). In addition, BsAb1 (anti-CD3× anti-EGFR CH3-KiH) was tested for EGFR target binding. Binding of the antibodies to EGFR-expressing A431 cells was measured by flow cytometry (FIG. 7). Antibodies bound to the cells were detected by an anti-human Fc F(ab)2 secondary antibody conjugated with phycoerythrin and cells were analyzed using flow cytometry. The half maximal effective concentration (EC50) for cell-binding was calculated from the binding curves using the program Graph Pad PRISM.

One-armed CH3 domain-exchanged anti-EGFR antibody and BsAb1 antibody showed dose-dependent binding to EGFR-positive cells with similar binding properties as the control antibody (unengineered Fab one-armed anti-EGFR) (FIG. 7). The EC50 of the one-armed antibodies were in the range of 5-8 nM. BsAb1 bound to EGFR-positive cells with an EC50 of ~7 nM and was comparable to the control antibody (FIG. 7).

These results show that the replacement of CH1/CL by engineered CH3 domains did not change the antigen binding of the respective Fab fragments.

Example 8: Construction, Expression, Purification and Characterization of Domain-Exchanged Bispecific Antibody 2 "BsAb2" (Anti-CD16× Anti-EGFR)

The CH3 domain-exchanged anti-EGFR Fab described in the preceeding Examples and used in BsAb1, was combined with the murine anti-CD16 antibody 3G8 (Fleit et al. 1982) to generate a new domain-exchanged bispecific antibody named from this point on as BsAb2 (anti-CD16× anti-EGFR CH3-KiH). Two additional mammalian pTT5 based expression vectors were constructed each containing one of the genes encoding:

```
SEQ ID 12:
VL(3)-CL

SEQ ID 13:
VH(3)-CH1-CH2-CH3_GA
```

For VL(3) and VH(3) the variable domains of the anti-CD16 antibody 3G8 (Fleit et al. 1982) were used.

The resulting BsAb2 recognizes both targets CD16× EGFR, and is specifically characterized by the following heavy and light chains: H1 (SEQ ID 2), H2 (SEQ ID 13), L1 (SEQ ID 1) and L2 (SEQ ID 12).

Generation of the domain-exchanged bispecific antibody BsAb2 (anti-CD16× anti-EGFR CH3-KiH) is done by expression of the four different genes encoding the amino acid sequences given in SEQ ID 1, SEQ ID 2, SEQ ID 12 and SEQ ID 13 within one cell. Heterodimerization of the two different heavy chains was achieved by the SEED technology as described for BsAb1.

BsAb2 was expressed in mammalian cells according to standard techniques. The resulting protein was purified by Protein A purification, and showed similar homogeneity with expected size and purity as shown for BsAb1 after single-step protein A purification.

To prepare for definitive biochemical verification of the correct assembly of BsAb1 and BsAb2 by mass spectrometertry (see Example 9 in next section), BsAb1 and BsAb2 were further purified in a second purification step using preparative SEC. As an example of the protein purity after this preparative SEC purification step, BsAb2 protein after this second purification by preparative SEC was characterized by non-reducing and reducing SDS-PAGE and analytical SEC (FIG. 8). The non-reducing gel showed predominantly a single band with a molecular weight corresponding to the domain-exchanged BsAb2. When samples were reduced before SDS-PAGE, the profile shows H1 band corresponding to VH(1)-CH3_KNOB (T366Y)-CH2-CH3$_{AG}$ (SEQ ID 2), H2 band that corresponds to VH(3)-CH1-CH2-CH3$_{GA}$ (SEQ ID 13), L2 band that corresponds to VL(3)-CL (SEQ ID 12) and L1 band corresponding to VL(1)-CH3_HOLE (Y407T) (SEQ ID 1) (FIG. 8A). This purified protein was further characterized by analytical SEC and showed a main peak of >90% eluting from the column after ~7.5 min, similar to the elution time of domain-exchanged BsAb1 (anti-CD3× anti-EGFR CH3-KiH) and also of standard IgG antibodies (FIG. 8B).

Example 9: Verification of Correct Assembly by Mass Spectrometry

Direct Approach Analyzing Domain-Exchanged Bispecific Antibodies

In order to confirm the correct chain pairing in the domain-exchanged bispecific antibodies, purified domain-exchanged bispecific antibodies BsAb1 (anti-CD3× anti-EGFR CH3-KiH) and BsAb2 (anti-CD16× anti-EGFR CH3-KiH) were measured by Liquid chromatography-mass spectrometry (LC-MS) analysis. Prior to MS-analysis the samples were deglycosylated by PNGaseF. As shown in FIGS. 9 and 10, a single peak of 148.284 kDa and 148.050 kDa was detected for domain-exchanged bispecific antibody BsAb1 and BsAb2, respectively. These detected masses correspond to the sum of the four different antibody chains. During assembly of these chains, additional mass losses can occur due to the formation of disulfide bridges, cleavage of C-terminal lysine and formation of N-terminal pyroglutamate. Taking these mass losses of ~322 kDa into account, the detected average masses differ by only <3 Da for domain-exchanged bispecific antibody BsAb1 and ~12 Da for domain-exchanged bispecific antibody BsAb2 from the calculated average masses. GA-homodimers were not detected in either antibody sample (calculated molecular massed of homodimer OKT3-GA: 146.465 kDa and of homodimer 3G8-GA: 145.980 kDa).

These results demonstrate assembly in the correct stoichiometry of the 4 different protein chains that were co-expressed in the same cell for production of the domain-exchanged bispecific antibodies.

Indirect Approach by Competing Light Chains

Since the applied LC-MS method was not able to distinguish between correctly assembled domain-exchanged antibody and an antibody with swapped light chains, a competition assay was performed. In this assay, both light chains and one of the heavy chains from a domain-exchanged bispecific antibody were co-expressed with the huFc_GA SEED chain (hinge-CH2-CH3$_{GA}$) within one cell to form a one-armed antibody. If only specific pairing of the correct light chain to the one-armed heavy chain occurred, then only a Fab with the correct light chain paired would be formed. The antibody chains of the domain-exchanged bispecific antibody BsAb1 were chosen as a model.

In competition assay I (FIG. 11), a one-armed antibody containing the CH1/CL domains in the Fab region were generated by co-expressing four different genes encoding for VL(1)-CH3_HOLE (Y407T) (SEQ ID 1), VL(2)-CL (SEQ ID 3), VH(2)-CH1-CH2-CH3$_{AG}$ (SEQ ID 5) and huFc_GA SEED (SEQ ID 9). In competition assay II (FIG. 12), a one-armed antibody containing the CH3-domain-exchanged Fab region was generated by co-expressing four different genes encoding for VL(1)-CH3_HOLE (Y407T) (SEQ ID 1), VL(2)-CL (SEQ ID 3), VH(1)-CH3_KNOB (T366Y)-CH2-CH3$_{AG}$ (SEQ ID 2) and huFc_GA Seed (SEQ ID 9). Antibodies were expressed in mammalian cells according to standard techniques. After protein A purification, the proteins were deglycosylated by PNGaseF and subsequently analyzed by LC-MS. Main peaks at 99.521 kDa (FIG. 11) and 101.387 kDa (FIG. 12) were detected in competition assay I and II, respectively. These detected masses correspond to the correctly assembled one-armed unengineered antibody in competition assay I and to the domain-exchanged one-armed antibody in competition assay II. Additional peaks corresponding to the mispaired variants could not be found.

These results show that the CH3 domain-exchange engineering enforces correct light-to-heavy chain pairing.

Example 10: Thermal Stability of Domain-Exchanged Antibodies

The stability of the domain-exchanged bispecific antibodies BsAb1 and 2 were additionally analyzed by different scanning calorimetry (DSC) and the melting temperature of apparent transitions were determined (see FIG. 13).

Both domain-exchanged bispecific antibodies unfold with three apparent transitions. The first transition of the domain-exchanged bispecific antibody 1 and 2 was observed at Tm1=61.3° C. and Tm1=61.9° C., respectively. This transition corresponds to the thermal unfolding of the domain-exchanged anti-EGFR Fab domain. The second peak at Tm2=67.3° C. for the domain-exchanged bispecific antibody 1 and Tm2=67.4° C. for the domain-exchanged bispecific antibody 2 correspond to the unfolding of the AG/GA SEED Fc fragment. The third transition at Tm3=71.8° C. for domain-exchanged bispecific antibody 1 and Tm3=71.1° C. for domain-exchanged bispecific antibody 2 corresponds to the unfolding of the native Fab domain (anti-CD3 or anti-CD16).

Example 11: Generation and Characterization of Effector Negative Antibodies

In addition to the bispecific and one-armed antibodies described in previous examples, new antibodies listed below were generated to be used for the next set of experiments, following the same protein expression, purification and characterization procedures described in the Examples above for antibody generation.

One-armed anti-CD3 with the unengineered OKT3 Fab fused to the SEED AG heavy chain One-armed anti-CD16 with the unengineered 3G8 Fab fused to the SEED AG heavy chain Effector Negative (EN) isotype one-armed anti-EGFR with the CH3 domain-exchanged (KiH cognate pair) hu425 Fab fused to the EN isotype SEED AG heavy chain, paired with EN isotype huFc_GA SEED chain Effector Negative (EN) isotype domain-exchanged bispecific antibody BsAb2 (anti-CD16× anti-EGFR CH3-KiH) generated as in Example 8, but using EN isotype SEED AG and EN isotype SEED GA heavy chains The Effector Negative (EN) isotype SEED chains were generated based on the EN human IgG2 variant sequence described in U.S. Pat. No. 8,562,986 and adapted for use with SEED heavy chains as follows.

To produce EN huFc_SEED chains (where huFc is composed of the specified human hinge-CH2-CH3 sequences), from the EN IgG2 variant sequence (U.S. Pat. No. 8,562,986) the modified human IgG1 hinge (C220S) and modified human IgG2 CH2 domain (F296A, N297Q) were fused to the N-terminus of either the SEED "AG" or "GA" CH3 domains (Davis et al. 2010) to produce EN isotype huFc_AG SEED or EN isotype huFc_GA SEED chains. For example, huFc_g1hingeEN-CH2$_{EN}$-CH3$_{GA}$ (SEQ ID 16).

The domain-exchanged Fab does not have a CH1 sequence, so the IgG2 CH1 could not be used in the EN domain-exchanged heavy chain and the light-chain covalent attachment site naturally present in wild-type IgG2 CH1 was not present. Therefore to produce the EN domain-exchanged anti-EGFR "AG" SEED heavy chain, wild-type human IgG1 hinge sequence was used together with the modified human IgG2 CH2 domain (F296A, N297Q) described in U.S. Pat. No. 8,562,986, as shown in VH(1)-CH3_KNOB (T366Y)-CH2$_{EN}$-CH3$_{AG}$ (SEQ ID 15). This design was also used to produce an EN unengineered 3G8 Fab GA SEED heavy chain for use in the bispecific antibody "BsAb2 EN" (see below), as shown in VH(3)-CH1-CH2$_{EN}$-CH3$_{GA}$ (SEQ ID 17).

Additional mammalian pTT5 based expression vectors were constructed each containing one of the genes encoding:

```
SEQ ID 14:
VH(3)-CH1-CH2-CH3_AG

SEQ ID 15:
VH(1)-CH3_KNOB (T366Y)-CH2_EN-CH3_AG
```

```
SEQ ID 16:
huFc_g1hingeEN-CH2_EN-CH3_GA

SEQ ID 17:
VH(3)-CH1-CH2_EN-CH3_GA
```

For VL1 and VH1 the variable domains of the anti-EGFR antibody Matuzumab (hu425) (Kim, 2004) were used.

For VL2 and VH2 the variable domains of the anti-CD3 antibody OKT3 (Van Wauwe et al. 1980) were used.

For VL(3) and VH(3) the variable domains of the anti-CD16 antibody 3G8 (Fleit et al. 1982) were used.

Generation of the antibodies is done by expression of the different genes encoding the amino acid sequences within one cell. Heterodimerization of the two different heavy chains was achieved by the SEED technology as described for BsAb1 in earlier Examples.

One-armed anti-CD3 with the unengineered OKT3 Fab fused to the SEED AG heavy chain was generated by co-expressing the 3 different genes encoding for VL(2)-CL (SEQ ID 3), VH(2)-CH1-CH2-CH3$_{AG}$ (SEQ ID 5) and huFc_GA SEED (SEQ ID 9).

One-armed anti-CD16 with the unengineered 3G8 Fab fused to the SEED AG heavy chain was generated by co-expressing the 3 different genes encoding for VL(3)-CL (SEQ ID 12), VH(3)-CH1-CH2-CH3$_{AG}$ (SEQ ID 14), and huFc_GA SEED (SEQ ID 9).

One-armed Effector Negative (EN) domain-exchanged anti-EGFR was generated by co-expressing the 3 different genes encoding VL(1)-CH3_HOLE (Y407T) (SEQ ID 1), VH(1)-CH3_KNOB (T366Y)-CH2$_{EN}$-CH3$_{AG}$ (SEQ ID 15) and huFc_g1hingeEN-CH2$_{EN}$-CH3$_{GA}$ (SEQ ID 16) within one cell.

The resulting one-armed EN antibody is recognizing EGFR, and is specifically characterized by the following light and heavy chains: H1 (SEQ ID 15), H2 (SEQ ID 16), and L1 (SEQ ID 1).

Effector Negative (EN) isotype domain-exchanged bispecific antibody BsAb2 (anti-CD16× anti-EGFR CH3-KiH), to be called "BsAb2 EN" from this point on, was generated by co-expressing the 4 different genes coding for VL(1)-CH3_HOLE (Y407T) (SEQ ID 1), VH(1)-CH3_KNOB (T366Y)-CH2$_{EN}$-CH3$_{AG}$ (SEQ ID 15), VL(3)-CL (SEQ ID 12), and VH(3)-CH1-CH2$_{EN}$-CH3$_{GA}$ (SEQ ID 17) within one cell.

The resulting EN BsAb2 is recognizing both targets CD16×EGFR, and is specifically characterized by the following heavy and light chains: H1 (SEQ ID 15), H2 (SEQ ID 17), L1 (SEQ ID 1) and L2 (SEQ ID 12).

Many antibody effector functions are mediated by antibodies binding to Fcγ receptors on immune cells through a binding site in the Fc portion of antibodies. A specific example is the effector function Antibody Dependent Cellular Cytotoxicity (ADCC), which is mediated by the binding of antibodies to CD16a (FcγIIIa) on immune effector cells via the Fcγ receptor binding site in the Fc portion of antibodies. Effector Negative isotype antibodies are deficient in binding to CD16a via their Fc.

Binding of antibodies to the CD16a receptor (FcγIIIa) was determined by a CD16a Cellular Binding Assay Kit (CisBio) (FIG. 14). In this assay antibodies are tested for their ability to compete for binding of a fluorescently labeled human IgG to CD16a. If an unlabeled test antibody binds to CD16a, it will compete with binding of the labeled IgG, and this competition will decrease the measured binding signal.

Effector-competent antibodies with an anti-CD16 Fab arm are expected to bind to the CD16a receptor via both the anti-CD16 Fab arm and by the Fcγ receptor binding site in the Fc portion of this antibody. Effector Negative isotype antibodies will not bind to CD16a through the Fcγ receptor binding site in the Fc portion.

As expected, no binding to CD16a receptor was detected for the one-armed domain-exchanged EN anti-EGFR antibody, resulting in no decrease in the measured signal (FIG. 14, inverted triangles). The other antibodies showed dose-dependent binding to the CD16a receptor, resulting in inhibition of the measured signal with different half-maximal inhibitory concentration (IC50). The weakest CD16-binding was observed for the one-armed anti-EGFR antibodies, with either unengineered CH1/CL Fab or domain-exchanged CH3-KiH Fab (FIG. 14, diamonds). Their binding was in the range of 23-71 nM. As expected the BsAb2 and the one-armed anti-CD16 antibody showed the strongest binding to CD16a (FIG. 14, circles and triangles, respectively). Binding was in the range of 0.3 nM for BsAb2 and 0.1 nM for the one-armed anti-CD16 antibody. The effector negative IgG2 variant of BsAb2, "BsAb2 EN" (FIG. 14, squares), showed weaker CD16-binding (IC50 ~3.6 nM) compared to BsAb2, but a stronger binding compared to the monovalent anti-EGFR antibodies.

These results suggest that BsAb2 is able to bind CD16a receptor via both the anti-CD16 Fab arm and the Fcγ receptor binding site in the Fc portion of the antibody, while BsAb2 EN can still bind to CD16a, but with weaker binding mediated only through the anti-CD16 Fab arm. Furthermore, this single anti-CD16 Fab arm binding to CD16a with BsAb2 EN was stronger than the binding to CD16a that occurred only through the Fcγ receptor binding site in the Fc of monovalent anti-EGFR antibodies.

Example 12: Functional Activity of Domain-Exchanged Antibodies

To test functional cytotoxicity of the domain-exchanged bispecific antibodies BsAb1 and BsAb2, activated primary T cells or NK cells were incubated with EGFR-overexpressing A431 cells in the presence of antibodies applied in serial dilution. Cell lysis was measured by lactate dehydrogenase (LDH) release, a cell death indicator released to the supernatant upon cell lysis, using CYTOTOX® 96 Non-Radioactive Cytotoxicity Assay (Promega) after co-cultivation of effector and target cells with E:T ratio 10:1. Co-cultivation was performed 18 h for activated T cells and 4 h for NK cells.

Dose-dependent redirected cell lysis of target cells A431 by activated T-cells was detected in the presence of the domain-exchanged bispecific antibody BsAb1 (as seen in FIG. 15A). As expected, one-armed anti-CD3 antibody, one-armed domain-exchanged anti-EGFR antibody and the negative control one-armed anti-CD16 antibody, showed no redirected T-cell lysis of target cells. Only the domain-exchanged bispecific antibody BsAb 1 showed up to 50% cell lysis with a calculated EC50 value between 0.1-0.3 nM.

This redirected T-cell lysis demonstrates that both arms of the domain-exchanged bispecific antibody BsAb1 (anti-CD3× anti-EGFR CH3-KiH) are functional, and simultaneously engage the 2 targets CD3 and EGFR to redirect T-cells to lyse the A431 target cells.

Domain-exchanged bispecific antibody BsAb2 (anti-CD16× anti-EGFR CH3-KiH) and its effector negative (EN) variant BsAb2 EN both showed dose-dependent cell lysis of A431 cells by redirected NK cells (FIG. 15B). Both variants were able to lyse up to 50% of the target cells. The calculated EC50 value of the domain-exchanged bispecific EN variant of BsAb2 EN was 37 pM and the EC50 value of the effector positive BsAb2 variant was 10 pM.

In comparison, the one-armed domain-exchanged anti-EGFR antibody also showed dose-dependent target cell lysis due to the natural engagement of NK cells through the Fcγ receptor binding site in the Fc part of this one-armed antibody, even though it does not have an anti-CD16 arm. The one-armed effector negative anti-EGFR antibody showed no cells lysis due to the lack both of Fcγ Receptor binding by the effector negative IgG2 variant isotype Fc and lack of an anti-CD16 arm. As expected the negative control anti-CD3 antibody also showed no cells lysis.

The redirected NK cell lysis of A431 cells by the effector negative variant domain-exchanged bispecific antibody BsAb2 EN (anti-CD16× anti-EGFR CH3-KiH) showed that both arms of BsAb2 are functional, and simultaneously engage the 2 targets CD16 and EGFR to redirect NK-cells to lyse the A431 target cells.

Altogether, these results show that the domain-exchange bispecific antibody format produced bispecific antibodies that could simultaneously engage both targets with each Fab arm, and demonstrated biological function of these antibodies dependent on binding to the 2 different targets.

Example 13: Examples of Combinations of Engineered CH3 Domains

As illustrated in part in FIG. 1, there are many combinations and variations to use different engineered CH3 domains to form domain-exchange bispecific antibodies. Below is a summary table listing several of the possible examples of combinations of engineered CH3 domains in Fc (i.e. the $CH3_{HC}/CH3_{HC}$ domain pair) and CH3 domain-exchanged Fab (i.e. the $CH3_{LC}/CH3_{HC}$ domain), see FIGS. 1A-1D.

| | Combinations of engineered CH3 domains as examples of embodiments | | | | |
|---|---|---|---|---|---|
| | | Fab CH3 exchange domains | | | |
| Fc Domains | wt-CH3 | Knobs-into-holes | Gunasekaran et al. | Von Kreudenstein et al. | SEED |
| SEED | X | X | X | X | (◯) |
| Knobs-into-holes | X | (◯) | X | X | X |
| Gunasekaran et al. | X | X | (◯) | X | X |
| Von Kreudenstein et al. | X | X | X | (◯) | X |

CH1/CL domains in one Fab arm of a one-armed antibody were replaced with alternative engineered CH3 domains. These alternative engineered CH3 domains are usually used to enforce heavy chain heterodimerization in heterodimeric Fc molecules. As a model the anti-EGFR hu425 Fab domain was chosen to be used for VH(1) and VL(1). DNA sequences encoding alternative CH3 domains were synthesized and different mammalian pTT5 based expression vectors were constructed each containing one of the genes encoding:

"KiH2" CH3 domains (Ridgway et al. (1996), Atwell et al. (1997))

Variant 1:
SEQ ID 18:
VH(1)-CH3_KNOB (T366W)-CH2-CH3$_{AG}$

SEQ ID 19:
VL(1)-CH3_HOLE (T366S, L368A, Y407V

Variant 2:
SEQ ID 20:
VH(1)-CH3_HOLE (T366S, L368A, Y407V)-CH2-CH3$_{AG}$

SEQ ID 21:
VL(1)-CH3_KNOB (T366W)

"Charge pair" CH3 domains (Gunasekaran et al. (2010)

Variant 1:
SEQ ID 22:
VH(1)-CH3 (E356K, D399K)-CH2-CH3$_{AG}$

SEQ ID 23:
VL(1)-CH3 (K392D, K409D)

Variant 2:
SEQ ID 24:
VH(1)-CH3 (K392D, K409D)-CH2-CH3$_{AG}$

SEQ ID 25:
VL(1)-CH3 (E356K, D399K)

"Azymetric" CH3 domains (Von Kreudenstein et al. (2013))

Variant 1:
SEQ ID 26:
VH(1)-CH3 (T350V, L351Y, F405A, Y407V)-CH2-CH3$_{AG}$

SEQ ID 27:
VL(1)-CH3 (T350V, T366L, K392L, T394W)

Variant 2:
SEQ ID 28:
VH(1)-CH3 (T350V, T366L, K392L, T394W)-CH2-CH3$_{AG}$

SEQ ID 29:
VL(1)-CH3 (T350V, L351Y, F405A, Y407V

"SEED" CH3 domains (Davis et al. (2010))

Variant 1:
SEQ ID 30:
VH(1)-CH3_SEED (AG)-CH2-CH3$_{AG}$

SEQ ID 31:
VL(1)-CH3_SEED (GA)

-continued

```
Variant 2:
SEQ ID 32:
VH(1)-CH3_SEED (GA)-CH2-CH3_AG

SEQ ID 33:
VL(1)-CH3_SEED (AG)
```

One-armed antibodies and bispecific antibodies (anti-CD3× anti-EGFR) were produced in mammalian cells. For the one-armed domain-exchange Fab antibodies with alternative CH3 domain, 3 genes encoding for the 2 amino acid sequences given in the list above in addition to the huFc_GA (SEQ ID 9) were expressed. The domain-exchange bispecific antibodies containing these alternative CH3-exchanged domains were generated by expression of 4 genes encoding for the 2 amino acid sequences given in the list above in addition to the 2 amino acid sequences given in SEQ ID 3 and SEQ ID 4. Proteins were purified by protein A from cell culture media by standard methods and characterized by SDS-PAGE and analytical SEC.

One-Armed Antibodies with Alternative CH3 Domains

The non-reducing SDS-PAGE showed predominantly a single band with a molecular weight corresponding to the domain-exchanged one-armed antibodies (FIG. 16A). No significant differences between variant 1 and variant 2 were observed. The hu425 CH3-Azymmetric variant showed a different mobility of the full assembled one-armed antibody seen in a main band of ~90 kDa. Analytical SEC showed a main peak with a retention time of ~7.9 min for all variants and to varying degrees additional peaks (FIG. 16C). An additional peak of high molecular weight species (retention time of 6.7 min) was most prominent for the one-armed antibody containing the CH3-SEED domain in both the Fab arm and the Fc region of the antibody. This could suggest there is more chance for mispairing when the same engineered CH3 domain is used in both the domain-exchanged Fab arm and the Fc region of the antibody.

Alternative Domain-Exchanged Bispecific Antibodies

The non-reducing SDS-PAGE showed predominantly one major band for the alternative CH3 domain-exchanged bispecific antibodies, with minor bands present to varying degrees (FIG. 16B). In SEC analysis, all samples showed a main peak with a retention time of ~7.5 min and a side peak with a retention time of ~8 min (FIG. 16D). Additional high molecular weight species were present to varying degrees.

Binding assays of one-armed domain-exchange antibodies containing alternative CH3 domains The one-armed antibodies comprising the alternatively domain-exchanged Fab domains (variant 1 and 2) were tested for antigen binding using flow cytometry. EGFR-overexpressing A431 cells were incubated with serial dilutions of the tested antibodies (1:3) and binding to the antigen was detected using the anti-human Fc F(ab)2 secondary antibody conjugated with phycoerythrin. The one-armed antibodies comprising the alternatively domain-exchanged Fab domains (variant 1 and 2) showed similar antigen binding properties as the unengineered Fab containing antibody (FIGS. 17A and B). The EGFR-binding for all samples was in an EC50 range of 2-4 nM.

Functional Activity of Domain-Exchanged Bispecific Antibodies

Due to comparable protein characteristics or variants 1 and 2, variant 1 of the domain-exchanged bispecific antibodies were chosen to test for functional activity. Activated T cells were co-cultured with EGFR-overexpressing A431 cells in the presence of tested antibodies in serial dilutions (1:4). Cell lysis was measured by LDH release using CYTO-TOX® 96 Non-Radioactive Cytotoxicity Assay (Promega) after co-cultivation of effector and target cells with E:T ratio 10:1 for 18 h. The domain-exchanged bispecific antibodies with alternative CH3 domains (anti-CD3× anti-EGFR) redirected lysis of EGFR-overexpressing cells by pre-stimulated T cells (FIG. 18). For comparison to the previous Examples, the domain-exchange bispecific antibody BsAb1 (anti-CD3× anti-EGFR CH3-KiH) was also included.

This redirected T-cell lysis demonstrates that both arms of the domain-exchange bispecific antibodies with alternative CH3 domains are functional, and simultaneously engage the 2 targets CD3 and EGFR to redirect T-cells to lyse the A431 target cells.

Example 14: Examples of Combinations of Engineered CH3 Domains for Domain-Exchanged Fabs in Heterodimeric KiH Antibodies CH1/CL domains in one-armed KiH antibodies were replaced with alternative CH3 domains. These alternative CH3 domains were the same as used in Example 13 except KiH domain-exchange. FIG. 19A illustrates schematically the structure of the one-armed KiH antibody with domain-exchange in the Fab arm. As a model the anti-EGFR hu425 Fab domain was chosen to be used for VH(1) and VL(1). DNA sequences encoding alternative CH3 domains were synthesized and six different mammalian pTT5 based expression vectors were constructed each containing one of the genes encoding:

```
SEQ ID 34:
VH(1)-CH3 (E356K, D399K)-CH2-CH3_HOLE (T366S,
L368A, Y407V)

SEQ ID 35:
VH(1)-CH3 (K392D, K409D)-CH2-CH3_HOLE (T366S,
L368A, Y407V)

SEQ ID 36:
VH(1)-CH3 (T350V, L351Y, F405A,
Y407V)-CH2-CH3_HOLE (T366S, L368A, Y407V

SEQ ID 37:
VH(1)-CH3 (T350V, T366L, K392L,
T394W)-CH2-CH3_HOLE (T366S, L368A, Y407V)

SEQ ID 38:
VH(1)-CH3_SEED (AG)-CH2-CH3_HOLE (T366S,
L368A, Y407V)

SEQ ID 39:
VH(1)-CH3_SEED (GA)-CH2-CH3_HOLE (T366S,
L368A, Y407V)
```

Generation of one-armed domain-exchanged KiH antibodies was done by the coexpression of 3 different genes encoding for 3 different antibody chains. The huFc_KNOB (T366W) (SEQ ID 40) was coexpressed with these two genes:

The exemplified one-armed antibody is specifically characterized by a heavy chain H2 identified by SEQ ID 40, and any of the following H1/L1 chain pairs:

Charge pair CH3 domains (Gunasekaran et al. (2010)

```
Variant 1:
SEQ ID 34:
VH(1)-CH3 (E356K, D399K)-CH2-CH3_HOLE (T366S,
L368A, Y407V)

SEQ ID 23:
VL(1)-CH3 (K392D, K409D)

Variant 2:
SEQ ID 35:
VH(1)-CH3 (K392D, K409D)-CH2-CH3_HOLE (T366S,
L368A, Y407V)

SEQ ID 25:
VL(1)-CH3 (E356K, D399K)
```

Azymetric CH3 domains (Von Kreudenstein et al. (2013))

```
Variant 1:
SEQ ID 36:
VH(1)-CH3 (T350V, L351Y, F405A,
Y407V)-CH2-CH3_HOLE (T366S, L368A, Y407V)

SEQ ID 27:
VL(1)-CH3 (T350V, T366L, K392L, T394W)

Variant 2:
SEQ ID 37:
VH(1)-CH3 (T350V, T366L, K392L,
T394W)-CH2-CH3_HOLE (T366S, L368A, Y407V)

SEQ ID 29:
VL(1)-CH3 (T350V, L351Y, F405A, Y407V)
```

SEED CH3 domains (Davis et al. (2010))

```
Variant 1:
SEQ ID 38:
VH(1)-CH3_SEED (AG)-CH2-CH3_HOLE (T366S,
L368A, Y407V)

SEQ ID 31:
VL(1)-CH3_SEED (GA)

Variant 2:
SEQ ID 39:
VH(1)-CH3_SEED (GA)-CH2-CH3_HOLE (T366S,
L368A, Y407V)

SEQ ID 33:
VL(1)-CH3_SEED (AG)
```

One-armed domain-exchanged KiH antibodies were produced in mammalian cells. Proteins were purified by protein A from cell culture media by standard methods and characterized by SEC.

Analytical SEC showed a main peak with a retention time of ~7.9 min and an additional peak with a retention time of ~8.3 min (FIG. 19B). Furthermore, an additional peak of high molecular weight species (retention time of 7.4 min) was observed for the one-armed domain-exchanged antibody containing the CH3-Azymetric. In addition, the one-armed domain-exchanged antibody containing the CH3-SEED showed additional peaks at 5.7 min and 6.8 min of high molecular weight species.

These proteins were further tested for cell binding to EGFR-positive cells using flow cytometry as described in earlier Examples (FIGS. 20 A and B). Although different SEC profiles were obtained for the different one-armed domain-exchanged KiH antibodies, similar antigen binding was observed compared to the one-armed domain-exchange antibody described in Examples 6 and 7, with calculated EC50 values for all antibodies in the range of 3-5 nM.

Altogether, Examples 13 and 14 demonstrate that different combinations of engineered CH3 domains can be used to form domain-exchanged antibodies.

REFERENCES

1. Kollmannsberger C, Schittenhelm M, Honecker F, Tillner J, Weber D, Oechsle K, Kanz L, Bokemeyer C. A phase I study of the humanized monoclonal anti-epidermal growth factor receptor (EGFR) antibody EMD 72000 (matuzumab) in combination with paclitaxel in patients with EGFR-positive advanced non-small-cell lung cancer (NSCLC). Ann Oncol. 2006 June; 17(6):1007-13. Epub 2006 Mar. 13. PubMed PMID:16533873
2. Davis J H, Aperlo C, Li Y, Kurosawa E, Lan Y, Lo K M, Huston J S. SEEDbodies: fusion proteins based on strand-exchange engineered domain (SEED) CH3 heterodimers in an Fc analogue platform for asymmetric binders or immunofusions and bispecific antibodies. Protein Eng Des Sel. 2010 April; 23(4):195-202. doi:10.1093/protein/gzp094. Epub 2010 Feb. 4. PubMed PMID: 20299542.
3. Ridgway J B, Presta L G, Carter P. 'Knobs-into-holes' engineering of antibody CH3 domains for heavy chain heterodimerization. Protein Eng. 1996 July; 9(7):617-21. PubMed PMID: 8844834.
4. Shi C, Shin Y O, Hanson J, Cass B, Loewen M C, Durocher Y. Purification and characterization of a recombinant G-protein-coupled receptor, Saccharomyces cerevisiae Ste2p, transiently expressed in HEK293 EBNA1 cells. Biochemistry. 2005 Dec. 6; 44(48):15705-14. PubMed PMID: 16313173.
5. Kim T. Technology evaluation: Matuzumab, Merck KGaA. Curr Opin Mol Ther. 2004 February; 6(1):96-103. PubMed PMID: 15011787.
6. Van Wauwe J P, De Mey J R, Goossens J G. OKT3: a monoclonal anti-human T lymphocyte antibody with potent mitogenic properties. J Immunol. 1980 June; 124 (6):2708-13. PubMed PMID: 6966296.
7. Gunasekaran K, Pentony M, Shen M, Garrett L, Forte C, Woodward A, Ng S B, Born T, Retter M, Manchulenko K, Sweet H, Foltz I N, Wittekind M, Yan W. Enhancing antibody Fc heterodimer formation through electrostatic steering effects: applications to bispecific molecules and monovalent IgG. J Biol Chem. 2010 Jun. 18; 285(25): 19637-46. doi: 10.1074/jbc.M110.117382. Epub 2010 Apr. 16. PubMed PMID: 20400508.
8. Von Kreudenstein T S, Escobar-Carbrera E, Lario P I, D'Angelo I, Brault K, Kelly J, Durocher Y, Baardsnes J, Woods R J, Xie M H, Girod P A, Suits M D, Boulanger M J, Poon D K, Ng G Y, Dixit S B. Improving biophysical properties of a bispecific antibody scaffold to aid developability: quality by molecular design. MAbs. 2013 September-October; 5(5):646-54. doi: 10.4161/mabs.25632. Epub 2013 Jul. 8. PubMed PMID: 23924797.
9. Martin W L, West A P, Jr., Gan L, Bjorkman P J. Crystal structure at 2.8 A of an FcRn/heterodimeric Fc complex: mechanism of pH-dependent binding. Mol Cell 2001 April; 7(4):867-77. PubMed PMID: 11336709.
10. Fleit H B, Wright S D, Unkeless J C. Human neutrophil Fc gamma receptor distribution and structure. Proc. Natl. Acad. Sci. U.S.A 1982 79.10:3275-79.
11. Atwell S, Ridgway, J B B, Wells J A, Carter P. Stable heterodimers from remodeling the domain interface of a homodimer using a phage display library. J. Mol. Biol. 1997 270.1: 26-35.

The invention claimed is:

1. A bispecific domain-exchanged antibody comprising a first dimer and a second dimer, each dimer comprising a light chain (LC) and a heavy chain (HC), wherein the LC and HC are each formed from antibody domains selected from the group consisting of VL, VH, CL, CH1, CH2, and CH3, comprising:

a) a first LC paired with a first HC to form the first dimer, the first dimer having a first binding site that recognizes a first epitope, wherein:

i) the first LC comprises the following domains in order from N-terminus to C-terminus: VL-CH3$_{LC}$, wherein CH3$_{LC}$ is a CH3 domain; and ii) the first HC comprises the following domains in order from N-terminus to C-terminus: VH-CH3$_{HC1}$-CH2-CH3$_{HC2}$, wherein CH3$_{HC1}$ and CH3$_{HC2}$ are each CH3 domains, further comprising a hinge between the CH3$_{HC1}$ and the CH2 domains, wherein CH3$_{LC}$ binds to CH3$_{HC1}$ thereby forming a first CH3 pair; and b) a second LC paired with a second HC to form the second dimer, the second dimer having a second binding site that recognizes a second epitope different from the first epitope, wherein:

iii) the second LC comprises the following domains in order from N-terminus to C-terminus: VL-CL; and iv) the second HC comprises the following domains in order from N-terminus to C-terminus: VH-CH1-CH2-CH3, further comprising a hinge between the CH1 domain and the CH2 domains, wherein the CH2 domain of the first dimer binds the CH2 domain of the second dimer, and the CH3$_{HC2}$ domain of the first dimer binds the CH3 domain of the second dimer, thereby forming a second CH3 pair and an Fc region of the antibody, wherein the CH3 domains of the first CH3 pair each comprise a mutation according to one of the following embodiments v) to ix) and the CH3 domains of the second CH3 pair each comprise a mutation according to one of the following embodiments v) to ix), the mutations of the CH3 domains of the first CH3 pair being different from the mutations of the CH3 domains of the second CH3 pair:

v) one CH3 domain of the CH3 pair and the other CH3 domain of the same CH3 pair respectively comprise a complementary knob and hole mutation;

vi) a cysteine residue of one CH3 domain of the CH3 pair is covalently linked to a cysteine residue of the other CH3 domain of the same CH3 pair, thereby introducing an interdomain disulfide bridge;

vii) one CH3 domain of the CH3 pair and the other CH3 domain of the same CH3 pair each comprises alternating segments of human IgA and IgG CH3 sequences;

viii) one CH3 domain of the CH3 pair and the other CH3 domain of the same CH3 pair each comprises one or more mutations where a repulsive charge suppresses heterodimer formation; or ix) one CH3 domain of the CH3 pair and the other CH3 domain of the same CH3 pair respectively each comprise mutations from the group consisting of:

T350V:L351Y:F405A:Y407V/T350V:T366L:K392L:T394W,

T350V:L351Y:F405A:Y407V/T350V:T366L:K392M:T394W,

L351Y:F405A:Y407V/T366L:K392M:T394W,

F405A:Y407V/T366L:K392M:T394W, and

F405A:Y407V/T366L:T394W, wherein numbering is according to the EU index of Kabat.

2. The antibody of claim 1, wherein the antibody further comprises an additional CH3 domain on the C-terminus of the CH3$_{HC2}$ domain of the first dimer and an additional CH3 domain on the C-terminus of the CH3 domain of the second dimer.

3. The antibody of claim 1, wherein the knob Of and hole mutation is selected from the group consisting of T366Y/Y407'T, F405A/T394'W, T366Y:F405A/T394'W:Y407'T, T366W/Y407'A, and S354C:T366W/Y349'C:T366'S:L368'A:Y407'V, wherein numbering is according to the EU index of Kabat.

4. The antibody of claim 1, wherein the interdomain disulfide bridge links the C-terminus of the CH3 domain of the second dimer and the CH3$_{HC2}$ domain of the first dimer.

5. The antibody of claim 1, wherein the one or more mutations comprising a repulsive charge that suppresses heterodimer formation are selected from the group consisting of K409D/D399'K, K409D/D399'R, K409E/D399'K, K409E/D399'R, K409D:K392D/D399'K:E356'K and K409D:K392D:K370D/D399'K:E356'K:E357'K, wherein numbering is according to the EU index of Kabat.

6. The antibody of claim 1, wherein the antibody is an effector-function competent antibody comprising a Fc gamma receptor binding site and/or a C1q binding site located in any of the CH2 and/or CH3 domains.

7. The antibody of claim 1, wherein the antibody is an effector-negative antibody comprising a Fc region deficient in binding to an Fc gamma receptor and/or C1q.

8. The antibody of claim 1, wherein the antibody comprises a pH-dependent FcRn binding site located in any of the CH2 and/or CH3 domains.

9. The antibody of claim 1, wherein the first binding site recognizes CD3 or CD16, and wherein the second binding site recognizes EGFR.

10. The antibody of claim 1, wherein at least one of the $CH3_{LC}$ or the $CH3_{HC1}$ domains of the first CH3 pair comprises at least one mutation at the FcRn binding site to reduce pH-dependent FcRn binding, wherein the at least one mutation is selected from the group consisting of a H433A mutation and a H435A mutation, wherein the numbering is according to the EU index of Kabat.

11. The antibody of claim 1, wherein the CH2 and/or CH3 domains of the antibody are of human origin, are humanized, or are functionally active variants thereof with at least 60% sequence identity to the respective human IgG1 antibody domains.

12. The antibody of claim 1, wherein the interdomain disulfide bridge links the C-terminus of $CH3_L$c domain and the $CH3_H$ci domain of the first CH3 pair.

* * * * *

SEQUENCE LISTING

<160> NUMBER OF SEQ ID NOS: 53

<210> SEQ ID NO 1
<211> LENGTH: 213
<212> TYPE: PRT
<213> ORGANISM: Artificial Sequence
<220> FEATURE:
<223> OTHER INFORMATION: VL(1)-CH3_HOLE (Y407T)

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Thr Tyr Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser His Ile Phe Thr
                85                  90                  95

Phe Gly Gln Gly Thr Lys Val Glu Ile Lys Arg Thr Val Ala Glu Pro
            100                 105                 110

Gln Val Tyr Thr Leu Pro Pro Ser Arg Asp Glu Leu Thr Lys Asn Gln
        115                 120                 125

Val Ser Leu Thr Cys Leu Val Lys Gly Phe Tyr Pro Ser Asp Ile Ala
    130                 135                 140

Val Glu Trp Glu Ser Asn Gly Gln Pro Glu Asn Asn Tyr Lys Thr Thr
145                 150                 155                 160

Pro Pro Val Leu Asp Ser Asp Gly Ser Phe Phe Leu Thr Ser Lys Leu
                165                 170                 175

Thr Val Asp Lys Ser Arg Trp Gln Gln Gly Asn Val Phe Ser Cys Ser
            180                 185                 190

Val Met His Glu Ala Leu His Asn His Tyr Thr Gln Lys Ser Leu Ser
        195                 200                 205

Leu Ser Gly Glu Cys
    210

<210> SEQ ID NO 2
<211> LENGTH: 459
<212> TYPE: PRT
<213> ORGANISM: Artificial Sequence
<220> FEATURE:
<223> OTHER INFORMATION: VH(1)-CH3_KNOB (T366Y)-CH2-CH3AG

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Gln Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Lys Ala Thr Met Thr Val Asp Thr Ser Thr Asn Thr Ala Tyr
65                  70                  75                  80

```
Met Glu Leu Ser Ser Leu Arg Ser Glu Asp Thr Ala Val Tyr Tyr Cys
                 85                  90                  95

Ala Ser Arg Asp Tyr Asp Tyr Asp Gly Arg Tyr Phe Asp Tyr Trp Gly
            100                 105                 110

Gln Gly Thr Leu Val Thr Val Ser Ser Ala Ser Thr Lys Gly Glu Pro
        115                 120                 125

Gln Val Tyr Thr Leu Pro Pro Ser Arg Asp Glu Leu Thr Lys Asn Gln
    130                 135                 140

Val Ser Leu Tyr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Phe Arg Pro Glu Val His Leu Leu Pro Pro Ser Arg Glu Glu Met Thr
        355                 360                 365

Lys Asn Gln Val Ser Leu Thr Cys Leu Ala Arg Gly Phe Tyr Pro Lys
    370                 375                 380

Asp Ile Ala Val Glu Trp Glu Ser Asn Gly Gln Pro Glu Asn Asn Tyr
385                 390                 395                 400

Lys Thr Thr Pro Ser Arg Gln Glu Pro Ser Gln Gly Thr Thr Thr Phe
                405                 410                 415

Ala Val Thr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Thr Ile Ser Leu Ser Pro Gly Lys
    450                 455

<210> SEQ ID NO 3
<211> LENGTH: 213
<212> TYPE: PRT
<213> ORGANISM: Artificial Sequence
<220> FEATURE:
<223> OTHER INFORMATION: VL(2)-CL
```

<400> SEQUENCE: 3

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Asn Trp Tyr Gln Gln Thr Pro Gly Lys Ala Pro Lys Arg Trp Ile Tyr
            35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 4
<211> LENGTH: 452
<212> TYPE: PRT
<213> ORGANISM: Artificial Sequence
<220> FEATURE:
<223> OTHER INFORMATION: VH(2)-CH1-CH2-CH3GA

<400> SEQUENCE: 4

```
Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
            35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Pro Val Thr Val Ser Ser Ala Ser Thr Lys Gly Pro Ser Val Phe
        115                 120                 125
```

```
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Pro Ser Glu Glu Leu Ala Leu Asn Glu Leu Val Thr Leu
        355                 360                 365

Thr Cys Leu Val Lys Gly Phe Tyr Pro Ser Asp Ile Ala Val Glu Trp
    370                 375                 380

Leu Gln Gly Ser Gln Glu Leu Pro Arg Glu Lys Tyr Leu Thr Trp Ala
385                 390                 395                 400

Pro Val Leu Asp Ser Asp Gly Ser Phe Phe Leu Tyr Ser Ile Leu Arg
                405                 410                 415

Val Ala Ala Glu Asp Trp Lys Lys Gly Asp Thr Phe Ser Cys Ser Val
            420                 425                 430

Met His Glu Ala Leu His Asn His Tyr Thr Gln Lys Ser Leu Asp Arg
        435                 440                 445

Ser Pro Gly Lys
    450

<210> SEQ ID NO 5
<211> LENGTH: 452
<212> TYPE: PRT
<213> ORGANISM: Artificial Sequence
<220> FEATURE:
<223> OTHER INFORMATION: VH(2)-CH1-CH2-CH3AG

<400> SEQUENCE: 5

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30
```

```
Thr Met His Trp Val Arg Gln Ala Pro Gly Lys Gly Leu Glu Trp Ile
        35                  40                  45
Gly Tyr Ile Asn Pro Ser Arg Gly Tyr Thr Asn Tyr Asn Gln Lys Val
 50                  55                  60
Lys Asp Arg Phe Thr Ile Ser Arg Asp Asn Ser Lys Asn Thr Ala Phe
 65                  70                  75                  80
Leu Gln Met Asp Ser Leu Arg Pro Glu Asp Thr Gly Val Tyr Phe Cys
                 85                  90                  95
Ala Arg Tyr Tyr Asp Asp His Tyr Cys Leu Asp Tyr Trp Gly Gln Gly
            100                 105                 110
Thr Pro Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Phe Arg Pro Glu Val His Leu
            340                 345                 350
Leu Pro Pro Ser Arg Glu Glu Met Thr Lys Asn Gln Val Ser Leu Thr
        355                 360                 365
Cys Leu Ala Arg Gly Phe Tyr Pro Lys Asp Ile Ala Val Glu Trp Glu
370                 375                 380
Ser Asn Gly Gln Pro Glu Asn Asn Tyr Lys Thr Thr Pro Ser Arg Gln
385                 390                 395                 400
Glu Pro Ser Gln Gly Thr Thr Thr Phe Ala Val Thr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Thr Ile Ser Leu
        435                 440                 445
Ser Pro Gly Lys
```

<210> SEQ ID NO 6
<211> LENGTH: 459
<212> TYPE: PRT
<213> ORGANISM: Artificial Sequence
<220> FEATURE:
<223> OTHER INFORMATION: VH(1)-CH3_KNOB (T366Y)-CH2-CH3GA

<400> SEQUENCE: 6

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Gln Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Gln Gly Thr Leu Val Thr Val Ser Ala Ser Thr Lys Gly Glu Pro
        115                 120                 125

Gln Val Tyr Thr Leu Pro Pro Ser Arg Asp Glu Leu Thr Lys Asn Gln
    130                 135                 140

Val Ser Leu Tyr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Glu Glu Leu Ala
```

```
                355                 360                 365
Leu Asn Glu Leu Val Thr Leu Thr Cys Leu Val Lys Gly Phe Tyr Pro
    370                 375                 380

Ser Asp Ile Ala Val Glu Trp Leu Gln Gly Ser Gln Glu Leu Pro Arg
385                 390                 395                 400

Glu Lys Tyr Leu Thr Trp Ala Pro Val Leu Asp Ser Asp Gly Ser Phe
                405                 410                 415

Phe Leu Tyr Ser Ile Leu Arg Val Ala Ala Glu Asp Trp Lys Lys Gly
            420                 425                 430

Asp Thr Phe Ser Cys Ser Val Met His Glu Ala Leu His Asn His Tyr
        435                 440                 445

Thr Gln Lys Ser Leu Asp Arg Ser Pro Gly Lys
    450                 455

<210> SEQ ID NO 7
<211> LENGTH: 213
<212> TYPE: PRT
<213> ORGANISM: Artificial Sequence
<220> FEATURE:
<223> OTHER INFORMATION: VL(1)-CH3wt

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Thr Tyr Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser His Ile Phe Thr
                85                  90                  95

Phe Gly Gln Gly Thr Lys Val Glu Ile Lys Arg Thr Val Ala Glu Pro
            100                 105                 110

Gln Val Tyr Thr Leu Pro Pro Ser Arg Asp Glu Leu Thr Lys Asn Gln
        115                 120                 125

Val Ser Leu Thr Cys Leu Val Lys Gly Phe Tyr Pro Ser Asp Ile Ala
    130                 135                 140

Val Glu Trp Glu Ser Asn Gly Gln Pro Glu Asn Asn Tyr Lys Thr Thr
145                 150                 155                 160

Pro Pro Val Leu Asp Ser Asp Gly Ser Phe Phe Leu Tyr Ser Lys Leu
                165                 170                 175

Thr Val Asp Lys Ser Arg Trp Gln Gln Gly Asn Val Phe Ser Cys Ser
            180                 185                 190

Val Met His Glu Ala Leu His Asn His Tyr Thr Gln Lys Ser Leu Ser
        195                 200                 205

Leu Ser Gly Glu Cys
    210

<210> SEQ ID NO 8
<211> LENGTH: 459
<212> TYPE: PRT
<213> ORGANISM: Artificial Sequence
<220> FEATURE:
<223> OTHER INFORMATION: VH(1)-CH3wt-CH2-CH3GA
```

<400> SEQUENCE: 8

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Gln Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Gln Gly Thr Leu Val Thr Val Ser Ser Ala Ser Thr Lys Gly Glu Pro
        115                 120                 125

Gln Val Tyr Thr Leu Pro Pro Ser Arg Asp Glu Leu Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Glu Glu Leu Ala
        355                 360                 365

Leu Asn Glu Leu Val Thr Thr Cys Leu Val Lys Gly Phe Tyr Pro
    370                 375                 380

Ser Asp Ile Ala Val Glu Trp Leu Gln Gly Ser Gln Glu Leu Pro Arg
385                 390                 395                 400

Glu Lys Tyr Leu Thr Trp Ala Pro Val Leu Asp Ser Asp Gly Ser Phe
```

```
                       405                 410                 415
Phe Leu Tyr Ser Ile Leu Arg Val Ala Ala Glu Asp Trp Lys Lys Gly
            420                 425                 430

Asp Thr Phe Ser Cys Ser Val Met His Glu Ala Leu His Asn His Tyr
            435                 440                 445

Thr Gln Lys Ser Leu Asp Arg Ser Pro Gly Lys
            450                 455

<210> SEQ ID NO 9
<211> LENGTH: 235
<212> TYPE: PRT
<213> ORGANISM: Artificial Sequence
<220> FEATURE:
<223> OTHER INFORMATION: huFc_GA SEED

<400> SEQUENCE: 9

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Glu Glu Leu Ala
    130                 135                 140

Leu Asn Glu Leu Val Thr Leu Thr Cys Leu Val Lys Gly Phe Tyr Pro
145                 150                 155                 160

Ser Asp Ile Ala Val Glu Trp Leu Gln Gly Ser Gln Glu Leu Pro Arg
                165                 170                 175

Glu Lys Tyr Leu Thr Trp Ala Pro Val Leu Asp Ser Asp Gly Ser Phe
            180                 185                 190

Phe Leu Tyr Ser Ile Leu Arg Val Ala Ala Glu Asp Trp Lys Lys Gly
        195                 200                 205

Asp Thr Phe Ser Cys Ser Val Met His Glu Ala Leu His Asn His Tyr
    210                 215                 220

Thr Gln Lys Ser Leu Asp Arg Ser Pro Gly Lys
225                 230                 235

<210> SEQ ID NO 10
<211> LENGTH: 213
<212> TYPE: PRT
<213> ORGANISM: Artificial Sequence
<220> FEATURE:
<223> OTHER INFORMATION: VL(1)-CL

<400> SEQUENCE: 10

Asp Ile Gln Met Thr Gln Ser Pro Ser Ser Leu Ser Ala Ser Val Gly
1               5                   10                  15
```

Asp Arg Val Thr Ile Thr Cys Ser Ala Ser Ser Ser Val Thr Tyr Met
            20                  25                  30

Tyr Trp Tyr Gln Gln Lys Pro Gly Lys Ala Pro Lys Leu Leu Ile Tyr
            35                  40                  45

Asp Thr Ser Asn Leu Ala Ser Gly Val Pro Ser Arg Phe Ser Gly Ser
        50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser His Ile Phe Thr
                85                  90                  95

Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 11
<211> LENGTH: 454
<212> TYPE: PRT
<213> ORGANISM: Artificial Sequence
<220> FEATURE:
<223> OTHER INFORMATION: VH(1)-CH1-CH2-CH3AG

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Gln Ala Pro Gly Gln Gly Leu Glu Trp Ile
            35                  40                  45

Gly Glu Phe Asn Pro Ser Asn Gly Arg Thr Asn Tyr Asn Glu Lys Phe
        50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Phe Arg Pro Glu Val
                340                 345                 350

His Leu Leu Pro Pro Ser Arg Glu Glu Met Thr Lys Asn Gln Val Ser
            355                 360                 365

Leu Thr Cys Leu Ala Arg Gly Phe Tyr Pro Lys Asp Ile Ala Val Glu
        370                 375                 380

Trp Glu Ser Asn Gly Gln Pro Glu Asn Asn Tyr Lys Thr Thr Pro Ser
385                 390                 395                 400

Arg Gln Glu Pro Ser Gln Gly Thr Thr Thr Phe Ala Val Thr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Thr Ile
            435                 440                 445

Ser Leu Ser Pro Gly Lys
        450

<210> SEQ ID NO 12
<211> LENGTH: 217
<212> TYPE: PRT
<213> ORGANISM: Artificial Sequence
<220> FEATURE:
<223> OTHER INFORMATION: VL(3)-CL

<400> SEQUENCE: 12

Ile Val Leu Thr Gln Ser Pro Ala Ser Leu Ala Val Ser Leu Gly Gln
1               5                   10                  15

Arg Ala Thr Ile Ser Cys Lys Ala Ser Gln Ser Val Asp Phe Asp Gly
            20                  25                  30

Asp Ser Phe Met Asn Trp Tyr Gln Gln Lys Pro Gly Gln Pro Pro Lys
        35                  40                  45

Leu Leu Ile Tyr Thr Thr Ser Asn Leu Glu Ser Gly Ile Pro Ala Arg
    50                  55                  60

```
Phe Ser Ala Ser Gly Ser Gly Thr Asp Phe Thr Leu Asn Ile His Pro
 65                  70                  75                  80

Val Glu Glu Asp Thr Ala Thr Tyr Tyr Cys Gln Gln Ser Asn Glu
                 85                  90                  95

Asp Pro Tyr Thr Phe Gly Gly Gly Thr Lys Leu Glu Leu Lys Arg Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
                180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
        210                 215

<210> SEQ ID NO 13
<211> LENGTH: 451
<212> TYPE: PRT
<213> ORGANISM: Artificial Sequence
<220> FEATURE:
<223> OTHER INFORMATION: VH(3)-CH1-CH2-CH3GA

<400> SEQUENCE: 13

Gln Val Thr Leu Lys Glu Ser Gly Pro Gly Ile Leu Gln Pro Ser Gln
 1               5                  10                  15

Thr Leu Ser Leu Thr Cys Ser Phe Ser Gly Phe Ser Leu Arg Thr Ser
                20                  25                  30

Gly Met Gly Val Gly Trp Ile Arg Gln Pro Ser Gly Lys Gly Leu Glu
            35                  40                  45

Trp Leu Ala His Ile Trp Trp Asp Asp Lys Arg Tyr Asn Pro Ala
 50                  55                  60

Leu Lys Ser Arg Leu Thr Ile Ser Lys Asp Thr Ser Ser Asn Gln Val
 65                  70                  75                  80

Phe Leu Lys Ile Ala Ser Val Asp Thr Ala Asp Thr Ala Thr Tyr Tyr
                85                  90                  95

Cys Ala Gln Ile Asn Pro Ala Trp Phe Ala Tyr Trp Gly Gln Gly Thr
                100                 105                 110

Leu Val Thr Val Ser Ala Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Pro Ser Glu Glu Leu Ala Leu Asn Glu Leu Val Thr Leu Thr
            355                 360                 365

Cys Leu Val Lys Gly Phe Tyr Pro Ser Asp Ile Ala Val Glu Trp Leu
370                 375                 380

Gln Gly Ser Gln Glu Leu Pro Arg Glu Lys Tyr Leu Thr Trp Ala Pro
385                 390                 395                 400

Val Leu Asp Ser Asp Gly Ser Phe Phe Leu Tyr Ser Ile Leu Arg Val
                405                 410                 415

Ala Ala Glu Asp Trp Lys Lys Gly Asp Thr Phe Ser Cys Ser Val Met
            420                 425                 430

His Glu Ala Leu His Asn His Tyr Thr Gln Lys Ser Leu Asp Arg Ser
            435                 440                 445

Pro Gly Lys
    450

<210> SEQ ID NO 14
<211> LENGTH: 451
<212> TYPE: PRT
<213> ORGANISM: Artificial Sequence
<220> FEATURE:
<223> OTHER INFORMATION: VH(3)-CH1-CH2-CH3AG

<400> SEQUENCE: 14

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Arg Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Lys Arg Tyr Asn Pro Ala
    50                  55                  60

Leu Lys Ser Arg Leu Thr Ile Ser Lys Asp Thr Ser Ser Asn Gln Val
65                  70                  75                  80

Phe Leu Lys Ile Ala Ser Val Asp Thr Ala Asp Thr Ala Thr Tyr Tyr
                85                  90                  95

Cys Ala Gln Ile Asn Pro Ala Trp Phe Ala Tyr Trp Gly Gln Gly Thr
            100                 105                 110

```
Leu Val Thr Val Ser Ala Ala Ser Thr Lys Gly Pro Ser Val Phe Pro
            115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
    210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Phe Arg Pro Glu Val His Leu Leu
            340                 345                 350
Pro Pro Ser Arg Glu Glu Met Thr Lys Asn Gln Val Ser Leu Thr Cys
        355                 360                 365
Leu Ala Arg Gly Phe Tyr Pro Lys Asp Ile Ala Val Glu Trp Glu Ser
    370                 375                 380
Asn Gly Gln Pro Glu Asn Asn Tyr Lys Thr Thr Pro Ser Arg Gln Glu
385                 390                 395                 400
Pro Ser Gln Gly Thr Thr Thr Phe Ala Val Thr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Thr Ile Ser Leu Ser
        435                 440                 445
Pro Gly Lys
    450

<210> SEQ ID NO 15
<211> LENGTH: 458
<212> TYPE: PRT
<213> ORGANISM: Artificial Sequence
<220> FEATURE:
<223> OTHER INFORMATION: VH(1)-CH3_KNOB (T366Y)-CH2EN-CH3AG

<400> SEQUENCE: 15

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser His
             20                  25                  30

Trp Met His Trp Val Arg Gln Ala Pro Gly Gln Gly Leu Glu Trp Ile
         35                  40                  45

Gly Glu Phe Asn Pro Ser Asn Gly Arg Thr Asn Tyr Asn Glu Lys Phe
     50                  55                  60

Lys Ser Lys Ala Thr Met Thr Val Asp Thr Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Ala Ser Arg Asp Tyr Asp Tyr Asp Gly Arg Tyr Phe Asp Tyr Trp Gly
            100                 105                 110

Gln Gly Thr Leu Val Thr Val Ser Ser Ala Ser Thr Lys Gly Glu Pro
        115                 120                 125

Gln Val Tyr Thr Leu Pro Pro Ser Arg Asp Glu Leu Thr Lys Asn Gln
    130                 135                 140

Val Ser Leu Tyr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Lys Ser Cys Asp Lys Thr His Thr Cys Pro Pro Cys Pro Ala
225                 230                 235                 240

Pro Pro Val Ala Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Gln Phe Asn Trp Tyr Val Asp
        275                 280                 285

Gly Val Glu Val His Asn Ala Lys Thr Lys Pro Arg Glu Glu Gln Ala
    290                 295                 300

Gln Ser Thr Phe Arg Val Val Ser Val Leu Thr Val Val His Gln Asp
305                 310                 315                 320

Trp Leu Asn Gly Lys Glu Tyr Lys Cys Lys Val Ser Asn Lys Gly Leu
                325                 330                 335

Pro Ala Pro Ile Glu Lys Thr Ile Ser Lys Thr Lys Gly Gln Pro Phe
            340                 345                 350

Arg Pro Glu Val His Leu Leu Pro Pro Ser Arg Glu Glu Met Thr Lys
        355                 360                 365

Asn Gln Val Ser Leu Thr Cys Leu Ala Arg Gly Phe Tyr Pro Lys Asp
    370                 375                 380

Ile Ala Val Glu Trp Glu Ser Asn Gly Gln Pro Glu Asn Asn Tyr Lys
385                 390                 395                 400

Thr Thr Pro Ser Arg Gln Glu Pro Ser Gln Gly Thr Thr Thr Phe Ala
                405                 410                 415

Val Thr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
```

```
                    435                 440                 445
Gln Lys Thr Ile Ser Leu Ser Pro Gly Lys
    450                 455

<210> SEQ ID NO 16
<211> LENGTH: 234
<212> TYPE: PRT
<213> ORGANISM: Artificial Sequence
<220> FEATURE:
<223> OTHER INFORMATION: huFc_g1hingeEN-CH2EN-CH3GA

<400> SEQUENCE: 16

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Gln Phe Asn Trp Tyr Val Asp
    50                  55                  60

Gly Val Glu Val His Asn Ala Lys Thr Lys Pro Arg Glu Glu Gln Ala
65                  70                  75                  80

Gln Ser Thr Phe Arg Val Val Ser Val Leu Thr Val His Gln Asp
                85                  90                  95

Trp Leu Asn Gly Lys Glu Tyr Lys Cys Lys Val Ser Asn Lys Gly Leu
            100                 105                 110

Pro Ala Pro Ile Glu Lys Thr Ile Ser Lys Thr Lys Gly Gln Pro Arg
        115                 120                 125

Glu Pro Gln Val Tyr Thr Leu Pro Pro Ser Glu Glu Leu Ala Leu
    130                 135                 140

Asn Glu Leu Val Thr Leu Thr Cys Leu Val Lys Gly Phe Tyr Pro Ser
145                 150                 155                 160

Asp Ile Ala Val Glu Trp Leu Gln Gly Ser Gln Glu Leu Pro Arg Glu
                165                 170                 175

Lys Tyr Leu Thr Trp Ala Pro Val Leu Asp Ser Asp Gly Ser Phe Phe
            180                 185                 190

Leu Tyr Ser Ile Leu Arg Val Ala Ala Glu Asp Trp Lys Lys Gly Asp
        195                 200                 205

Thr Phe Ser Cys Ser Val Met His Glu Ala Leu His Asn His Tyr Thr
    210                 215                 220

Gln Lys Ser Leu Asp Arg Ser Pro Gly Lys
225                 230

<210> SEQ ID NO 17
<211> LENGTH: 450
<212> TYPE: PRT
<213> ORGANISM: Artificial Sequence
<220> FEATURE:
<223> OTHER INFORMATION: VH(3)-CH1-CH2EN-CH3GA

<400> SEQUENCE: 17

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Arg Thr Ser
            20                  25                  30

Gly Met Gly Val Gly Trp Ile Arg Gln Pro Ser Gly Lys Gly Leu Glu
        35                  40                  45
```

-continued

```
Trp Leu Ala His Ile Trp Trp Asp Asp Asp Lys Arg Tyr Asn Pro Ala
 50                  55                  60

Leu Lys Ser Arg Leu Thr Ile Ser Lys Asp Thr Ser Ser Asn Gln Val
 65                  70                  75                  80

Phe Leu Lys Ile Ala Ser Val Asp Thr Ala Asp Thr Ala Thr Tyr Tyr
                 85                  90                  95

Cys Ala Gln Ile Asn Pro Ala Trp Phe Ala Tyr Trp Gly Gln Gly Thr
                100                 105                 110

Leu Val Thr Val Ser Ala Ala Ser Thr Lys Gly Pro Ser Val Phe Pro
                115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
210                 215                 220

His Thr Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Ala Gln Ser Thr Phe Arg Val Val Ser
                290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
                340                 345                 350

Pro Pro Ser Glu Glu Leu Ala Leu Asn Glu Leu Val Thr Leu Thr Cys
                355                 360                 365

Leu Val Lys Gly Phe Tyr Pro Ser Asp Ile Ala Val Glu Trp Leu Gln
                370                 375                 380

Gly Ser Gln Glu Leu Pro Arg Glu Lys Tyr Leu Thr Trp Ala Pro Val
385                 390                 395                 400

Leu Asp Ser Asp Gly Ser Phe Phe Leu Tyr Ser Ile Leu Arg Val Ala
                405                 410                 415

Ala Glu Asp Trp Lys Lys Gly Asp Thr Phe Ser Cys Ser Val Met His
                420                 425                 430

Glu Ala Leu His Asn His Tyr Thr Gln Lys Ser Leu Asp Arg Ser Pro
                435                 440                 445

Gly Lys
450
```

```
<210> SEQ ID NO 18
<211> LENGTH: 459
<212> TYPE: PRT
<213> ORGANISM: Artificial Sequence
<220> FEATURE:
<223> OTHER INFORMATION: VH(1)-CH3_KNOB (T366W)-CH2-CH3AG

<400> SEQUENCE: 18

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Gln Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Gln Gly Thr Leu Val Thr Val Ser Ser Ala Ser Thr Lys Gly Glu Pro
        115                 120                 125

Gln Val Tyr Thr Leu Pro Pro Ser Arg Asp Glu Leu Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Phe Arg Pro Glu Val His Leu Leu Pro Pro Ser Arg Glu Glu Met Thr
        355                 360                 365

Lys Asn Gln Val Ser Leu Thr Cys Leu Ala Arg Gly Phe Tyr Pro Lys
```

```
                  370             375             380
Asp Ile Ala Val Glu Trp Glu Ser Asn Gly Gln Pro Glu Asn Asn Tyr
385                 390                 395                 400

Lys Thr Thr Pro Ser Arg Gln Glu Pro Ser Gln Gly Thr Thr Thr Phe
                405                 410                 415

Ala Val Thr Ser Lys Leu Thr Val Asp Lys Ser Arg Trp Gln Gln Gly
                420                 425                 430

Asn Val Phe Ser Cys Ser Val Met His Glu Ala Leu His Asn His Tyr
                435                 440                 445

Thr Gln Lys Thr Ile Ser Leu Ser Pro Gly Lys
    450                 455

<210> SEQ ID NO 19
<211> LENGTH: 213
<212> TYPE: PRT
<213> ORGANISM: Artificial Sequence
<220> FEATURE:
<223> OTHER INFORMATION: VL(1)-CH3_HOLE (T366S, L368A, Y407V)

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Thr Tyr Met
                20                  25                  30

Tyr Trp Tyr Gln Gln Lys Pro Gly Lys Ala Pro Lys Leu Leu Ile Tyr
            35                  40                  45

Asp Thr Ser Asn Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser His Ile Phe Thr
                85                  90                  95

Phe Gly Gln Gly Thr Lys Val Glu Ile Lys Arg Thr Val Ala Glu Pro
            100                 105                 110

Gln Val Tyr Thr Leu Pro Pro Ser Arg Asp Glu Leu Thr Lys Asn Gln
        115                 120                 125

Val Ser Leu Ser Cys Ala Val Lys Gly Phe Tyr Pro Ser Asp Ile Ala
    130                 135                 140

Val Glu Trp Glu Ser Asn Gly Gln Pro Glu Asn Asn Tyr Lys Thr Thr
145                 150                 155                 160

Pro Pro Val Leu Asp Ser Asp Gly Ser Phe Phe Leu Val Ser Lys Leu
                165                 170                 175

Thr Val Asp Lys Ser Arg Trp Gln Gln Gly Asn Val Phe Ser Cys Ser
            180                 185                 190

Val Met His Glu Ala Leu His Asn His Tyr Thr Gln Lys Ser Leu Ser
        195                 200                 205

Leu Ser Gly Glu Cys
    210

<210> SEQ ID NO 20
<211> LENGTH: 459
<212> TYPE: PRT
<213> ORGANISM: Artificial Sequence
<220> FEATURE:
<223> OTHER INFORMATION: VH(1)-CH3_HOLE (T366S, L368A, Y407V)-CH2-CH3AG

<400> SEQUENCE: 20
```

-continued

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Gln Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Gln Gly Thr Leu Val Thr Val Ser Ser Ala Ser Thr Lys Gly Glu Pro
        115                 120                 125

Gln Val Tyr Thr Leu Pro Pro Ser Arg Asp Glu Leu Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Phe Arg Pro Glu Val His Leu Leu Pro Pro Ser Arg Glu Glu Met Thr
        355                 360                 365

Lys Asn Gln Val Ser Leu Thr Cys Leu Ala Arg Gly Phe Tyr Pro Lys
    370                 375                 380

Asp Ile Ala Val Glu Trp Glu Ser Asn Gly Gln Pro Glu Asn Asn Tyr
385                 390                 395                 400

Lys Thr Thr Pro Ser Arg Gln Glu Pro Ser Gln Gly Thr Thr Thr Phe
                405                 410                 415

Ala Val Thr Ser Lys Leu Thr Val Asp Lys Ser Arg Trp Gln Gln Gly
```

```
                420                 425                 430
Asn Val Phe Ser Cys Ser Val Met His Glu Ala Leu His Asn His Tyr
            435                 440                 445

Thr Gln Lys Thr Ile Ser Leu Ser Pro Gly Lys
    450                 455

<210> SEQ ID NO 21
<211> LENGTH: 213
<212> TYPE: PRT
<213> ORGANISM: Artificial Sequence
<220> FEATURE:
<223> OTHER INFORMATION: VL(1)-CH3_KNOB (T366W)

<400> SEQUENCE: 21

Asp Ile Gln Met Thr Gln Ser Pro Ser Leu Ser Ala Ser Val Gly
1               5                   10                  15

Asp Arg Val Thr Ile Thr Cys Ser Ala Ser Ser Ser Val Thr Tyr Met
                20                  25                  30

Tyr Trp Tyr Gln Gln Lys Pro Gly Lys Ala Pro Lys Leu Leu Ile Tyr
            35                  40                  45

Asp Thr Ser Asn Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser His Ile Phe Thr
                85                  90                  95

Phe Gly Gln Gly Thr Lys Val Glu Ile Lys Arg Thr Val Ala Glu Pro
            100                 105                 110

Gln Val Tyr Thr Leu Pro Pro Ser Arg Asp Glu Leu Thr Lys Asn Gln
        115                 120                 125

Val Ser Leu Trp Cys Leu Val Lys Gly Phe Tyr Pro Ser Asp Ile Ala
130                 135                 140

Val Glu Trp Glu Ser Asn Gly Gln Pro Glu Asn Asn Tyr Lys Thr Thr
145                 150                 155                 160

Pro Pro Val Leu Asp Ser Asp Gly Ser Phe Phe Leu Tyr Ser Lys Leu
                165                 170                 175

Thr Val Asp Lys Ser Arg Trp Gln Gln Gly Asn Val Phe Ser Cys Ser
            180                 185                 190

Val Met His Glu Ala Leu His Asn His Tyr Thr Gln Lys Ser Leu Ser
        195                 200                 205

Leu Ser Gly Glu Cys
    210

<210> SEQ ID NO 22
<211> LENGTH: 459
<212> TYPE: PRT
<213> ORGANISM: Artificial Sequence
<220> FEATURE:
<223> OTHER INFORMATION: VH(1)-CH3 (E356K, D399K)-CH2-CH3AG

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
                20                  25                  30

Trp Met His Trp Val Arg Gln Ala Pro Gly Gln Gly Leu Glu Trp Ile
            35                  40                  45
```

```
Gly Glu Phe Asn Pro Ser Asn Gly Arg Thr Asn Tyr Asn Glu Lys Phe
 50                  55                  60

Lys Ser Lys Ala Thr Met Thr Val Asp Thr Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Ala Ser Arg Asp Tyr Asp Tyr Asp Gly Arg Tyr Phe Asp Tyr Trp Gly
                100                 105                 110

Gln Gly Thr Leu Val Thr Val Ser Ala Ser Thr Lys Gly Glu Pro
            115                 120                 125

Gln Val Tyr Thr Leu Pro Pro Ser Arg Lys Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Lys Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
            195                 200                 205

Val Met His Glu Ala Leu His Asn His Tyr Thr Gln Lys Ser Leu Ser
210                 215                 220

Leu Ser Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
            290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Phe Arg Pro Glu Val His Leu Leu Pro Pro Ser Arg Glu Glu Met Thr
            355                 360                 365

Lys Asn Gln Val Ser Leu Thr Cys Leu Ala Arg Gly Phe Tyr Pro Lys
370                 375                 380

Asp Ile Ala Val Glu Trp Glu Ser Asn Gly Gln Pro Glu Asn Asn Tyr
385                 390                 395                 400

Lys Thr Thr Pro Ser Arg Gln Glu Pro Ser Gln Gly Thr Thr Thr Phe
                405                 410                 415

Ala Val Thr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
            435                 440                 445

Thr Gln Lys Thr Ile Ser Leu Ser Pro Gly Lys
450                 455
```

```
<210> SEQ ID NO 23
<211> LENGTH: 213
<212> TYPE: PRT
<213> ORGANISM: Artificial Sequence
<220> FEATURE:
<223> OTHER INFORMATION: VL(1)-CH3 (K392D, K409D)

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Thr Tyr Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser His Ile Phe Thr
                85                  90                  95

Phe Gly Gln Gly Thr Lys Val Glu Ile Lys Arg Thr Val Ala Glu Pro
            100                 105                 110

Gln Val Tyr Thr Leu Pro Pro Ser Arg Glu Glu Met Thr Lys Asn Gln
        115                 120                 125

Val Ser Leu Thr Cys Leu Val Lys Gly Phe Tyr Pro Ser Asp Ile Ala
    130                 135                 140

Val Glu Trp Glu Ser Asn Gly Gln Pro Glu Asn Asn Tyr Asp Thr Thr
145                 150                 155                 160

Pro Pro Val Leu Asp Ser Asp Gly Ser Phe Phe Leu Tyr Ser Asp Leu
                165                 170                 175

Thr Val Asp Lys Ser Arg Trp Gln Gln Gly Asn Val Phe Ser Cys Ser
            180                 185                 190

Val Met His Glu Ala Leu His Asn His Tyr Thr Gln Lys Ser Leu Ser
        195                 200                 205

Leu Ser Gly Glu Cys
    210

<210> SEQ ID NO 24
<211> LENGTH: 459
<212> TYPE: PRT
<213> ORGANISM: Artificial Sequence
<220> FEATURE:
<223> OTHER INFORMATION: VH(1)-CH3 (K392D, K409D)-CH2-CH3AG

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Gln Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95
```

Ala Ser Arg Asp Tyr Asp Tyr Asp Gly Arg Tyr Phe Asp Tyr Trp Gly
            100                 105                 110

Gln Gly Thr Leu Val Thr Val Ser Ser Ala Ser Thr Lys Gly Glu Pro
        115                 120                 125

Gln Val Tyr Thr Leu Pro Pro Ser Arg Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Asp Thr Thr
            165                 170                 175

Pro Pro Val Leu Asp Ser Asp Gly Ser Phe Phe Leu Tyr Ser Asp Leu
        180                 185                 190

Thr Val Asp Lys Ser Arg Trp Gln Gln Gly Asn Val Phe Ser Cys Ser
    195                 200                 205

Val Met His Glu Ala Leu His Asn His Tyr Thr Gln Lys Ser Leu Ser
210                 215                 220

Leu Ser Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
            245                 250                 255

Lys Asp Thr Leu Met Ile Ser Arg Thr Pro Glu Val Thr Cys Val Val
        260                 265                 270

Val Asp Val Ser His Glu Asp Pro Glu Val Lys Phe Asn Trp Tyr Val
    275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
            325                 330                 335

Leu Pro Ala Pro Ile Glu Lys Thr Ile Ser Lys Ala Lys Gly Gln Pro
        340                 345                 350

Phe Arg Pro Glu Val His Leu Leu Pro Pro Ser Arg Glu Glu Met Thr
    355                 360                 365

Lys Asn Gln Val Ser Leu Thr Cys Leu Ala Arg Gly Phe Tyr Pro Lys
370                 375                 380

Asp Ile Ala Val Glu Trp Glu Ser Asn Gly Gln Pro Glu Asn Asn Tyr
385                 390                 395                 400

Lys Thr Thr Pro Ser Arg Gln Glu Pro Ser Gln Gly Thr Thr Thr Phe
            405                 410                 415

Ala Val Thr Ser Lys Leu Thr Val Asp Lys Ser Arg Trp Gln Gln Gly
        420                 425                 430

Asn Val Phe Ser Cys Ser Val Met His Glu Ala Leu His Asn His Tyr
    435                 440                 445

Thr Gln Lys Thr Ile Ser Leu Ser Pro Gly Lys
        450                 455

<210> SEQ ID NO 25
<211> LENGTH: 213
<212> TYPE: PRT
<213> ORGANISM: Artificial Sequence
<220> FEATURE:
<223> OTHER INFORMATION: VL(1)-CH3 (E356K, D399K)

<400> SEQUENCE: 25

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Thr Tyr Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser His Ile Phe Thr
            85                  90                  95

Phe Gly Gln Gly Thr Lys Val Glu Ile Lys Arg Thr Val Ala Glu Pro
        100                 105                 110

Gln Val Tyr Thr Leu Pro Pro Ser Arg Lys Glu Met Thr Lys Asn Gln
        115                 120                 125

Val Ser Leu Thr Cys Leu Val Lys Gly Phe Tyr Pro Ser Asp Ile Ala
        130                 135                 140

Val Glu Trp Glu Ser Asn Gly Gln Pro Glu Asn Asn Tyr Lys Thr Thr
145                 150                 155                 160

Pro Pro Val Leu Lys Ser Asp Gly Ser Phe Phe Leu Tyr Ser Lys Leu
            165                 170                 175

Thr Val Asp Lys Ser Arg Trp Gln Gln Gly Asn Val Phe Ser Cys Ser
            180                 185                 190

Val Met His Glu Ala Leu His Asn His Tyr Thr Gln Lys Ser Leu Ser
        195                 200                 205

Leu Ser Gly Glu Cys
        210

<210> SEQ ID NO 26
<211> LENGTH: 459
<212> TYPE: PRT
<213> ORGANISM: Artificial Sequence
<220> FEATURE:
<223> OTHER INFORMATION: VH(1)-CH3 (T350V, L351Y, F405A, Y407V)-CH2-
      CH3AG

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Gln Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
            85                  90                  95

Ala Ser Arg Asp Tyr Asp Tyr Asp Gly Arg Tyr Phe Asp Tyr Trp Gly
        100                 105                 110

Gln Gly Thr Leu Val Thr Val Ser Ser Ala Ser Thr Lys Gly Glu Pro
        115                 120                 125

Gln Val Tyr Val Tyr Pro Pro Ser Arg Glu Glu Met Thr Lys Asn Gln
        130                 135                 140
```

```
Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Ala Leu Val Ser Lys Leu
            180                 185                 190

Thr Val Asp Lys Ser Arg Trp Gln Gln Gly Asn Val Phe Ser Cys Ser
            195                 200                 205

Val Met His Glu Ala Leu His Asn His Tyr Thr Gln Lys Ser Leu Ser
210                 215                 220

Leu Ser Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Phe Arg Pro Glu Val His Leu Leu Pro Pro Ser Arg Glu Glu Met Thr
            355                 360                 365

Lys Asn Gln Val Ser Leu Thr Cys Leu Ala Arg Gly Phe Tyr Pro Lys
370                 375                 380

Asp Ile Ala Val Glu Trp Glu Ser Asn Gly Gln Pro Glu Asn Asn Tyr
385                 390                 395                 400

Lys Thr Thr Pro Ser Arg Gln Glu Pro Ser Gln Gly Thr Thr Thr Phe
            405                 410                 415

Ala Val Thr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
            435                 440                 445

Thr Gln Lys Thr Ile Ser Leu Ser Pro Gly Lys
            450                 455

<210> SEQ ID NO 27
<211> LENGTH: 213
<212> TYPE: PRT
<213> ORGANISM: Artificial Sequence
<220> FEATURE:
<223> OTHER INFORMATION: VL(1)-CH3 (T350V, T366L, K392L, T394W)

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Thr Tyr Met
            20                  25                  30

Tyr Trp Tyr Gln Gln Lys Pro Gly Lys Ala Pro Lys Leu Leu Ile Tyr
        35                  40                  45
```

```
Asp Thr Ser Asn Leu Ala Ser Gly Val Pro Ser Arg Phe Ser Gly Ser
         50                  55                  60

Gly Ser Gly Thr Asp Tyr Thr Phe Thr Ile Ser Ser Leu Gln Pro Glu
 65                  70                  75                  80

Asp Ile Ala Thr Tyr Tyr Cys Gln Gln Trp Ser Ser His Ile Phe Thr
                 85                  90                  95

Phe Gly Gln Gly Thr Lys Val Glu Ile Lys Arg Thr Val Ala Glu Pro
            100                 105                 110

Gln Val Tyr Val Leu Pro Pro Ser Arg Glu Glu Met Thr Lys Asn Gln
        115                 120                 125

Val Ser Leu Leu Cys Leu Val Lys Gly Phe Tyr Pro Ser Asp Ile Ala
130                 135                 140

Val Glu Trp Glu Ser Asn Gly Gln Pro Glu Asn Asn Tyr Leu Thr Trp
145                 150                 155                 160

Pro Pro Val Leu Asp Ser Asp Gly Ser Phe Phe Leu Tyr Ser Lys Leu
                165                 170                 175

Thr Val Asp Lys Ser Arg Trp Gln Gln Gly Asn Val Phe Ser Cys Ser
            180                 185                 190

Val Met His Glu Ala Leu His Asn His Tyr Thr Gln Lys Ser Leu Ser
        195                 200                 205

Leu Ser Gly Glu Cys
    210

<210> SEQ ID NO 28
<211> LENGTH: 459
<212> TYPE: PRT
<213> ORGANISM: Artificial Sequence
<220> FEATURE:
<223> OTHER INFORMATION: VH(1)-CH3 (T350V, T366L, K392L, T394W)-CH2-
      CH3AG

<400> SEQUENCE: 28

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser His
             20                  25                  30

Trp Met His Trp Val Arg Gln Ala Pro Gly Gln Gly Leu Glu Trp Ile
         35                  40                  45

Gly Glu Phe Asn Pro Ser Asn Gly Arg Thr Asn Tyr Asn Glu Lys Phe
     50                  55                  60

Lys Ser Lys Ala Thr Met Thr Val Asp Thr Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Ala Ser Arg Asp Tyr Asp Tyr Asp Gly Arg Tyr Phe Asp Tyr Trp Gly
            100                 105                 110

Gln Gly Thr Leu Val Thr Val Ser Ala Ser Thr Lys Gly Glu Pro
        115                 120                 125

Gln Val Tyr Val Leu Pro Pro Ser Arg Glu Glu Met Thr Lys Asn Gln
        130                 135                 140

Val Ser Leu Leu Cys Leu Val Lys Gly Phe Tyr Pro Ser Asp Ile Ala
145                 150                 155                 160

Val Glu Trp Glu Ser Asn Gly Gln Pro Glu Asn Asn Tyr Leu Thr Trp
                165                 170                 175

Pro Pro Val Leu Asp Ser Asp Gly Ser Phe Phe Leu Tyr Ser Lys Leu
```

```
                180             185             190
Thr Val Asp Lys Ser Arg Trp Gln Gln Gly Asn Val Phe Ser Cys Ser
            195                 200                 205

Val Met His Glu Ala Leu His Asn His Tyr Thr Gln Lys Ser Leu Ser
        210                 215                 220

Leu Ser Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Phe Arg Pro Glu Val His Leu Leu Pro Pro Ser Arg Glu Glu Met Thr
        355                 360                 365

Lys Asn Gln Val Ser Leu Thr Cys Leu Ala Arg Gly Phe Tyr Pro Lys
    370                 375                 380

Asp Ile Ala Val Glu Trp Glu Ser Asn Gly Gln Pro Glu Asn Asn Tyr
385                 390                 395                 400

Lys Thr Thr Pro Ser Arg Gln Glu Pro Ser Gln Gly Thr Thr Thr Phe
                405                 410                 415

Ala Val Thr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Thr Ile Ser Leu Ser Pro Gly Lys
    450                 455

<210> SEQ ID NO 29
<211> LENGTH: 213
<212> TYPE: PRT
<213> ORGANISM: Artificial Sequence
<220> FEATURE:
<223> OTHER INFORMATION: VL(1)-CH3 (T350V, L351Y, F405A, Y407V)

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Thr Tyr Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser His Ile Phe Thr
```

```
            85                  90                  95
Phe Gly Gln Gly Thr Lys Val Glu Ile Lys Arg Thr Val Ala Glu Pro
            100                 105                 110

Gln Val Tyr Val Tyr Pro Pro Ser Arg Glu Glu Met Thr Lys Asn Gln
            115                 120                 125

Val Ser Leu Thr Cys Leu Val Lys Gly Phe Tyr Pro Ser Asp Ile Ala
            130                 135                 140

Val Glu Trp Glu Ser Asn Gly Gln Pro Glu Asn Asn Tyr Lys Thr Thr
145                 150                 155                 160

Pro Pro Val Leu Asp Ser Asp Gly Ser Phe Ala Leu Val Ser Lys Leu
            165                 170                 175

Thr Val Asp Lys Ser Arg Trp Gln Gln Gly Asn Val Phe Ser Cys Ser
            180                 185                 190

Val Met His Glu Ala Leu His Asn His Tyr Thr Gln Lys Ser Leu Ser
            195                 200                 205

Leu Ser Gly Glu Cys
            210

<210> SEQ ID NO 30
<211> LENGTH: 461
<212> TYPE: PRT
<213> ORGANISM: Artificial Sequence
<220> FEATURE:
<223> OTHER INFORMATION: VH(1)-CH3_SEED (AG)-CH2-CH3AG

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Gln Ala Pro Gly Gln Gly Leu Glu Trp Ile
            35                  40                  45

Gly Glu Phe Asn Pro Ser Asn Gly Arg Thr Asn Tyr Asn Glu Lys Phe
            50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
            85                  90                  95

Ala Ser Arg Asp Tyr Asp Tyr Asp Gly Arg Tyr Phe Asp Tyr Trp Gly
            100                 105                 110

Gln Gly Thr Leu Val Thr Val Ser Ser Ala Ser Thr Lys Gly Pro Glu
            115                 120                 125

Val His Leu Leu Pro Pro Ser Arg Glu Glu Met Thr Lys Asn Gln Val
            130                 135                 140

Ser Leu Thr Cys Leu Ala Arg Gly Phe Tyr Pro Lys Asp Ile Ala Val
145                 150                 155                 160

Glu Trp Glu Ser Asn Gly Gln Pro Glu Asn Asn Tyr Lys Thr Thr Pro
            165                 170                 175

Ser Arg Gln Glu Pro Ser Gln Gly Thr Thr Thr Phe Ala Val Thr Ser
            180                 185                 190

Lys Leu Thr Val Asp Lys Ser Arg Trp Gln Gln Gly Asn Val Phe Ser
            195                 200                 205

Cys Ser Val Met His Glu Ala Leu His Asn His Tyr Thr Gln Lys Thr
            210                 215                 220

Ile Ser Leu Ser Lys Ser Cys Asp Lys Thr His Thr Cys Pro Pro Cys
```

```
                225                 230                 235                 240
        Pro Ala Pro Glu Leu Leu Gly Gly Pro Ser Val Phe Leu Phe Pro Pro
                        245                 250                 255

Lys Pro Lys Asp Thr Leu Met Ile Ser Arg Thr Pro Glu Val Thr Cys
                        260                 265                 270

Val Val Val Asp Val Ser His Glu Asp Pro Glu Val Lys Phe Asn Trp
                        275                 280                 285

Tyr Val Asp Gly Val Glu Val His Asn Ala Lys Thr Lys Pro Arg Glu
                        290                 295                 300

Glu Gln Tyr Asn Ser Thr Tyr Arg Val Val Ser Val Leu Thr Val Leu
        305                 310                 315                 320

His Gln Asp Trp Leu Asn Gly Lys Glu Tyr Lys Cys Lys Val Ser Asn
                        325                 330                 335

Lys Ala Leu Pro Ala Pro Ile Glu Lys Thr Ile Ser Lys Ala Lys Gly
                        340                 345                 350

Gln Pro Phe Arg Pro Glu Val His Leu Leu Pro Pro Ser Arg Glu Glu
                        355                 360                 365

Met Thr Lys Asn Gln Val Ser Leu Thr Cys Leu Ala Arg Gly Phe Tyr
                        370                 375                 380

Pro Lys Asp Ile Ala Val Glu Trp Glu Ser Asn Gly Gln Pro Glu Asn
        385                 390                 395                 400

Asn Tyr Lys Thr Thr Pro Ser Arg Gln Glu Pro Ser Gln Gly Thr Thr
                        405                 410                 415

Thr Phe Ala Val Thr Ser Lys Leu Thr Val Asp Lys Ser Arg Trp Gln
                        420                 425                 430

Gln Gly Asn Val Phe Ser Cys Ser Val Met His Glu Ala Leu His Asn
                        435                 440                 445

His Tyr Thr Gln Lys Thr Ile Ser Leu Ser Pro Gly Lys
                        450                 455                 460

<210> SEQ ID NO 31
<211> LENGTH: 216
<212> TYPE: PRT
<213> ORGANISM: Artificial Sequence
<220> FEATURE:
<223> OTHER INFORMATION: VL(1)-CH3_SEED (GA)

<400> SEQUENCE: 31

Asp Ile Gln Met Thr Gln Ser Pro Ser Ser Leu Ser Ala Ser Val Gly
        1               5                   10                  15

Asp Arg Val Thr Ile Thr Cys Ser Ala Ser Ser Ser Val Thr Tyr Met
                        20                  25                  30

Tyr Trp Tyr Gln Gln Lys Pro Gly Lys Ala Pro Lys Leu Leu Ile Tyr
                        35                  40                  45

Asp Thr Ser Asn Leu Ala Ser Gly Val Pro Ser Arg Phe Ser Gly Ser
                        50                  55                  60

Gly Ser Gly Thr Asp Tyr Thr Phe Thr Ile Ser Ser Leu Gln Pro Glu
        65                  70                  75                  80

Asp Ile Ala Thr Tyr Tyr Cys Gln Gln Trp Ser Ser His Ile Phe Thr
                        85                  90                  95

Phe Gly Gln Gly Thr Lys Val Glu Ile Lys Arg Thr Val Ala Glu Pro
                        100                 105                 110

Gln Val Tyr Thr Leu Pro Pro Ser Glu Glu Leu Ala Leu Asn Glu
                        115                 120                 125

Leu Val Thr Leu Thr Cys Leu Val Lys Gly Phe Tyr Pro Ser Asp Ile
```

```
                130               135               140
Ala Val Glu Trp Leu Gln Gly Ser Gln Glu Leu Pro Arg Glu Lys Tyr
145                 150                 155                 160

Leu Thr Trp Ala Pro Val Leu Asp Ser Asp Gly Ser Phe Phe Leu Tyr
                165                 170                 175

Ser Ile Leu Arg Val Ala Ala Glu Asp Trp Lys Lys Gly Asp Thr Phe
                180                 185                 190

Ser Cys Ser Val Met His Glu Ala Leu His Asn His Tyr Thr Gln Lys
                195                 200                 205

Ser Leu Asp Arg Ser Gly Glu Cys
            210                 215

<210> SEQ ID NO 32
<211> LENGTH: 462
<212> TYPE: PRT
<213> ORGANISM: Artificial Sequence
<220> FEATURE:
<223> OTHER INFORMATION: VH(1)-CH3_SEED (GA)-CH2-CH3AG

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
                20                  25                  30

Trp Met His Trp Val Arg Gln Ala Pro Gly Gln Gly Leu Glu Trp Ile
            35                  40                  45

Gly Glu Phe Asn Pro Ser Asn Gly Arg Thr Asn Tyr Asn Glu Lys Phe
        50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Gln Gly Thr Leu Val Thr Val Ser Ser Ala Ser Thr Lys Gly Glu Pro
        115                 120                 125

Gln Val Tyr Thr Leu Pro Pro Ser Glu Glu Leu Ala Leu Asn Glu
    130                 135                 140

Leu Val Thr Leu Thr Cys Leu Val Lys Gly Phe Tyr Pro Ser Asp Ile
145                 150                 155                 160

Ala Val Glu Trp Leu Gln Gly Ser Gln Glu Leu Pro Arg Glu Lys Tyr
                165                 170                 175

Leu Thr Trp Ala Pro Val Leu Asp Ser Asp Gly Ser Phe Phe Leu Tyr
            180                 185                 190

Ser Ile Leu Arg Val Ala Ala Glu Asp Trp Lys Lys Gly Asp Thr Phe
        195                 200                 205

Ser Cys Ser Val Met His Glu Ala Leu His Asn His Tyr Thr Gln Lys
    210                 215                 220

Ser Leu Asp Arg Ser Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
```

```
                    275                 280                 285
Trp Tyr Val Asp Gly Val Glu Val His Asn Ala Lys Thr Lys Pro Arg
    290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Phe Arg Pro Glu Val His Leu Leu Pro Pro Ser Arg Glu
        355                 360                 365

Glu Met Thr Lys Asn Gln Val Ser Leu Thr Cys Leu Ala Arg Gly Phe
    370                 375                 380

Tyr Pro Lys Asp Ile Ala Val Glu Trp Glu Ser Asn Gly Gln Pro Glu
385                 390                 395                 400

Asn Asn Tyr Lys Thr Thr Pro Ser Arg Gln Glu Pro Ser Gln Gly Thr
                405                 410                 415

Thr Thr Phe Ala Val Thr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Thr Ile Ser Leu Ser Pro Gly Lys
    450                 455                 460

<210> SEQ ID NO 33
<211> LENGTH: 215
<212> TYPE: PRT
<213> ORGANISM: Artificial Sequence
<220> FEATURE:
<223> OTHER INFORMATION: VL(1)-CH3_SEED (AG)

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Thr Tyr Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser His Ile Phe Thr
                85                  90                  95

Phe Gly Gln Gly Thr Lys Val Glu Ile Lys Arg Thr Val Ala Pro Glu
            100                 105                 110

Val His Leu Leu Pro Pro Ser Arg Glu Glu Met Thr Lys Asn Gln Val
        115                 120                 125

Ser Leu Thr Cys Leu Ala Arg Gly Phe Tyr Pro Lys Asp Ile Ala Val
    130                 135                 140

Glu Trp Glu Ser Asn Gly Gln Pro Glu Asn Asn Tyr Lys Thr Thr Pro
145                 150                 155                 160

Ser Arg Gln Glu Pro Ser Gln Gly Thr Thr Thr Phe Ala Val Thr Ser
                165                 170                 175

Lys Leu Thr Val Asp Lys Ser Arg Trp Gln Gln Gly Asn Val Phe Ser
```

```
                180                 185                 190
Cys Ser Val Met His Glu Ala Leu His Asn His Tyr Thr Gln Lys Thr
        195                 200                 205

Ile Ser Leu Ser Gly Glu Cys
    210                 215

<210> SEQ ID NO 34
<211> LENGTH: 456
<212> TYPE: PRT
<213> ORGANISM: Artificial Sequence
<220> FEATURE:
<223> OTHER INFORMATION: VH(1)-CH3 (E356K, D399K)-CH2-CH3_HOLE (T366S,
      L368A, Y407V)

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Gln Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Gln Gly Thr Leu Val Thr Val Ser Ser Ala Ser Thr Lys Gly Glu Pro
        115                 120                 125

Gln Val Tyr Thr Leu Pro Pro Ser Arg Lys Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Lys Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320
```

```
Asp Trp Leu Asn Gly Lys Glu Tyr Lys Cys Lys Val Ser Asn Lys Ala
            325                 330                 335

Leu Pro Ala Pro Ile Glu Lys Thr Ile Ser Lys Ala Lys Gly Gln Pro
        340                 345                 350

Arg Glu Pro Gln Val Tyr Thr Leu Pro Pro Ser Arg Glu Glu Met Thr
        355                 360                 365

Lys Asn Gln Val Ser Leu Ser Cys Ala Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Val
            405                 410                 415

Ser Lys Leu Thr Val Asp Lys Ser Arg Trp Gln Gln Gly Asn Val Phe
        420                 425                 430

Ser Cys Ser Val Met His Glu Ala Leu His Asn His Tyr Thr Gln Lys
    435                 440                 445

Ser Leu Ser Leu Ser Pro Gly Lys
    450                 455

<210> SEQ ID NO 35
<211> LENGTH: 456
<212> TYPE: PRT
<213> ORGANISM: Artificial Sequence
<220> FEATURE:
<223> OTHER INFORMATION: VH(1)-CH3 (K392D, K409D)-CH2-CH3_HOLE (T366S,
      L368A, Y407V)

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Gln Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Gln Gly Thr Leu Val Thr Val Ser Ser Ala Ser Thr Lys Gly Glu Pro
        115                 120                 125

Gln Val Tyr Thr Leu Pro Pro Ser Arg Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Asp Thr Thr
                165                 170                 175

Pro Pro Val Leu Asp Ser Asp Gly Ser Phe Phe Leu Tyr Ser Asp Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220
```

```
Leu Ser Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
            245                 250                 255

Lys Asp Thr Leu Met Ile Ser Arg Thr Pro Glu Val Thr Cys Val Val
        260                 265                 270

Val Asp Val Ser His Glu Asp Pro Glu Val Lys Phe Asn Trp Tyr Val
    275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Ser Cys Ala Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Val
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 36
<211> LENGTH: 456
<212> TYPE: PRT
<213> ORGANISM: Artificial Sequence
<220> FEATURE:
<223> OTHER INFORMATION: VH(1)-CH3 (T350V, L351Y, F405A, Y407V)-CH2-
      CH3_HOLE (T366S, L368A, Y407V)

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Gln Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Gln Gly Thr Leu Val Thr Val Ser Ser Ala Ser Thr Lys Gly Glu Pro
```

```
        115                 120                 125
Gln Val Tyr Val Tyr Pro Pro Ser Arg Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Ala Leu Val Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
210                 215                 220

Leu Ser Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Ser Cys Ala Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Val
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 37
<211> LENGTH: 456
<212> TYPE: PRT
<213> ORGANISM: Artificial Sequence
<220> FEATURE:
<223> OTHER INFORMATION: VH(1)-CH3 (T350V, T366L, K392L, T394W)-CH2-
      CH3_HOLE (T366S, L368A, Y407V)

<400> SEQUENCE: 37

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser His
            20                  25                  30

Trp Met His Trp Val Arg Gln Ala Pro Gly Gln Gly Leu Glu Trp Ile
            35                  40                  45

Gly Glu Phe Asn Pro Ser Asn Gly Arg Thr Asn Tyr Asn Glu Lys Phe
 50                  55                  60

Lys Ser Lys Ala Thr Met Thr Val Asp Thr Ser Thr Asn Thr Ala Tyr
 65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
                100                 105                 110

Gln Gly Thr Leu Val Thr Val Ser Ser Ala Ser Thr Lys Gly Glu Pro
            115                 120                 125

Gln Val Tyr Val Leu Pro Pro Ser Arg Glu Glu Met Thr Lys Asn Gln
            130                 135                 140

Val Ser Leu Leu Cys Leu Val Lys Gly Phe Tyr Pro Ser Asp Ile Ala
145                 150                 155                 160

Val Glu Trp Glu Ser Asn Gly Gln Pro Glu Asn Asn Tyr Leu Thr Trp
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
            195                 200                 205

Val Met His Glu Ala Leu His Asn His Tyr Thr Gln Lys Ser Leu Ser
210                 215                 220

Leu Ser Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
            355                 360                 365

Lys Asn Gln Val Ser Leu Ser Cys Ala Val Lys Gly Phe Tyr Pro Ser
            370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Val
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
```

```
                  435                 440                 445
Ser Leu Ser Leu Ser Pro Gly Lys
    450                 455
```

<210> SEQ ID NO 38
<211> LENGTH: 458
<212> TYPE: PRT
<213> ORGANISM: Artificial Sequence
<220> FEATURE:
<223> OTHER INFORMATION: VH(1)-CH3_SEED (AG)-CH2-CH3_HOLE (T366S, L368A, Y407V)

<400> SEQUENCE: 38

```
Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Ser His
            20                  25                  30

Trp Met His Trp Val Arg Gln Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Gln Gly Thr Leu Val Thr Val Ser Ala Ser Thr Lys Gly Pro Glu
        115                 120                 125

Val His Leu Leu Pro Pro Ser Arg Glu Glu Met Thr Lys Asn Gln Val
    130                 135                 140

Ser Leu Thr Cys Leu Ala Arg Gly Phe Tyr Pro Lys Asp Ile Ala Val
145                 150                 155                 160

Glu Trp Glu Ser Asn Gly Gln Pro Glu Asn Asn Tyr Lys Thr Thr Pro
                165                 170                 175

Ser Arg Gln Glu Pro Ser Gln Gly Thr Thr Thr Phe Ala Val Thr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Thr
    210                 215                 220

Ile Ser Leu Ser Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335
```

```
Lys Ala Leu Pro Ala Pro Ile Glu Lys Thr Ile Ser Lys Ala Lys Gly
                340                 345                 350

Gln Pro Arg Glu Pro Gln Val Tyr Thr Leu Pro Pro Ser Arg Glu Glu
            355                 360                 365

Met Thr Lys Asn Gln Val Ser Leu Ser Cys Ala Val Lys Gly Phe Tyr
370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Val Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455
```

<210> SEQ ID NO 39
<211> LENGTH: 459
<212> TYPE: PRT
<213> ORGANISM: Artificial Sequence
<220> FEATURE:
<223> OTHER INFORMATION: VH(1)-CH3_SEED (GA)-CH2-CH3_HOLE (T366S, L368A, Y407V)

<400> SEQUENCE: 39

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Gln Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Gln Gly Thr Leu Val Thr Val Ser Ser Ala Ser Thr Lys Gly Glu Pro
        115                 120                 125

Gln Val Tyr Thr Leu Pro Pro Ser Glu Glu Leu Ala Leu Asn Glu
    130                 135                 140

Leu Val Thr Leu Thr Cys Leu Val Lys Gly Phe Tyr Pro Ser Asp Ile
145                 150                 155                 160

Ala Val Glu Trp Leu Gln Gly Ser Gln Glu Leu Pro Arg Glu Lys Tyr
                165                 170                 175

Leu Thr Trp Ala Pro Val Leu Asp Ser Asp Gly Ser Phe Phe Leu Tyr
            180                 185                 190

Ser Ile Leu Arg Val Ala Ala Glu Asp Trp Lys Lys Gly Asp Thr Phe
        195                 200                 205

Ser Cys Ser Val Met His Glu Ala Leu His Asn His Tyr Thr Gln Lys
    210                 215                 220

Ser Leu Asp Arg Ser Lys Ser Cys Asp Lys Thr His Thr Cys Pro Pro
225                 230                 235                 240
```

Cys Pro Ala Pro Glu Leu Leu Gly Gly Pro Ser Val Phe Leu Phe Pro
            245                 250                 255

Pro Lys Pro Lys Asp Thr Leu Met Ile Ser Arg Thr Pro Glu Val Thr
        260                 265                 270

Cys Val Val Val Asp Val Ser His Glu Asp Pro Glu Val Lys Phe Asn
    275                 280                 285

Trp Tyr Val Asp Gly Val Glu Val His Asn Ala Lys Thr Lys Pro Arg
290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Glu
        355                 360                 365

Glu Met Thr Lys Asn Gln Val Ser Leu Ser Cys Ala Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Val Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Gly Lys
    450                 455

<210> SEQ ID NO 40
<211> LENGTH: 232
<212> TYPE: PRT
<213> ORGANISM: Artificial Sequence
<220> FEATURE:
<223> OTHER INFORMATION: huFc_ KNOB (T366W)

<400> SEQUENCE: 40

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 41
<211> LENGTH: 105
<212> TYPE: PRT
<213> ORGANISM: Artificial Sequence
<220> FEATURE:
<223> OTHER INFORMATION: CH3

<400> SEQUENCE: 41

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro
            100                 105

<210> SEQ ID NO 42
<211> LENGTH: 105
<212> TYPE: PRT
<213> ORGANISM: Artificial Sequence
<220> FEATURE:
<223> OTHER INFORMATION: CH3

<400> SEQUENCE: 42

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro

<210> SEQ ID NO 43
<211> LENGTH: 105
<212> TYPE: PRT
<213> ORGANISM: Artificial Sequence
<220> FEATURE:
<223> OTHER INFORMATION: CH3

<400> SEQUENCE: 43

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Ser Gly Gln Pro Glu
        35                  40                  45

Asn Asn Tyr Asn Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Ile Phe Ser Cys Ser Val Met His Glu Ala Leu His Asn Arg Phe
                85                  90                  95

Thr Gln Lys Ser Leu Ser Leu Ser Pro
            100                 105

<210> SEQ ID NO 44
<211> LENGTH: 105
<212> TYPE: PRT
<213> ORGANISM: Artificial Sequence
<220> FEATURE:
<223> OTHER INFORMATION: CH3

<400> SEQUENCE: 44

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu
            100                 105

<210> SEQ ID NO 45
<211> LENGTH: 111
<212> TYPE: PRT
<213> ORGANISM: Artificial Sequence
<220> FEATURE:
<223> OTHER INFORMATION: CH3

<400> SEQUENCE: 45

Gly Asn Thr Phe Arg Pro Glu Val His Leu Leu Pro Pro Pro Ser Glu
1               5                   10                  15

Glu Leu Ala Leu Asn Glu Leu Val Thr Leu Thr Cys Leu Ala Arg Gly
            20                  25                  30

```
Phe Ser Pro Lys Asp Val Leu Val Arg Trp Leu Gln Gly Ser Gln Glu
            35                  40                  45

Leu Pro Arg Glu Lys Tyr Leu Thr Trp Ala Ser Arg Gln Glu Pro Ser
 50                  55                  60

Gln Gly Thr Thr Thr Phe Ala Val Thr Ser Ile Leu Arg Val Ala Ala
 65                  70                  75                  80

Glu Asp Trp Lys Lys Gly Asp Thr Phe Ser Cys Met Val Gly His Glu
                 85                  90                  95

Ala Leu Pro Leu Ala Phe Thr Gln Lys Thr Ile Asp Arg Leu Ala
            100                 105                 110

<210> SEQ ID NO 46
<211> LENGTH: 106
<212> TYPE: PRT
<213> ORGANISM: Artificial Sequence
<220> FEATURE:
<223> OTHER INFORMATION: CH3

<400> SEQUENCE: 46

Asp Gln Asp Thr Ala Ile Arg Val Phe Ala Ile Pro Pro Ser Phe Ala
 1               5                  10                  15

Ser Ile Phe Leu Thr Lys Ser Thr Lys Leu Thr Cys Leu Val Thr Asp
            20                  25                  30

Leu Thr Thr Tyr Asp Ser Val Thr Ile Ser Trp Thr Arg Gln Asn Gly
            35                  40                  45

Glu Ala Val Lys Thr His Thr Asn Ile Ser Glu Ser His Pro Asn Ala
 50                  55                  60

Thr Phe Ser Ala Val Gly Glu Ala Ser Ile Cys Glu Asp Asp Trp Asn
 65                  70                  75                  80

Ser Gly Glu Arg Phe Thr Cys Thr Val Thr His Thr Asp Leu Pro Ser
                 85                  90                  95

Pro Leu Lys Gln Thr Ile Ser Arg Pro Lys
            100                 105

<210> SEQ ID NO 47
<211> LENGTH: 108
<212> TYPE: PRT
<213> ORGANISM: Artificial Sequence
<220> FEATURE:
<223> OTHER INFORMATION: CH3

<400> SEQUENCE: 47

Asp Ser Asn Pro Arg Gly Val Ser Ala Tyr Leu Ser Arg Pro Ser Pro
 1               5                  10                  15

Phe Asp Leu Phe Ile Arg Lys Ser Pro Thr Ile Thr Cys Leu Val Val
            20                  25                  30

Asp Leu Ala Pro Ser Lys Gly Thr Val Asn Leu Thr Trp Ser Arg Ala
            35                  40                  45

Ser Gly Lys Pro Val Asn His Ser Thr Arg Lys Glu Glu Lys Gln Arg
 50                  55                  60

Asn Gly Thr Leu Thr Val Thr Ser Thr Leu Pro Val Gly Thr Arg Asp
 65                  70                  75                  80

Trp Ile Glu Gly Glu Thr Tyr Gln Cys Arg Val Thr His Pro His Leu
                 85                  90                  95

Pro Arg Ala Leu Met Arg Ser Thr Thr Lys Thr Ser
            100                 105
```

```
<210> SEQ ID NO 48
<211> LENGTH: 108
<212> TYPE: PRT
<213> ORGANISM: Artificial Sequence
<220> FEATURE:
<223> OTHER INFORMATION: CH3

<400> SEQUENCE: 48

Ala Ala Gln Ala Pro Val Lys Leu Ser Leu Asn Leu Leu Ala Ser Ser
1               5                   10                  15

Asp Pro Pro Glu Ala Ala Ser Trp Leu Cys Glu Val Ser Gly Phe
            20                  25                  30

Ser Pro Pro Asn Ile Leu Leu Met Trp Leu Glu Asp Gln Arg Glu Val
        35                  40                  45

Asn Thr Ser Gly Phe Ala Pro Ala Arg Pro Pro Gln Pro Arg Ser
    50                  55                  60

Thr Thr Phe Trp Ala Trp Ser Val Leu Arg Val Pro Ala Pro Pro Ser
65                  70                  75                  80

Pro Gln Pro Ala Thr Tyr Thr Cys Val Val Ser His Glu Asp Ser Arg
                85                  90                  95

Thr Leu Leu Asn Ala Ser Arg Ser Leu Glu Val Ser
            100                 105

<210> SEQ ID NO 49
<211> LENGTH: 4
<212> TYPE: PRT
<213> ORGANISM: Artificial Sequence
<220> FEATURE:
<223> OTHER INFORMATION: Linker

<400> SEQUENCE: 49

Arg Thr Val Ala
1

<210> SEQ ID NO 50
<211> LENGTH: 4
<212> TYPE: PRT
<213> ORGANISM: Artificial Sequence
<220> FEATURE:
<223> OTHER INFORMATION: Linker

<400> SEQUENCE: 50

Glu Pro Gln Val
1

<210> SEQ ID NO 51
<211> LENGTH: 7
<212> TYPE: PRT
<213> ORGANISM: Artificial Sequence
<220> FEATURE:
<223> OTHER INFORMATION: Linker

<400> SEQUENCE: 51

Gln Lys Ser Leu Ser Leu Ser
1               5

<210> SEQ ID NO 52
<211> LENGTH: 5
<212> TYPE: PRT
<213> ORGANISM: Artificial Sequence
<220> FEATURE:
<223> OTHER INFORMATION: Linker

<400> SEQUENCE: 52
```

```
Val Thr Val Ser Ser
1               5

<210> SEQ ID NO 53
<211> LENGTH: 5
<212> TYPE: PRT
<213> ORGANISM: Artificial Sequence
<220> FEATURE:
<223> OTHER INFORMATION: Linker

<400> SEQUENCE: 53

Ala Ser Thr Lys Gly
1               5
```